(12) United States Patent
Shermer et al.

(10) Patent No.: US 7,250,037 B2
(45) Date of Patent: Jul. 31, 2007

(54) PATCH-LIKE INFUSION DEVICE

(75) Inventors: Charles D. Shermer, Raleigh, NC (US); Kenneth G. Powell, Raleigh, NC (US); Alexander G. Lastovich, Raleigh, NC (US); P. Spencer Kinsey, Vernon, CT (US); Chad C. Smutney, Stafford Springs, CT (US); John M. Polidoro, Coventry, CT (US); Ed Browka, Oakland, NJ (US); Carl R. Sahi, Coventry, CT (US); James K. Fentress, Morrisville, NC (US); David S. Chapin, Raleigh, NC (US); Daniel Stipe, Raleigh, NC (US); Jeff M. Moss, Golden, CO (US); Melody Kuroda, Oakland, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 620 days.

(21) Appl. No.: 10/623,702

(22) Filed: Jul. 22, 2003

(65) Prior Publication Data

US 2004/0138612 A1    Jul. 15, 2004

Related U.S. Application Data

(60) Provisional application No. 60/450,680, filed on Mar. 3, 2003, provisional application No. 60/450,681, filed on Mar. 3, 2003, provisional application No. 60/447,359, filed on Feb. 14, 2003, provisional application No. 60/420,233, filed on Oct. 23, 2002, provisional application No. 60/407,284, filed on Sep. 3, 2002, provisional application No. 60/397,038, filed on Jul. 22, 2002.

(51) Int. Cl.
*A61M 5/20*    (2006.01)

(52) U.S. Cl. .................................................... 604/134
(58) Field of Classification Search ................ 604/134, 604/131, 132, 137, 63, 153
See application file for complete search history.

(56) References Cited

U.S. PATENT DOCUMENTS 3,048,171 A * 8/1962 Grau .......................... 604/134

(Continued)

FOREIGN PATENT DOCUMENTS

DE    4039191 C1    11/1991

(Continued)

*Primary Examiner*—Kevin C. Sirmons
*Assistant Examiner*—Elizabeth MacNeill
(74) *Attorney, Agent, or Firm*—Robert E. West

(57) ABSTRACT

A system and method for a patch-like, self-contained substance infusion device which provides one or more substantially hidden patient needles which can be placed in fluid communication with a fluid reservoir subassembly that includes a rigid bladder portion used in conjunction with a non-distensible bladder film, such as a metallized film. Simple removal of an interlock allows a disk, or Belleville spring assembly to apply an essentially even and constant pressure to the contents of the fluid reservoir assembly, and allows the device to then be attached to a skin surface via an adhesive contact surface. A push button activation assembly is provided which can then be used to release and seat one or more spring-loaded patient needles into the skin surface, and establish a fluid communication path between the patient needles and the pressurized fluid reservoir contents thereby delivering an infusion into the skin.

7 Claims, 42 Drawing Sheets

U.S. PATENT DOCUMENTS

| | | | |
|---|---|---|---|
| 3,814,097 A | 6/1974 | Ganderton et al. | 128/268 |
| 3,964,482 A | 6/1976 | Gerstel et al. | 128/260 |
| 4,196,732 A | 4/1980 | Wardlaw | |
| 4,258,711 A | 3/1981 | Tucker et al. | 128/207.19 |
| 4,316,463 A | 2/1982 | Schmitz et al. | 128/218 |
| 4,340,048 A | 7/1982 | Eckenhoff | 128/213 R |
| 4,525,164 A | 6/1985 | Loeb et al. | 604/131 |
| 4,552,561 A | 11/1985 | Eckenhoff et al. | 604/896 |
| 4,772,263 A | 9/1988 | Dormann et al. | |
| 4,781,688 A | 11/1988 | Thoma et al. | |
| 4,886,499 A | 12/1989 | Cirelli et al. | 604/131 |
| 4,921,475 A | 5/1990 | Sibalis | 604/20 |
| 5,011,477 A | 4/1991 | Winchell et al. | |
| 5,045,064 A | 9/1991 | Idriss | |
| 5,090,963 A | 2/1992 | Gross et al. | 604/132 |
| 5,250,023 A | 10/1993 | Lee et al. | 604/20 |
| 5,279,544 A | 1/1994 | Gross et al. | 604/20 |
| 5,554,131 A | 9/1996 | Lacivita | 604/198 |
| 5,649,910 A | 7/1997 | Kriesel et al. | |
| 5,656,032 A | 8/1997 | Kriesel et al. | 604/132 |
| 5,693,018 A | 12/1997 | Kriesel et al. | 604/132 |
| 5,716,343 A | 2/1998 | Kriesel et al. | |
| 5,735,818 A | 4/1998 | Kriesel et al. | 604/132 |
| 5,848,990 A | 12/1998 | Cirelli et al. | 604/136 |
| 5,858,001 A | 1/1999 | Tsals et al. | 604/135 |
| 5,858,005 A | 1/1999 | Kriesel | 604/180 |
| 5,885,250 A | 3/1999 | Kriesel et al. | 604/132 |
| 5,921,962 A | 7/1999 | Kriesel et al. | 604/132 |
| 5,957,895 A * | 9/1999 | Sage et al. | 604/181 |
| 5,961,492 A | 10/1999 | Kriesel et al. | 604/132 |
| 5,997,501 A | 12/1999 | Gross et al. | 604/65 |
| 6,074,369 A * | 6/2000 | Sage et al. | 604/181 |
| 6,099,504 A | 8/2000 | Gross et al. | 604/140 |
| 6,132,755 A | 10/2000 | Eicher et al. | 424/427 |
| 6,186,982 B1 | 2/2001 | Gross et al. | 604/132 |
| 6,500,150 B1 | 12/2002 | Gross et al. | 604/131 |
| 6,589,229 B1 | 7/2003 | Connelly et al. | 604/809.1 |
| 6,595,956 B1 | 7/2003 | Gross et al. | 604/141 |
| 6,611,707 B1 | 8/2003 | Prausnitz et al. | 604/21 |
| 6,656,147 B1 | 12/2003 | Gertsek et al. | |
| 2002/0055711 A1 | 5/2002 | Lavi et al. | 604/110 |
| 2002/0095134 A1 | 7/2002 | Pettis et al. | 604/506 |
| 2003/0045837 A1 | 3/2003 | Delmore et al. | 604/173 |
| 2003/0109827 A1 | 6/2003 | Lavi et al. | 604/134 |
| 2003/0135159 A1 | 7/2003 | Daily et al. | 604/141 |
| 2003/0208167 A1 | 11/2003 | Prausnitz et al. | 604/272 |

FOREIGN PATENT DOCUMENTS

| | | |
|---|---|---|
| WO | WO87/04631 | 8/1987 |
| WO | WO 95/13838 | 5/1995 |
| WO | WO97/10012 | 3/1997 |
| WO | WO 97/21457 | 6/1997 |
| WO | WO97/41917 | 11/1997 |
| WO | WO 00/74763 | 12/2000 |
| WO | WO2005/002649 | 1/2005 |

* cited by examiner

PATCH-LIKE INFUSION DEVICE

CROSS-REFERENCE TO RELATED APPLICATIONS

This application claims benefit under 35 U.S.C. §119(e) from U.S. provisional patent application Ser. No. 60/397,038, entitled "Patch-Like Infusion Device", filed on Jul. 22, 2002; from U.S. provisional patent application Ser. No. 60/407,284, entitled "Patch-Like Infusion Device", filed on Sep. 3, 2002; from U.S. provisional patent application Ser. No. 60/420,233, entitled "Patch-Like Infusion Device", filed on Oct. 23, 2002; from U.S. provisional patent application Ser. No. 60/447,359, entitled "Patch-Like Infusion Device", filed on Feb. 14, 2003; from U.S. provisional patent application Ser. No. 60/450,680, entitled "Patch-Like Infusion Device", filed on Mar. 3, 2003; and from U.S. provisional patent application Ser. No. 60/450,681, entitled "Patch-Like Infusion Device", filed on Mar. 3, 2003; the entire content of each of said provisional applications being expressly incorporated herein by reference.

FIELD OF THE INVENTION

The present invention relates generally to substance delivery devices, and is particularly concerned with a patch-like, wearable, self-contained substance infusion device that can be used to deliver a variety of substances or medications to a patient.

BACKGROUND OF THE INVENTION

A very large number of people require periodic delivery of drugs or other compounds to maintain their health. For example, people suffering from diabetes use daily insulin infusions to maintain close control of their glucose levels. Currently, in the insulin infusion treatment example, there are two principal modes of daily insulin therapy. The first mode includes syringes and insulin pens. These devices are simple to use and are relatively low in cost, but they require a needle stick at each injection, typically three to four times per day. The second is infusion pump therapy, which entails the purchase of an expensive pump that lasts for about three years. The initial cost of the pump is a high barrier to this type of therapy. From a user perspective, however, the overwhelming majority of patients who have used pumps prefer to remain with pumps for the rest of their lives. This is because infusion pumps, although more complex than syringes and pens, offer the advantages of continuous infusion of insulin, precision dosing and programmable delivery schedules. This results in closer glucose control and an improved feeling of wellness.

As their interest in intensive therapy increases, users typically look to insulin pumps. However, in addition to their high cost (roughly 8 to 10 times the daily cost of syringe therapy) and limited lifetime, insulin pumps represent relatively old technology and are cumbersome to use. Also, from a lifestyle standpoint, the tubing (known as the "infusion set") that links the pump with the delivery site on the user's abdomen is very inconvenient and the pumps are relatively heavy, making carrying the pump a bother.

However, patients on oral agents eventually move to insulin, and existing pump therapy is very expensive. Interest in better therapy is on the rise, accounting for the observed growth in pump therapy and increased number of daily injections. In this and similar infusion examples, what is needed to fully meet this increased interest is a form of insulin delivery or infusion that combines the best features of daily injection therapy (low cost and ease of use) with those of the insulin pump (continuous infusion and precision dosing) and that avoids the disadvantages of each.

Several attempts have been made to provide ambulatory or "wearable" drug infusion devices that are low in cost and convenient to use. Some of these devices are intended to be partially or entirely disposable. In theory, devices of this type can provide many of the advantages of an infusion pump without the attendant cost and inconvenience. Unfortunately, however, many of these devices suffer from disadvantages including user discomfort (due to the gauge and/or length of injection needle used), compatibility and interaction between the substance being delivered and the materials used in the construction of the infusion device, and possible malfunctioning if not properly activated by the user (e.g., "wet" injections resulting from premature activation of the device. Difficulties in manufacturing and in controlling needle penetration depth have also been encountered, particularly when short and/or fine-gauge injection needles are used, and the possibility of causing needle-stick injuries to those who come into contact with the used device has also been problematic.

Accordingly, a need exists for an alternative to current infusion devices, such as infusion pumps for insulin, that further provides simplicity in manufacture and use for periodic delivery of drugs and other compounds to the patient.

SUMMARY OF THE INVENTION

An object of the present invention is to provide a patch-like infusion device which can be conveniently worn against the skin while providing infusion of a desired substance.

Another object of the present invention is to provide a patch-like infusion device which provides a hidden patient needle or needles prior to and during use, unlike a conventional syringe.

Another object of the present invention is to provide a patch-like infusion device which provides minimal discomfort by using one or more microneedles.

Another object of the present invention is to provide a patch-like infusion device which can be secured to a patient via an adhesive surface.

Another object of the present invention is to provide a patch-like infusion device which provides a pressurizing content reservoir.

Another object of the present invention is to provide a patch-like infusion device which provides a pressurizing content reservoir using a bladder and Belleville spring assembly.

Another object of the present invention is to provide a patch-like infusion device which allows pressurizing the contents of a content reservoir through a single or an optional secondary energizing step.

Another object of the present invention is to provide a patch-like infusion device which allows pressurizing the contents of a content reservoir by removing a Belleville spring retaining pin via a pull handle assembly in a single or an optional secondary energizing step.

Another object of the present invention is to provide a patch-like infusion device which provides patient needle implantation and reservoir content delivery through a single or an optional secondary activation step.

Another object of the present invention is to provide a patch-like infusion device which can be activated via a reasonable force applied to a vertical or horizontal push button in a single or an optional secondary activation step.

Another object of the present invention is to provide a patch-like infusion device which allows pressurizing the contents of a content reservoir, patient needle implantation and reservoir content delivery through a combined single energizing and activation step.

Another object of the present invention is to provide a patch-like infusion device which allows for visual inspection of the device contents before, during and after use.

Another object of the present invention is to provide a patch-like infusion device which automatically shields or covers the patient needle or needles upon intentional or accidental removal from the skin surface.

Another object of the present invention is to provide a patch-like infusion device which provides an interlock between the pull handle assembly and the push button to prevent accidental activation.

Another object of the present invention is to provide a patch-like infusion device which allows for removal of a patient needle cap, and/or pull handle assembly, and/or an adhesive cover in one or more motions.

Another object of the present invention is to provide a patch-like infusion device which facilitates self-injection and reduces or eliminates variations in injection techniques between users.

These and other objects are substantially achieved by providing a system and method for a patch-like, wearable, self-contained substance infusion device which provides one or more substantially hidden patient needles which can be placed in fluid communication with a content reservoir assembly that includes a rigid bladder portion used in conjunction with a bladder film, such as a metallized film which is typically non-distensible in normal use. Simple removal of a retaining pin allows a disk or Belleville spring assembly to apply an essentially even and constant pressure to the contents of the reservoir assembly, and allows the device to then be attached to a skin surface via an adhesive contact surface. A push button activation assembly is provided which can then be used to release and seat one or more spring-loaded patient needles into the skin surface, and establish a fluid communication path between the patient needles and the pressurized reservoir contents thereby delivering an infusion of contents into the skin of the user.

BRIEF DESCRIPTION OF THE DRAWINGS

The various objects, advantages and novel features of the preferred embodiments of the present invention will be more readily appreciated from the following detailed description when read in conjunction with the appended drawings, in which.

Throughout the drawings, like reference numerals will be understood to refer to like parts, components or structures.

DETAILED DESCRIPTION OF THE PREFERRED EMBODIMENTS

Introduction

Figure 1:
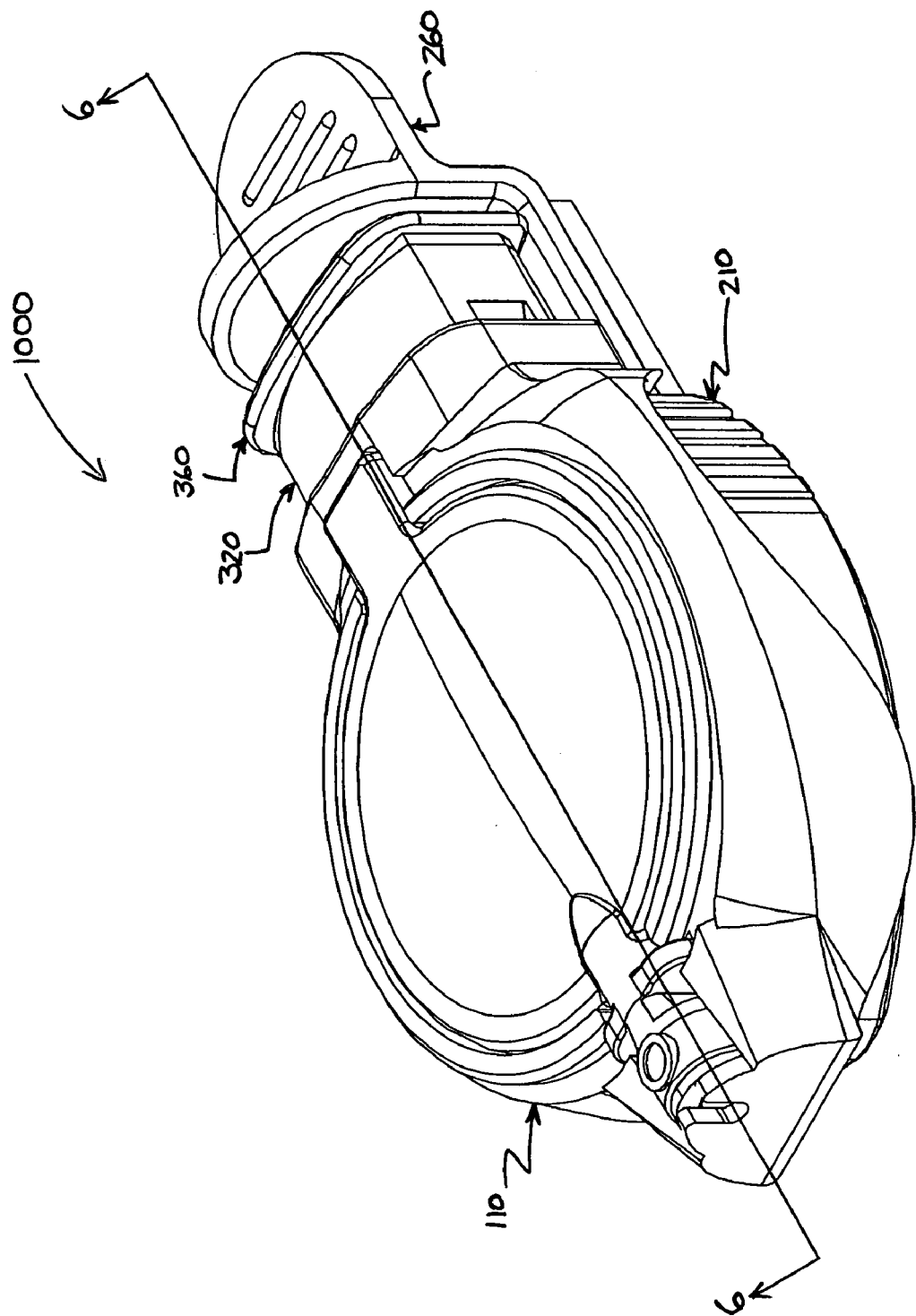
FIG. 1 is a top perspective view of a first embodiment of a patch-like injector or infuser system using a side push button prior to energizing and activating.
Figure 2:
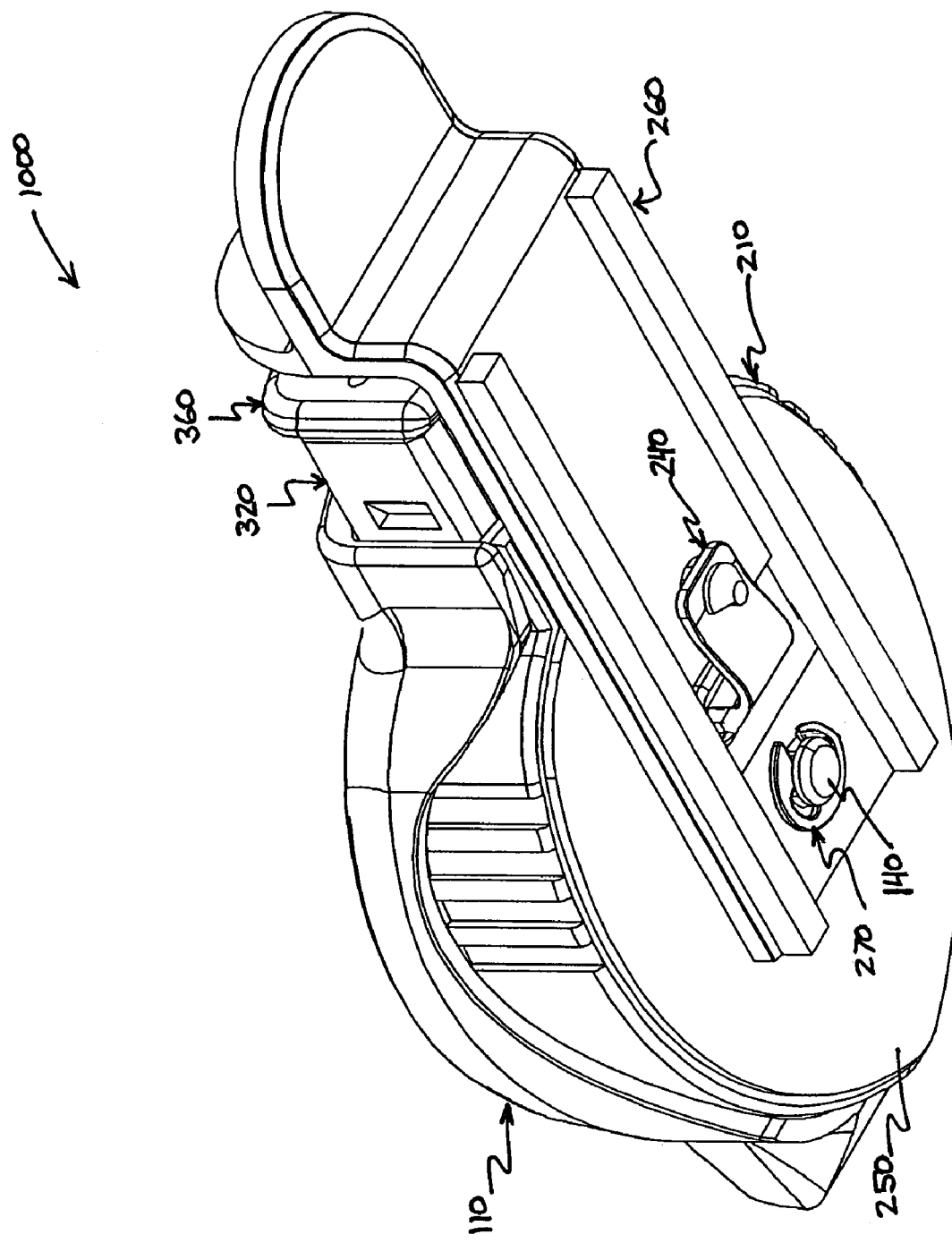
FIG. 2 is a bottom perspective view of the first embodiment of a patch-like injector or infuser system using a side push button.

The embodiments of the present device described below can be used as a convenient, patch-like device to deliver a pre-measured dose of a substance, such as a drug or medication, to a user through an adhesive attached infusion device. The device is self-contained and is attached to the skin surface of the user by adhesive disposed on a bottom surface. Once properly positioned and activated by the user, the pressure of a released Belleville spring on a reservoir surface within the device can be used to empty the contents of the flexible reservoir through one or more patient microneedles via a needle manifold. The substance within the reservoir is then delivered through the skin of the user by the microneedles which are driven into the skin by one or more springs contained in the device. It will be understood that other embodiments are possible in which the Belleville spring is replaced with a different type of stored energy device which may be mechanical, electrical and/or chemical in nature.

As will be appreciated by one skilled in the art, there are numerous ways of carrying out the patch-like injection or infuser system disclosed herein. Although reference will be made to the embodiments depicted in the drawings and the following descriptions, the embodiments disclosed herein are not meant to be exhaustive of the various alternative designs and embodiments that are encompassed by the disclosed invention. In each disclosed embodiment, the device is referred to as an infusor; however, the device may also inject substances at a much faster bolus rate than is commonly accomplished by infuser devices. For example, the contents can be delivered in a period as short as several seconds, or as long as several days.

General Structure

In a first embodiment of the present invention shown in FIGS. 1 through 11, an infusion device 1000 includes a reservoir subassembly 100, including an upper housing 110, a reservoir base surface 120, at least one Belleville spring 130, a retaining pin 140, fill plug 150, septum 160 and reservoir film 170. The infusion device 1000 further includes a housing subassembly 200, including a lower housing 210, and patient needle manifold 220 having at least one patient needle 222 and a manifold film 224. The housing subassembly 200 further includes a needle shield 230, needle shield drive spring 232 and an adjustable needle cap 240. An adhesive layer 250 is disposed upon the lower surface of the lower housing 210, and can be covered by a removable film (not shown), and a pull handle 260. A clip 270, such as an "E" clip can be used to secure the retaining pin 140 to the pull handle 260. The infusion device 1000 further includes a push button subassembly 300, including at least one patient needle manifold drive spring 310, a push button slide 320, at least one septum needle 330, a septum needle sheath 340 and a fluid communication tube 350. A button face 360 can be provided to complete the push button subassembly 300. In the description below, the term reservoir is often used to describe the assembled and separate reservoir base surface 120, fill plug 150, septum 160 and reservoir film 170 of the reservoir subassembly 100.

As noted above, the components of the embodiment shown in FIGS. 10A through 10C can be categorized into several subassemblies for ease in description as presented below. Such subassemblies include, but are not limited to, the reservoir subassembly 100, housing subassembly 200 and push button subassembly 300. An assembled embodiment of the present invention is shown in FIGS. 1 through 5, and illustrative cross sectional views are shown in FIGS. 5 through 9.

As shown in FIGS. 1 through 5, the embodiment of the present invention 1000 can be constructed of these subassemblies to provide a patch-like, wearable, self-contained substance infusion device that can be used to deliver a variety of medications to a patient. The device 1000, shown in a pre-energized, pre-activated position in FIG. 1, provides a hidden patient needle or needles prior to and during use, and can be secured to a patient via an adhesive surface. The pressurization of the contents of the reservoir can be achieved by removing the pull handle 260 to "energize" the device and device contents, and the device can then be "activated" via a reasonable force applied to the push-button 360 to seat the patient needles and establish a flow path between the reservoir and needles. In doing so, the device 1000 facilitates self-injection and reduces or eliminates variations in injection techniques between users.

Figure 3:
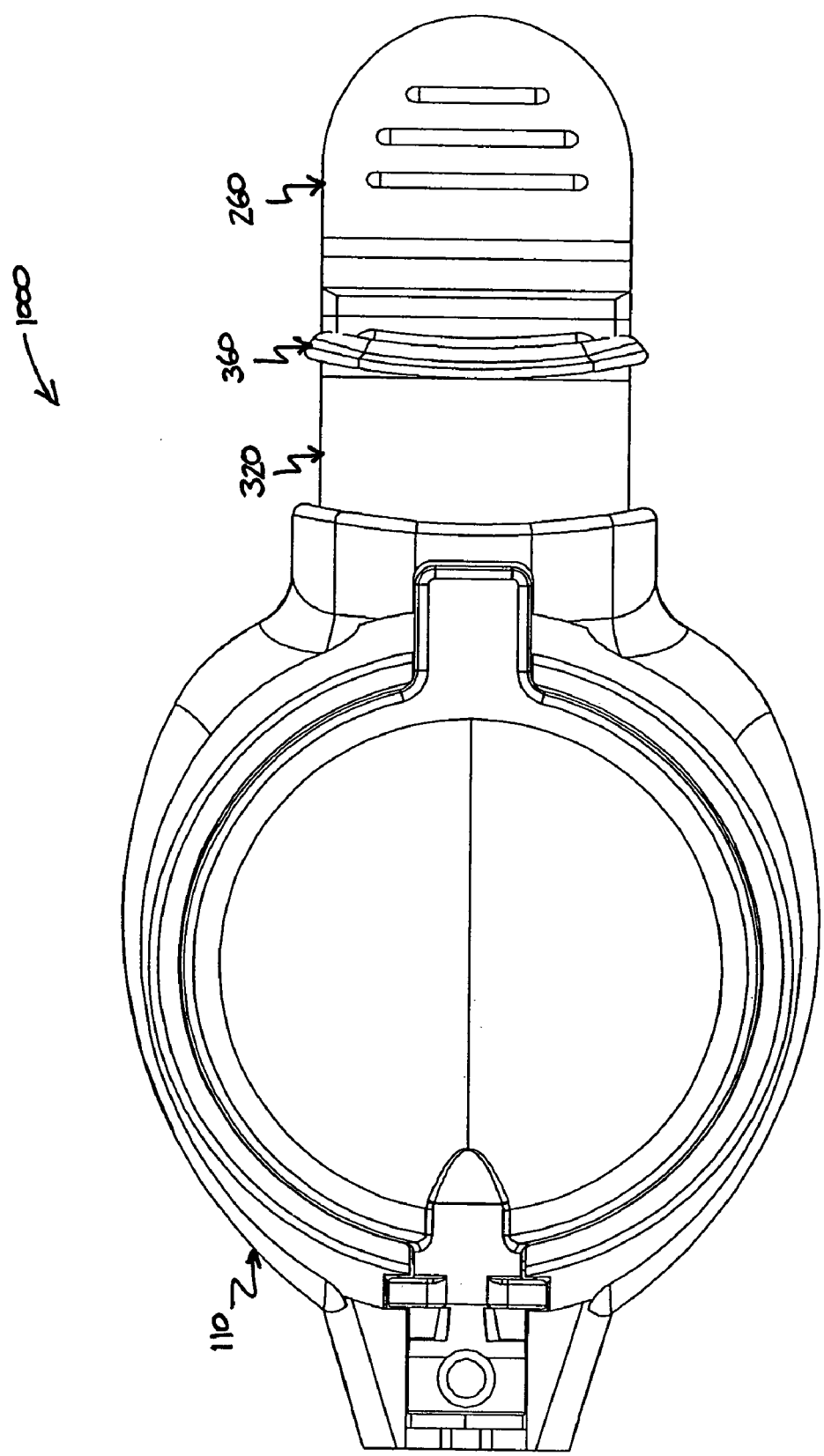
FIG. 3 is a top view of the first embodiment of a patch-like injector or infuser system using a side push button.
Figure 4:
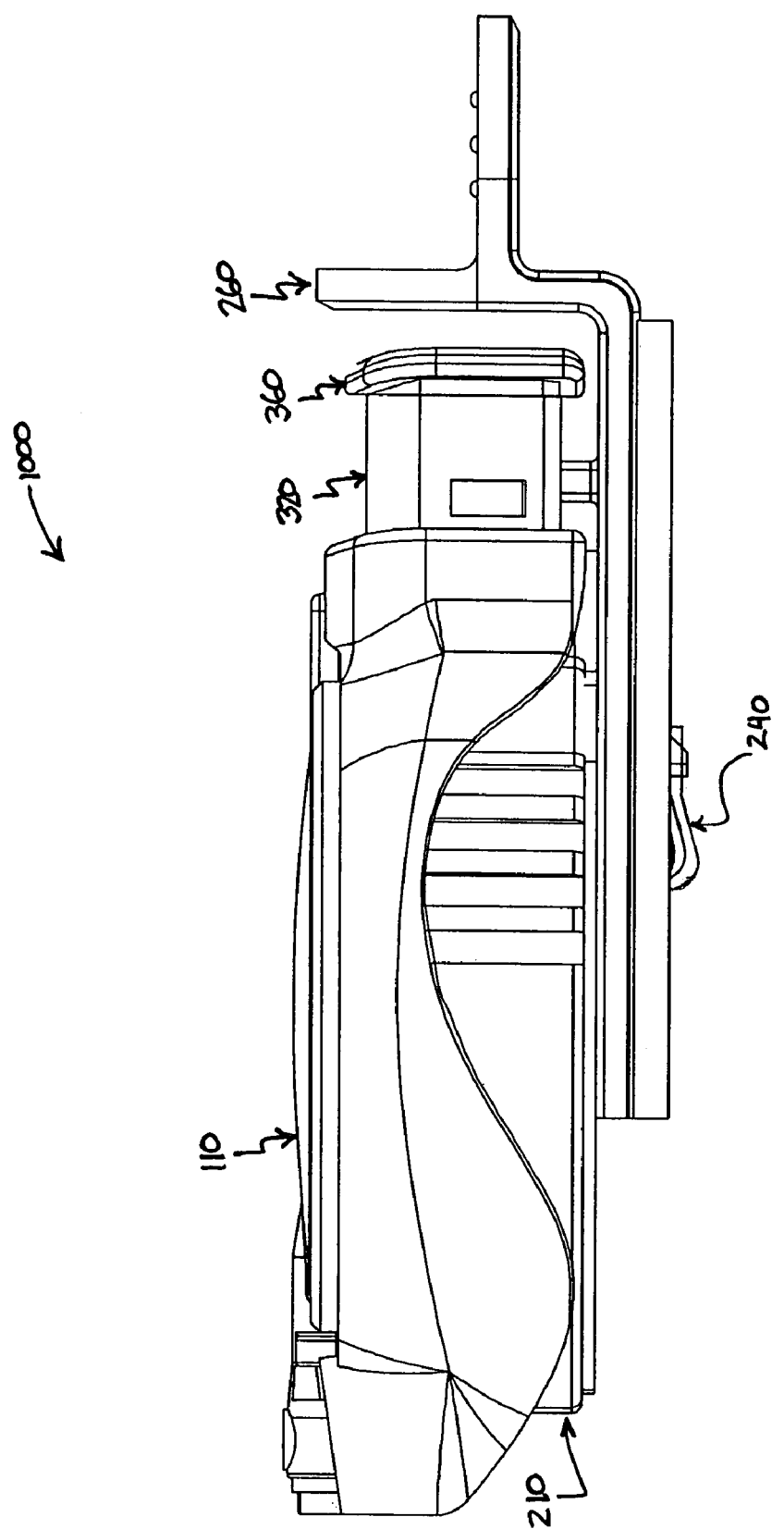
FIG. 4 is a side elevational view of the first embodiment of a patch-like injector or infuser system using a side push button.
Figure 5:
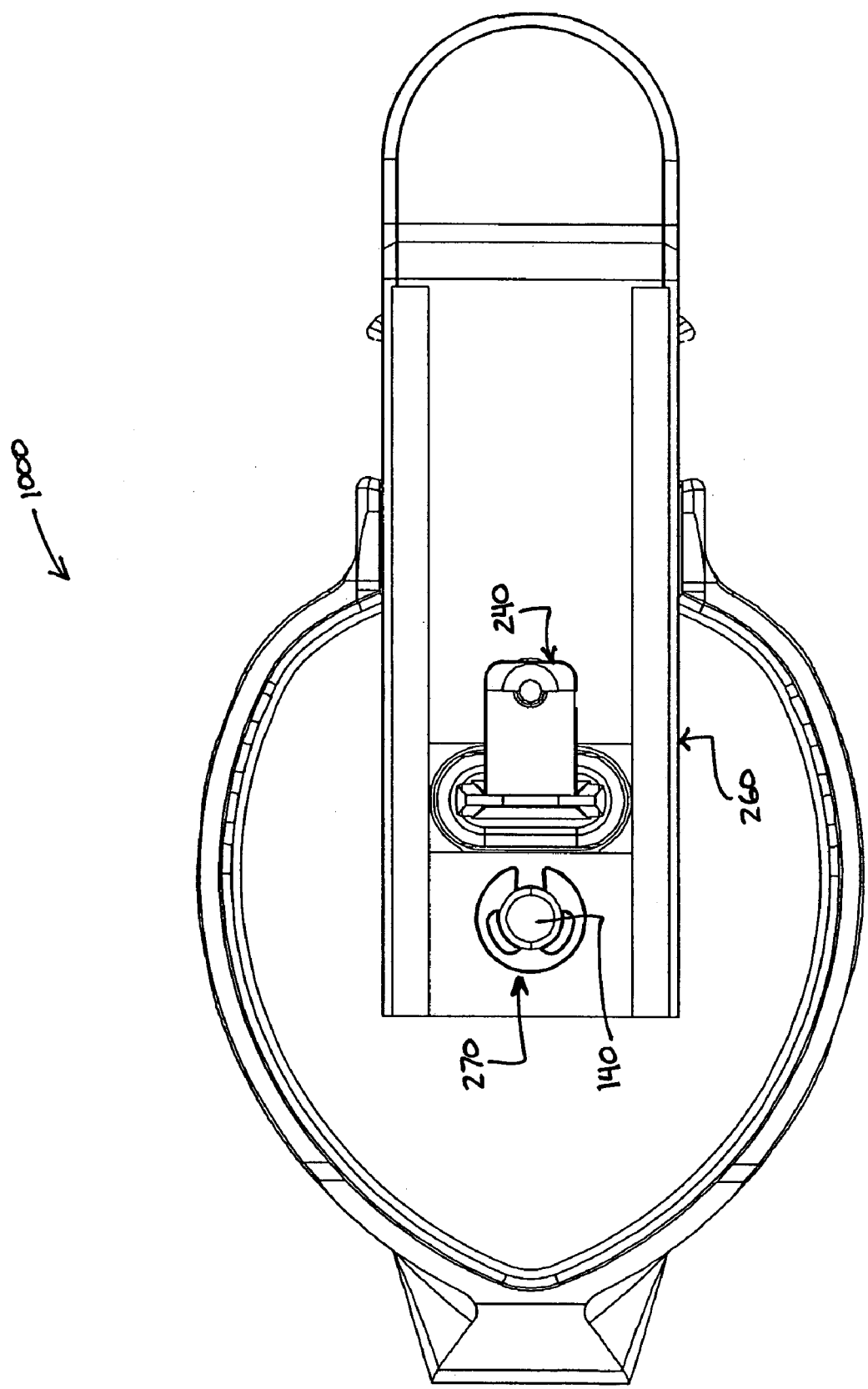
FIG. 5 is a bottom view of the first embodiment of a patch-like injector or infuser system using a side push button.
Figure 6:
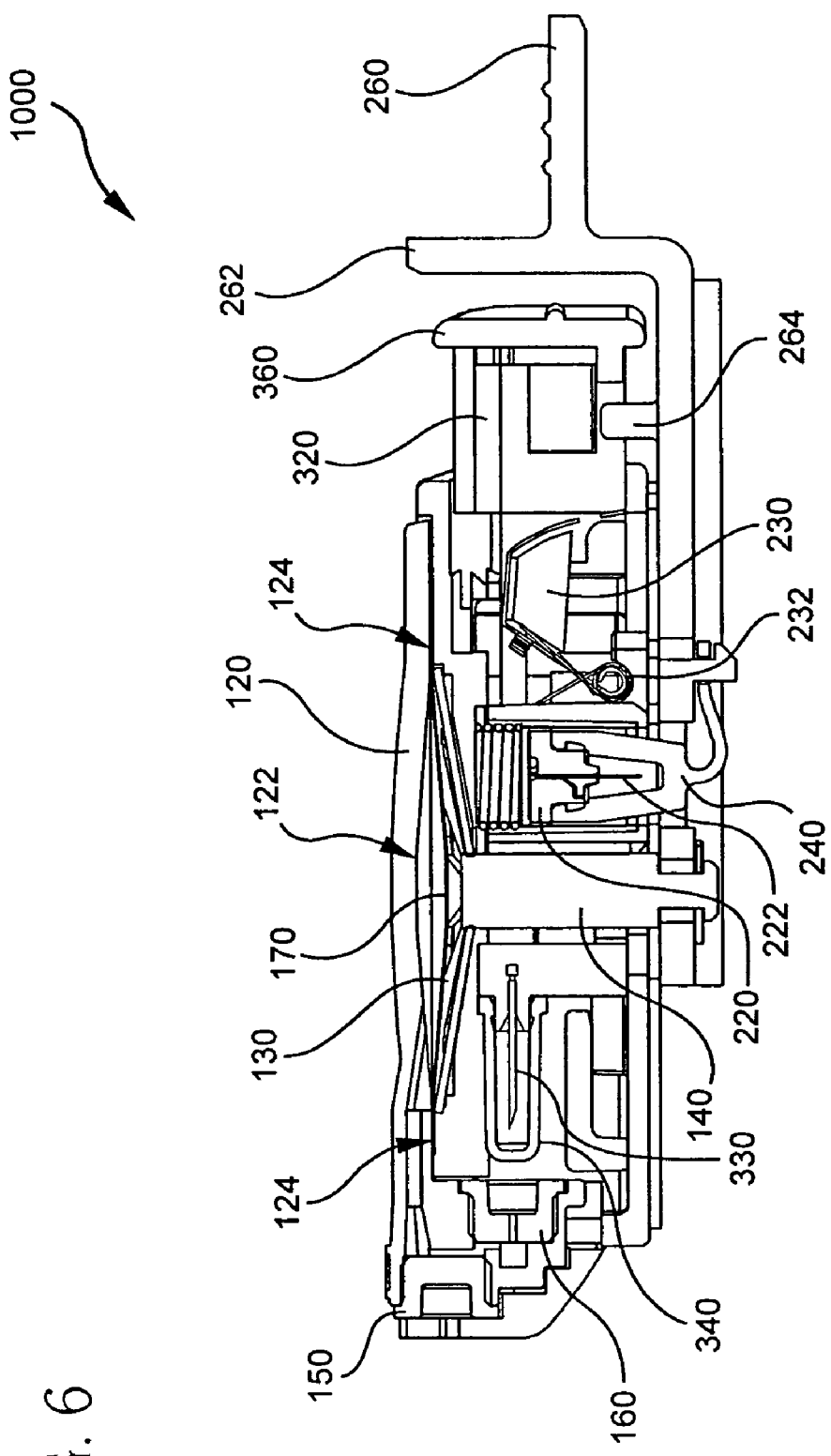
FIG. 6 is a cross-sectional view (6-6 in FIG. 1) of the first embodiment of a patch-like injector or infuser system using a side push button.
Figure 7:
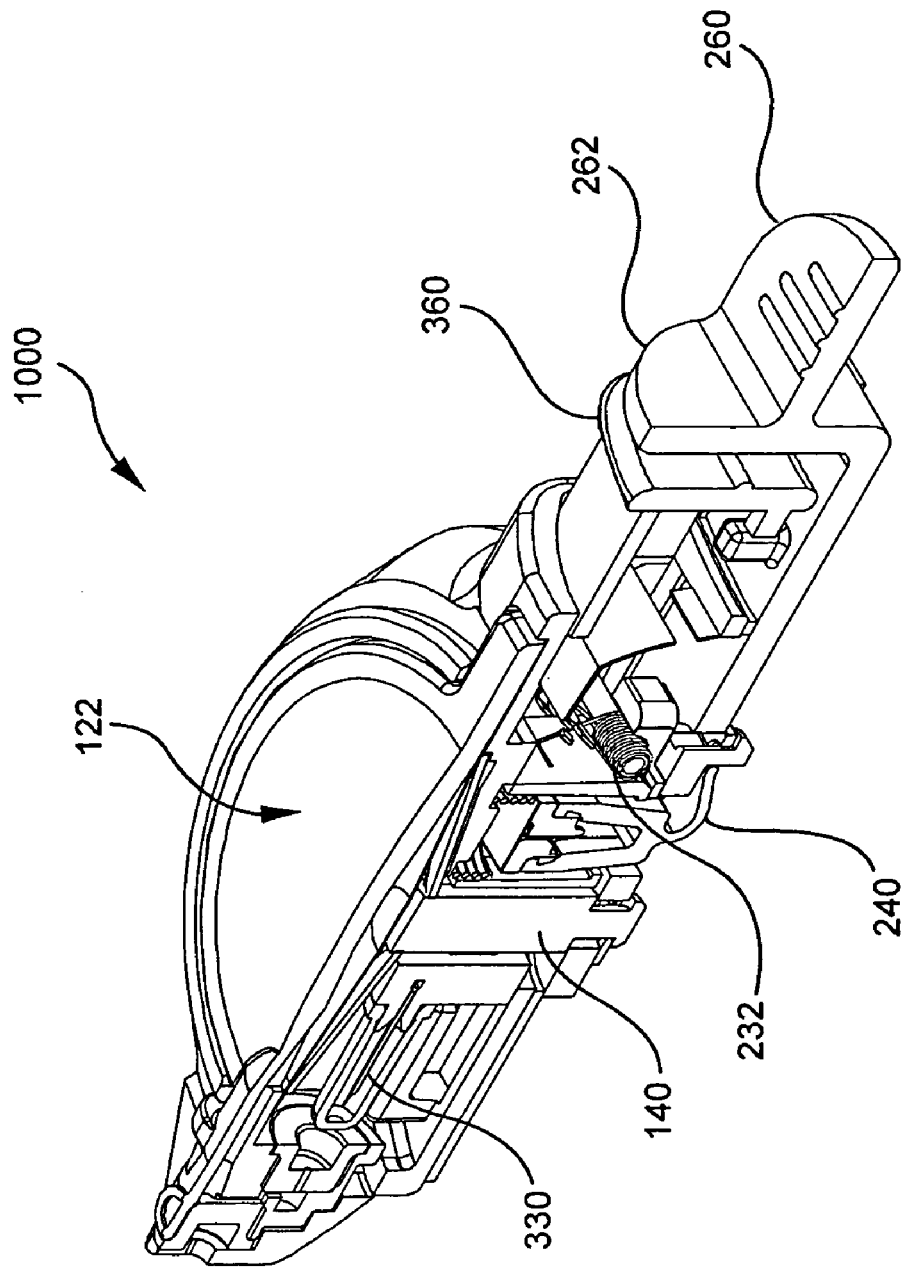
FIG. 7 is a cross-sectional view (6-6 in FIG. 1) from a first perspective angle of the first embodiment of a patch-like injector or infuser system using a side push button.
Figure 8:
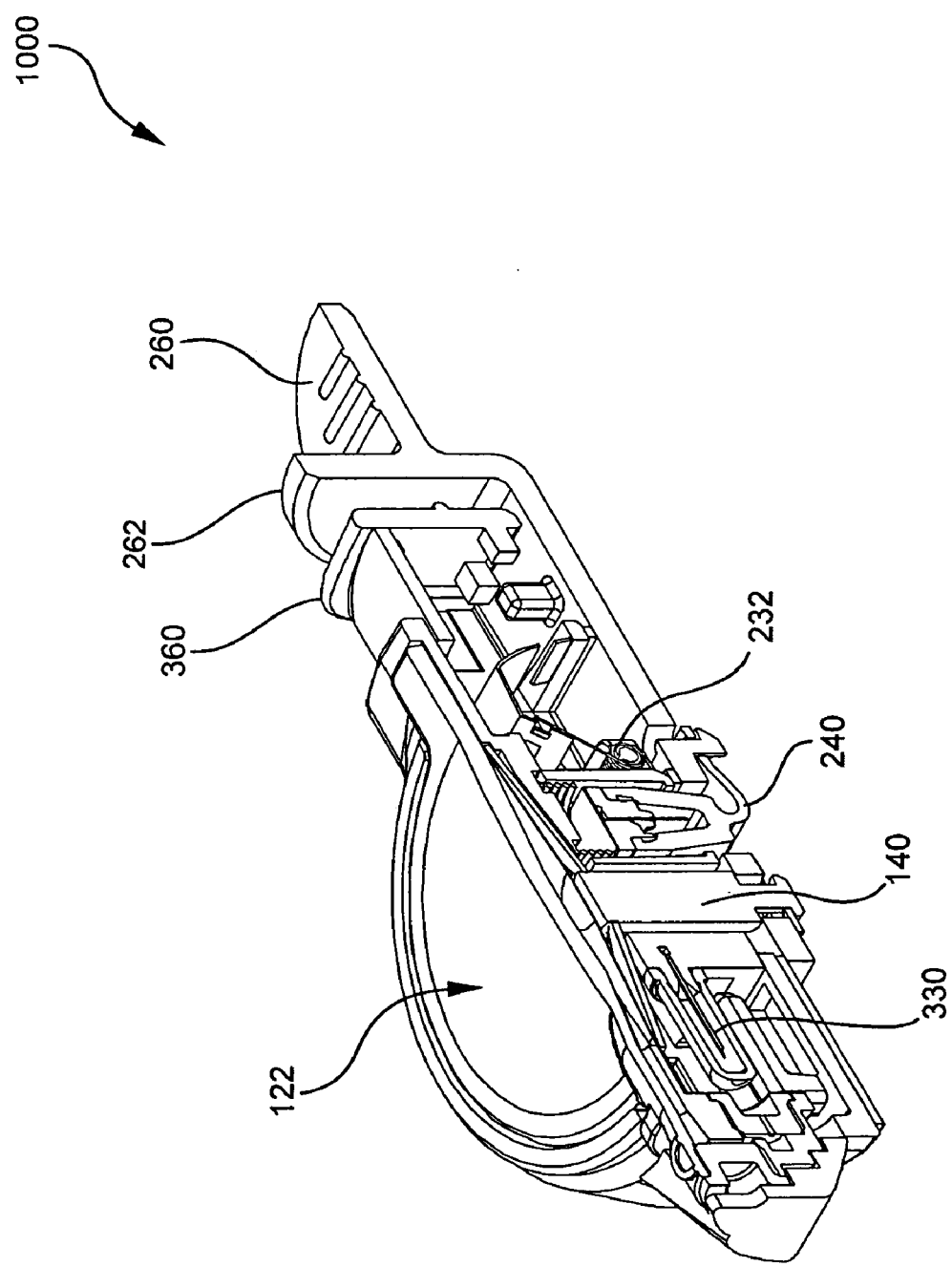
FIG. 8 is a cross-sectional view (6-6 in FIG. 1) from a second perspective angle of the first embodiment of a patch-like injector or infuser system using a side push button.
Figure 9:
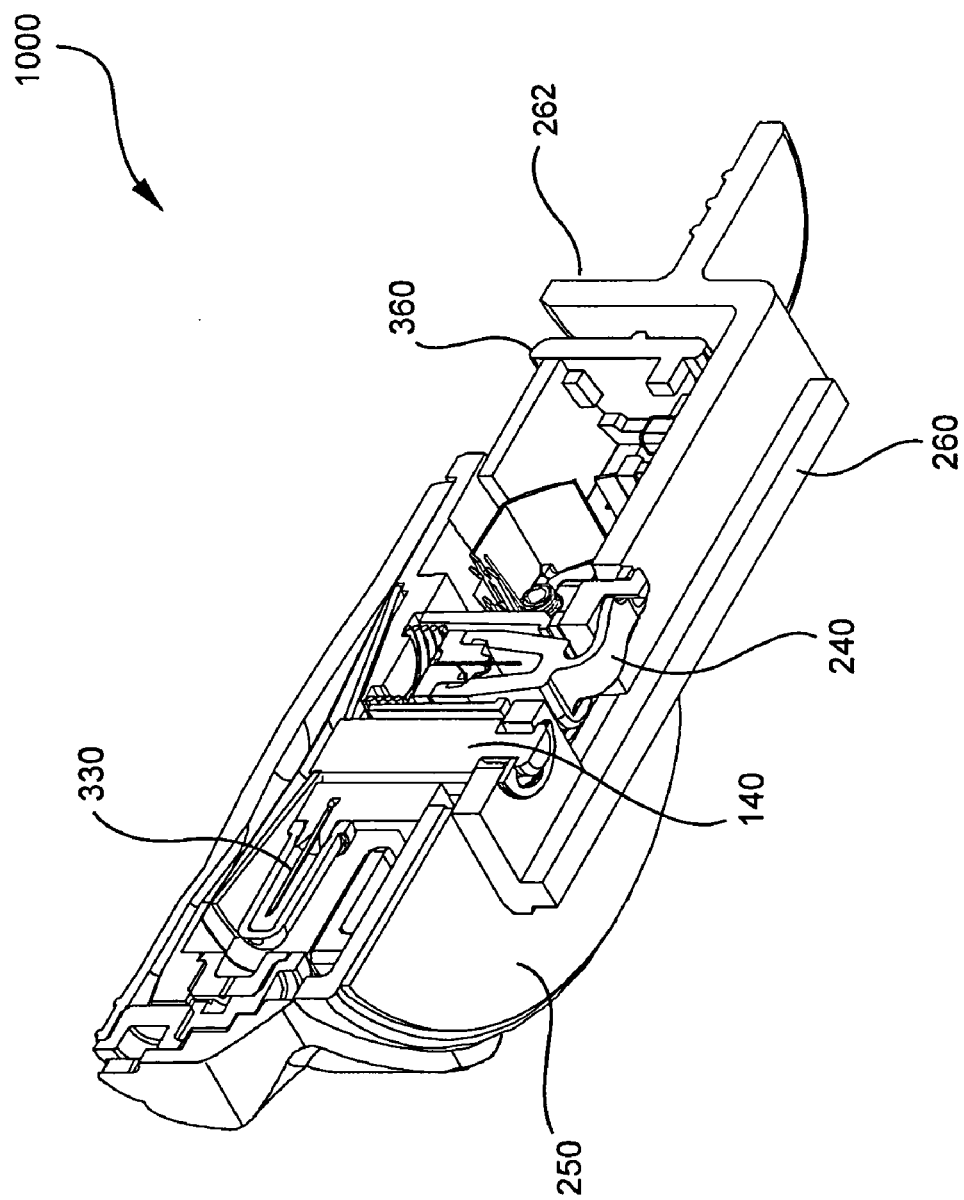
FIG. 9 is a cross-sectional view (6-6 in FIG. 1) from a third perspective angle of the first embodiment of a patch-like injector or infuser system using a side push button.

FIG. 1 is a top perspective view of a first embodiment of the infusion device 1000. In FIG. 1, the assembled upper and lower housing 110 and 210 respectively is shown, between which the push button subassembly 300 is contained. The pull handle 260, described in greater detail below, is shown in a pre-energized, pre-activated position and serves to secure the retaining pin 140 within the device and shield the push button 360 from any applied forces. As more clearly illustrated in FIG. 2, which is a bottom perspective view of the first embodiment, the pull handle 260 is further interlocked with the needle cap 240 and the retaining pin 140 via clip 270. Also, as illustrated in FIG. 6, which is a cross-sectional view (6-6 in FIG. 1) of the first embodiment, the pull handle 260 is further interlocked with the push button slide 320. A top view of the first embodiment shown in FIG. 3 illustrates the alignment and travel between the push button slide 320 and the device, which is required for activation. FIG. 4 is a side elevational view of the first embodiment and illustrates the low profile of the device and the centered positioning of the patient needle opening, which is more clearly illustrated in the bottom view of the first embodiment shown in FIG. 5.

FIGS. 6 through 9, and FIG. 11A through 11C, illustrate a number of cross-sectional views (6-6 in FIG. 1) of the first embodiment and illustrate the construction, positioning and operation of each subassembly in a pre-energized, pre-activated position, and subsequent post-energized and post-activated positions, each described in greater detail in separate sections below.

Reservoir Subassembly

Figure 10A:
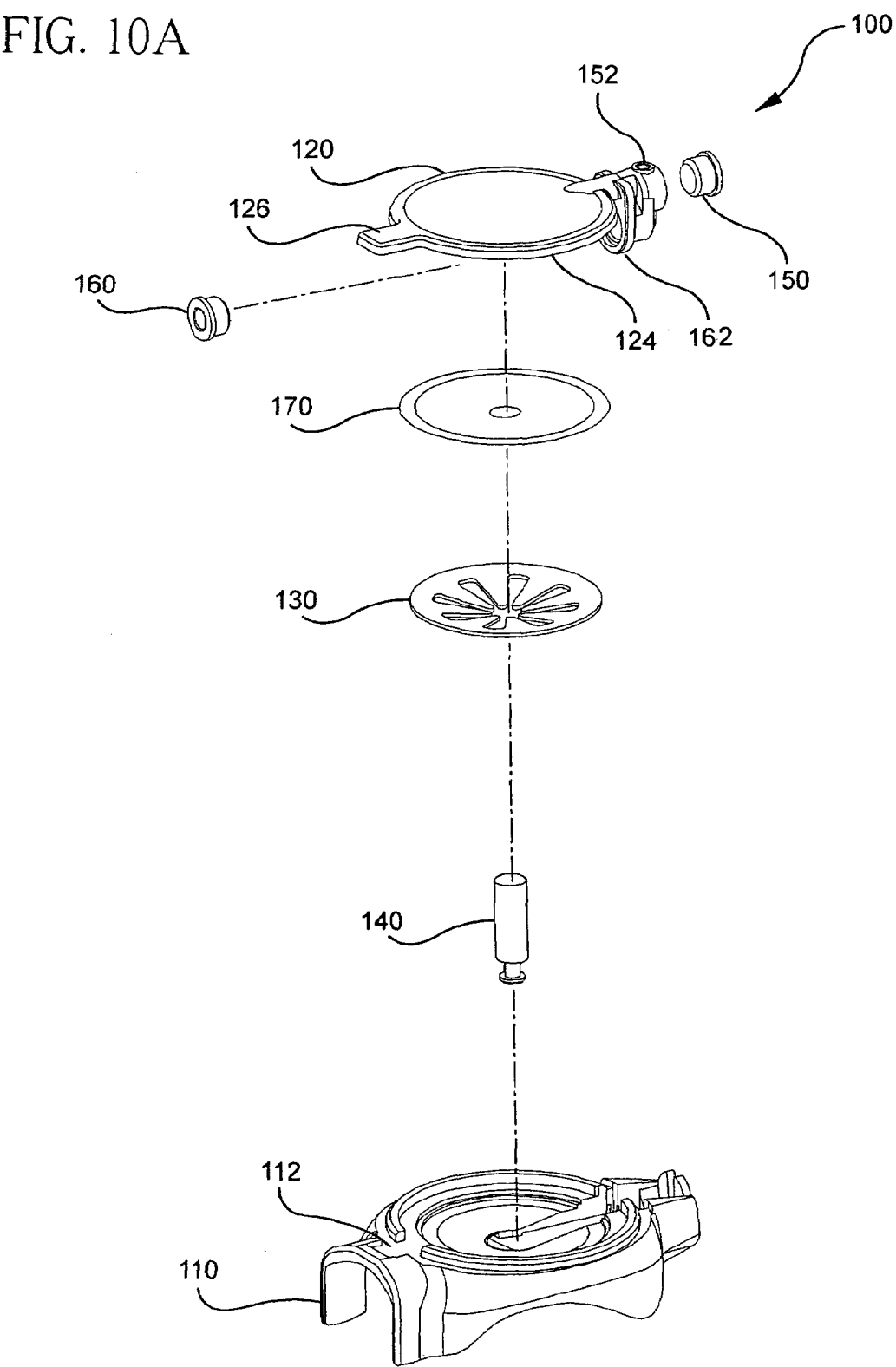
FIG. 10A is an exploded view of a reservoir subassembly of the first embodiment shown in FIG. 1.

In FIG. 10A, the reservoir subassembly 100 of the infusion device 1000 is shown, and can be comprised of a rigid portion 120 used in conjunction with one or more non-distensible but flexible films 170, such as metallized films. The reservoir subassembly 100 can contain any number of substances between either a first and second film, where either the first or second film is also positioned against the rigid portion, or between a first film and the rigid portion.

The rigid portion 120, or reservoir base, can be comprised of and serve as a hard portion of the reservoir against which the flexible film 170 can be pressed as described in greater detail below. As shown more clearly in FIG. 6, the rigid portion 120 can contain a dished out central section 122 and a flange 124, provided about the perimeter of the rigid portion to allow for heat sealing the flexible film 170, or film lid, to the rigid portion and to form a content reservoir, or chamber, therebetween. The reservoir subassembly of FIG. 10A can further provide a guide opening 112 for mateably receiving a guide 126 for precise positioning and attachment between the rigid portion 120 and the upper housing 110 using any number of techniques, such as ultrasonic staking.

As noted above, the reservoir of the embodiment shown in FIG. 10A can be constructed to preferably have a hard shell or inner surface, and at least one flexible film attached about the perimeter of the hard shell or inner surface. The flexible film 170 can be heat sealed to the rigid portion 120 to create a chamber, or bladder, for storage of device contents. As at least one wall of the chamber comprises a flexible film 170, and at least one wall of the chamber comprises a rigid surface, one or more Belleville springs 130 can be placed adjacent to the flexible film 170 and used to apply a substantially constant pressure to the flexible film 170, and pressurize the reservoir chamber and contents.

Figure 12:
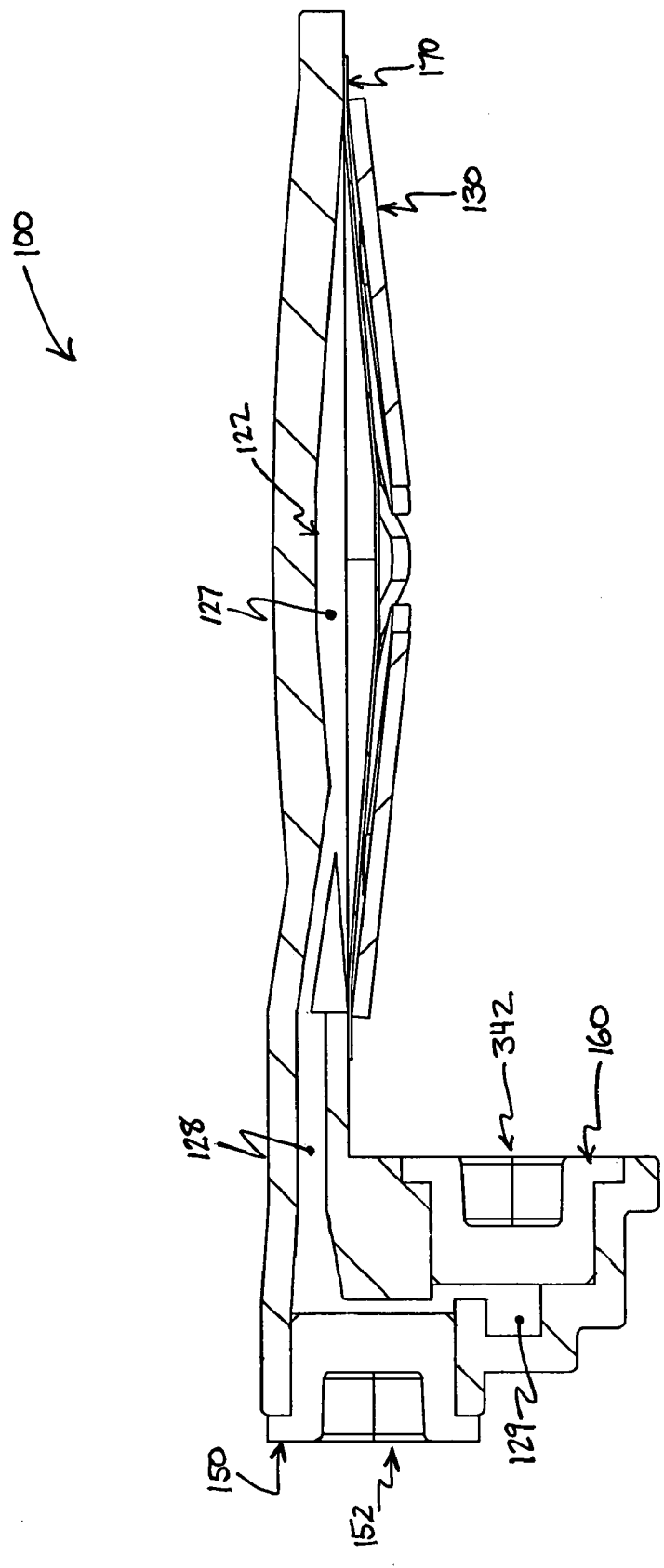
FIG. 12 is a partial cross sectional view of the fluid path and reservoir subassembly of FIG. 10A.

As shown in FIGS. 6 and 10A, a Belleville spring 130 is provided to apply a substantially even and constant pressure to the flexible film 170 of the reservoir subassembly 100, compressing the contents of the reservoir between the flexible film 170 and the rigid portion 120, and forcing the contents from the reservoir through one or more flow paths as shown in greater detail in FIG. 12, which illustrates a partial cross-sectional view of the fluid path and reservoir subassembly of FIG. 10A. As noted above, the reservoir of FIG. 10A can also be made up of two or more flexible, non-distensible films, wherein the contents can be contained between the films where at least one film is attached to the rigid portion 120 to provide a rigid base for compressing and pressurizing the contents of the reservoir. In yet another embodiment of the reservoir subassembly 100, the flow rate is automatically adjusted from an initial high rate to one or more stepped-down lower flow rates. Additional details of an adjusting flow rate are further discussed in U.S. patent application Ser. No. 10/396,719, entitled "Multi-Stage Fluid Delivery Device And Method", filed on Mar. 26, 2003, the entire content of which is incorporated herein by reference.

The flexible film 170 of the reservoir subassembly 100 can be made of non-distensible materials or laminates, such as metal-coated films or other similar substances. For example, one possible flexible laminate film which can be used in the reservoir subassembly 100 of the first embodiment can be comprised of a first polyethylene layer, a second chemical layer as known to those skilled in the art to provide an attachment mechanism for a third metal layer, which is chosen based upon barrier characteristics, and followed by a fourth layer comprised of either polyester or nylon. By utilizing a metal-coated or metallized film 170 in conjunction with a rigid portion 120, the barrier properties of the reservoir are improved, thereby increasing or improving the shelf life of the contents contained within. For example, where a reservoir content includes insulin, the primary materials of contact in the reservoir subassembly 100 of the embodiment described above include linear, low-density polyethylene (LLDPE), low-density polyethylene (LDPE), cyclic olefin copolymer (COC) and Teflon. As described in greater detail below, the primary materials of contact in the remaining flow path of the reservoir contents include polyethylene (PE), medical grade acrylic, and stainless steel. Such materials which are in extended contact with the contents of the reservoir subassembly preferably pass ISO 10-993 and other applicable biocompatibility testing.

Figure 13:
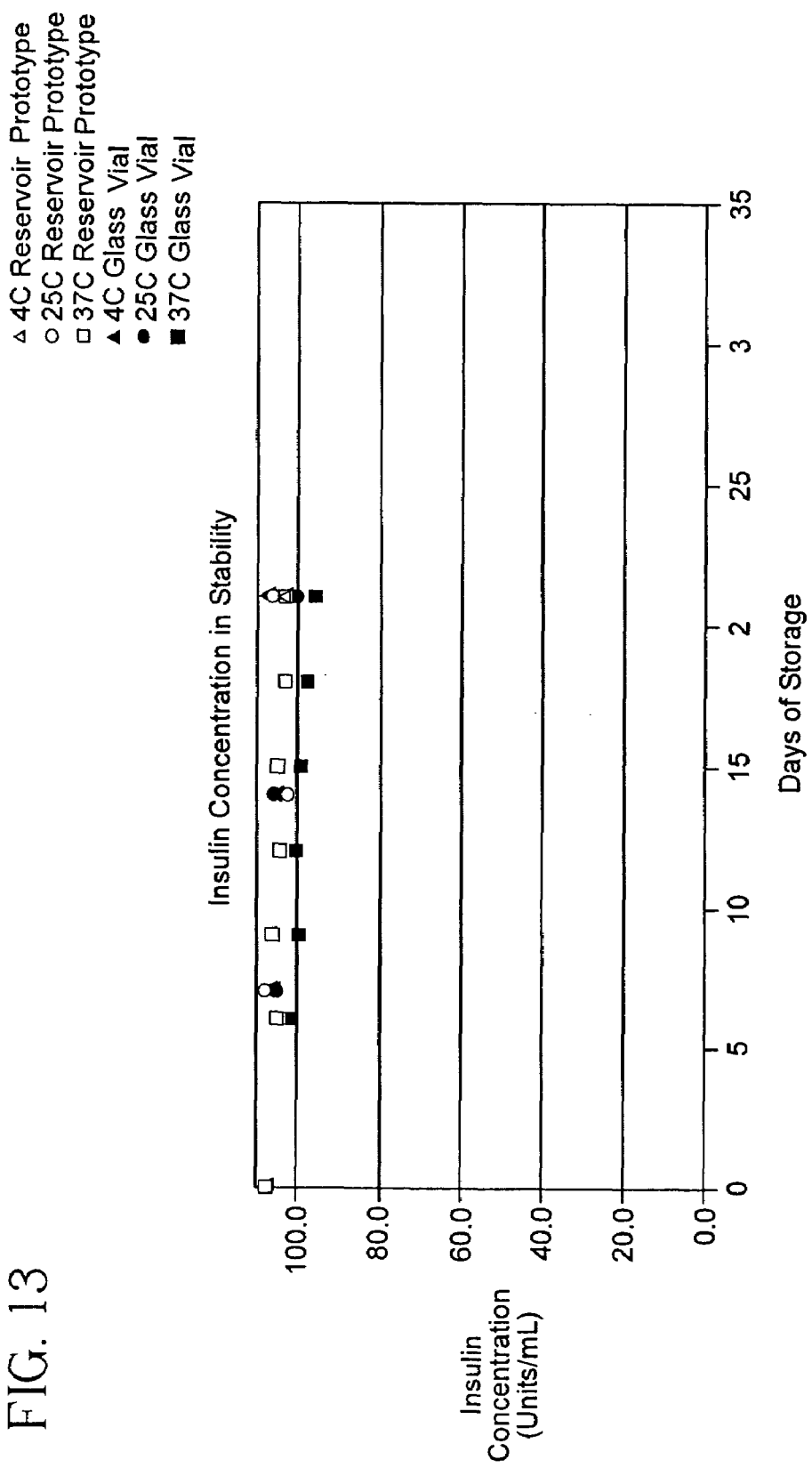
FIG. 13 is a plot illustrating an example of insulin stability data for a reservoir subassembly in accordance with an embodiment of the present invention.

The reservoir of the reservoir subassembly 100 is further preferably able to be stored for the prescribed shelf life of the reservoir contents in applicable controlled environments without adverse effect to the contents and is capable of applications in a variety of environmental conditions. Additionally, the barrier provided by the components of the reservoir do not permit the transport of gas, liquid and solid materials into or out of the contents at a rate greater than that allowable to meet the desired shelf life. In the embodiment shown in FIG. 10A, the reservoir subassembly materials are capable of being stored and operated in a temperature range of approximately 34 to 120 degrees F., and can have a shelf life of two or more years. For example, as shown in FIG. 13, the reservoir subassembly as described above has no impact on insulin stability during use with the device. FIG. 13 is a plot illustrating an example of insulin stability data for the reservoir subassembly of FIG. 10A.

In FIG. 13, the insulin stability of reservoir contents, which is plotted as insulin concentration levels along the Y axis, is shown for 6 insulin containing devices over a storage period of 25 (or more) days. The compared devices include the first embodiment of the present invention having a 4 CC reservoir, a 25 CC reservoir, and a 37 CC reservoir, as well as a 4 CC, 25 CC, and 37 CC glass vial insulin containing device. As shown in FIG. 13, the insulin concentration in stability samples varies very little over the 25 day period, and little or no difference is noted between plots for each device over the same period. In addition to satisfying stability requirements, the reservoir can further ensure operation by successfully passing any number of leak tests, such as holding a 30 psi sample for 20 minutes without leaking. Additional filling, storage and delivery benefits resulting from the configuration of the reservoir subassembly include minimized headspace and adaptability as described in greater detail below.

The reservoir of the reservoir subassembly 100 is preferably evacuated prior to filling, as described in greater detail below. By evacuating the reservoir of FIG. 10A prior to filling, and having only a slight depression 122 in the hard floor of the rigid portion 120, headspace and excess waste within the reservoir can be minimized. In addition, the shape of the reservoir may be configured to adapt to the type of energizing mechanism used, e.g., a disk or Belleville spring 130 having any number of diameter and height dimensions. Additionally, using an evacuated flexible reservoir during filling minimizes any air or bubbles within the filled reservoir. The use of a flexible reservoir is also very beneficial when the device is subjected to external pressure or temperature variations, which can lead to increased internal reservoir pressures. In such case, the flexible reservoir expands and contracts with the contents, thereby preventing possible leaks due to expansion and contraction forces exerted on the fill plug 150 and septum 160. This also helps to eliminate dose variation due to temperature and pressure fluctuations in the environment.

As noted above, the small depression 122 located on the surface of the rigid portion 120 helps to inhibit the formation of fluid retaining pockets as the reservoir film 170 collapses under the pressure of the Belleville spring 130. This depression also assists in filling the reservoir system by providing a fluid flow path since it is preferable to evacuate the system prior to introducing fluid into it. This introduction of fluid can be accomplished at the time the device is manufactured, or right up to the time it is to be used by the end user. For example, in one filling method the reservoir can be evacuated, filled via the fill port 152, then provided a fill plug 150. Alternatively in a second filling method, the reservoir can be evacuated, then provided a fill plug 150, and later filled through the fill plug 150 prior to use. This allows the reservoir of the device to be received at a drug filling location in such a manner as to allow for aseptic filling with low headspace and a sterility-maintaining connection of fluid flow paths. As described in greater detail below, any reservoir access needles and patient needles can also be capped in this sterility-maintaining manner.

Yet another feature of the reservoir subassembly 100 includes the ability to permit automated particulate inspection at the time of fill, or by a user at the time of use. One or more reservoir barriers, such as the rigid portion 120, can be molded of a transparent, clear plastic material, which allows inspection of the substance contained within the reservoir. The transparent, clear plastic material is preferably a cyclic olefin copolymer that is characterized by high transparency and clarity, low extractables and biocompatibility with the substance contained in the reservoir. A suitable material is available from Zeon Chemicals, L.P., of Louisville, Ky. under the designation "BD CCP Resin", and is listed by the U.S. Food and Drug Administration as DMF No. 16368. In such applications, the reservoir includes minimal features which could possibly obstruct inspection (i.e. rotation during inspection is permitted).

Fluid Path

The rigid portion 120 of the reservoir subassembly 100 of FIG. 10A further comprises at least one a fluid path 128 as shown in FIG. 12, which accesses the main chamber 127 of the reservoir. In the embodiment shown in FIG. 12, the fluid path 128 exits the main chamber 127 of the reservoir, passing under or through the heat seal area provided about the perimeter of the rigid portion 120 for securing the flexible film 170, and into a chamber 129 between a fill-head stopper 150 and a septum 160, allowing fluid of the reservoir to travel from the reservoir to the septum 160. In the embodiment shown in FIG. 12, the fluid path 128 is preferably constructed to reduce dead volume and incorporates the fill-head receiving geometry as described in greater detail below.

The fluid path 128 is constructed of materials similar or identical to those described above for the reservoir subassembly, and that satisfy numerous biocompatibility and storage tests. For example, as shown in Table 1 below, where the device content includes insulin, the primary materials of contact in the reservoir subassembly 100 of the embodiment includes linear, low-density polyethylene, cyclic olefin copolymer and Teflon, and can also include a transparent, clear plastic. The primary materials of contact in the remaining flow path between the reservoir subassembly and the microneedles 222 of the patient needle manifold 220 include polyethylene, medical grade acrylic, and/or stainless steel.

TABLE 1

| Path Component | Material |
| --- | --- |
| Reservoir | Polyethylene, cyclic olefin copolymer and/or Teflon |
| Reservoir Film | metal-coated film, such as polyethylene, aluminum, polyester and/or nylon with a chemical tie layer, such as the product A83, manufactured by Beacon Converters of Saddle Brook N.J. |
| Septum | Halo-butyl rubber |
| Septum Needle | Stainless steel |
| Septum Needle Manifold | Polyethylene and/or medical grade acrylic |
| Tube | Polyethylene with a PVC outer layer and a Ethyl Vinyl Acetate tie layer |
| Patient Needle Manifold | Polyethylene and/or medical grade acrylic |
| Patient Needle Manifold Film | Polyester, aluminum and a sealant layer, such as the product A40, manufactured by Beacon Converters of Saddle Brook N.J. |
| Patient Needle | Stainless steel |

Specifically, the patient and septum needles 222 and 330 respectively, can be constructed of stainless steel, the septum needle manifold 322 and patient needle manifold 220 can be constructed of polyethylene and/or medical grade acrylic, the septum 160 can be constructed of halo-butyl rubber, and the flexible tube 350 between the septum needle and/or the septum needle manifold and the patient needle manifold can be constructed of polyethylene with a PVC outer layer and a Ethyl Vinyl Acetate tie layer. Such materials when in extended contact with the contents of the reservoir subassembly preferably pass ISO 10-993 biocompatibility testing.

The septum 160 of FIG. 10A, is positioned between the first fluid path 128 and a second fluid path comprised of the septum needle 330, septum needle manifold 322, and tube 350, and can be an elastomeric plug that when penetrated by a septum spike or septum needle 330, creates a sterile flow path between the reservoir and the patient needles 222. The septum needle 330, which is used to penetrate the septum 160 and create a flow path between the first and second fluid paths, can include a septum needle boot 340 that maintains the sterility of the septum needle prior to, and after the boot is collapsed and the fluid path is created.

As described in greater detail below, the septum needle 330 can be significantly larger than the patient needles 222, such as 25-29 gauge, to allow easier handling and preventing flow restriction. As more clearly shown in FIGS. 10C and 12, the septum needle boot 340, or sheath, is sized to engage a recess opening 342 provided by the septum elastomeric plug 160 prior to being pierced by the septum needle 330.

This engagement between the septum needle boot 340 and the recess opening 342 provided by the septum elastomeric plug 160 creates a sterile environment through which the septum needle 330 travels when piercing the septum needle boot and septum, such that at no time is the septum needle exposed to a non-sterile environment.

Fill Head Port

Returning to FIGS. 10A and 12, the chamber 129 between the septum 160 and reservoir can also be accessed through a fill-head port 152 located in the reservoir subassembly 100 which can be closed with a fill-head stopper 150. The fill-head stopper 150 and septum 160 can be identical parts, which further reduces manufacturing complexity.

Through the use of the fill-head port 152, the device can allow filling of the reservoir from an external source even after complete assembly and/or at the point of use. In a first fill method, a completed, fully assembled device can be provided without a fill plug 150 in place in the fill-head port 152, and the fill plug, or fill-head stopper, can then be added after filling the reservoir with a filler device. Alternatively in a second fill method, a completed, fully assembled, yet unfilled device can be provided with the fill-head stopper 150 in place in the fill-head port 152, and then filled by injecting through the fill-head stopper using a standard syringe or similar device. Since the top of the reservoir can be made of a clear material, fill levels and excess air can be easily seen and withdrawn using the same syringe. In this way, careful control of fill volume and dose delivery can be maintained.

For infusor devices which are pre-filled, the fill-head port 152 is provided with the fill-head stopper 150 which closes the fill-head port. The upper housing 110 can then be used to hold the fill-head stopper 150 in place and prevent the stopper from backing out while also providing access to the fill-head stopper for filling where desired. For infusor devices which allow filling at the time of use, the fill-head port 152 can remain accessible, either through the fill-head stopper 150 as described above, or through an inner collar beyond the removed fill-head stopper. In each filling application, the fill-head port 152 allows fluid to travel from an external source via the fluid path 128 described above, into the main chamber 127 of the reservoir subassembly 100, which can further include input and output ports to aid in filling.

Where filling at the time of use is to occur, the device does not require the activation steps outlined in detail below. When the device is to be filled at the time of use, the Belleville spring 130 is not required to be held in a retracted position by a retaining pin 140, as pressure applied to the empty reservoir by the released Belleville spring will have no effect. Filling the device at the time of use serves to displace the Belleville spring 130, which is free to press the reservoir subassembly and force contents from the reservoir once the external filling pressure source is removed from communication with the reservoir. Additionally, such filling at the time of use allows sterile packaging steps without the restrictions presented by a device containing a medication.

Belleville Spring

As shown in FIG. 10A, a disk or Belleville spring 130 is included in the device 1000 for applying an essentially even, constant force to the reservoir to force the contents from the reservoir, and is hereinafter sometimes referred to as a "constant force spring". The constant force spring 130 is used to store energy that, when released by device activation, pressurizes the reservoir at the time of use. The spring 130 is held in a flexed state by a pin 140 positioned at the center of a plurality of spring fingers. In doing so, the spring is prevented from putting stress on the film 170 of the reservoir subassembly 100 or any remaining device components during storage.

The pin 140, or retaining pin, can be any suitable pin, tube or ring, that is sufficiently rigid to resist spring tension and deformation, and secure the pin to a removal mechanism, such as a pull handle 260 described in greater detail below. The pin 140 should not fail under normal tensile load or, if part of an assembly, should not disassemble at forces that can be induced by shipping and handling, and resulting in inadvertent activation.

Figure 10B:
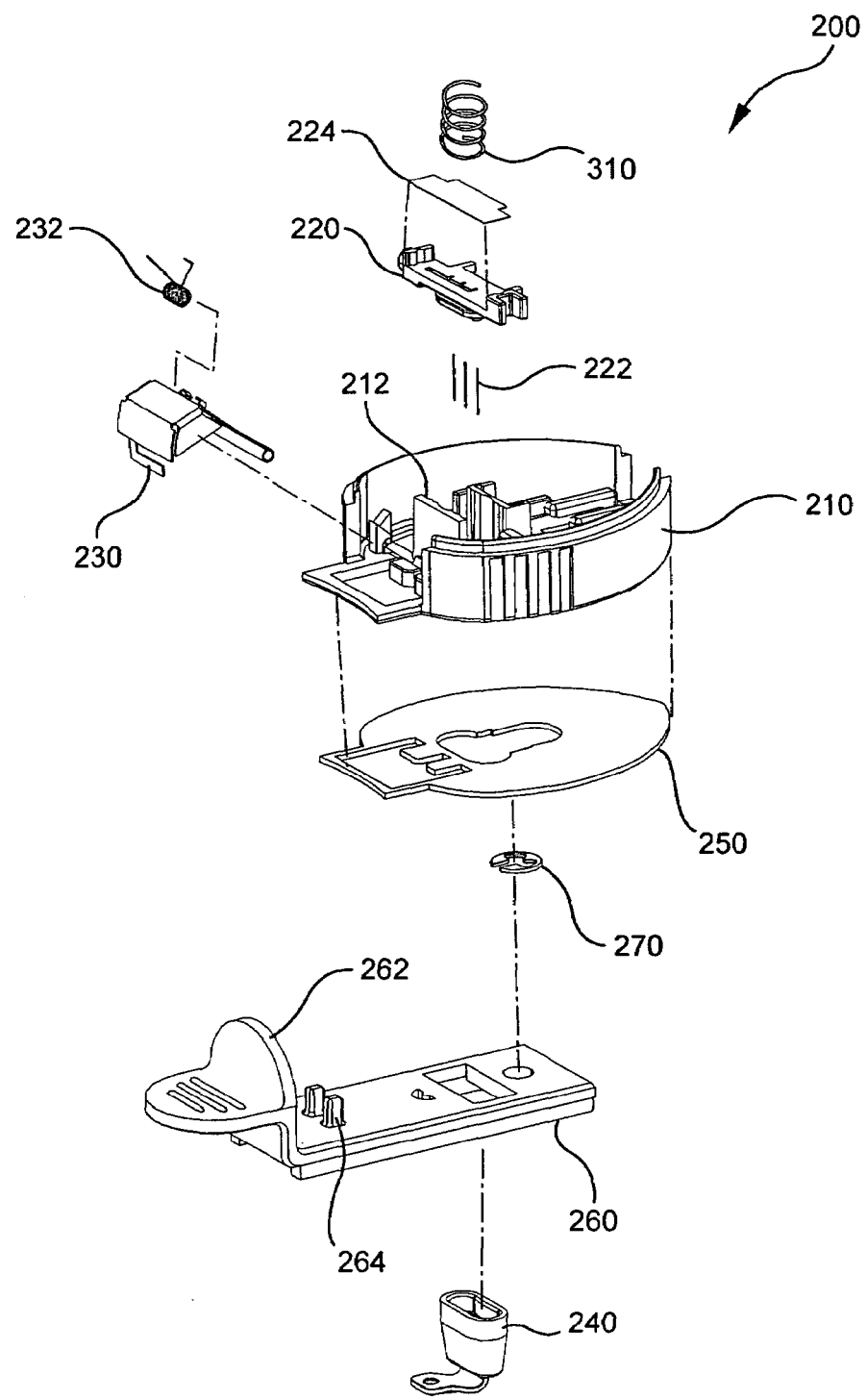
FIG. 10B is an exploded view of a housing subassembly of the first embodiment shown in FIG. 1.

In FIG. 10B, a pull handle 260 is provided to aid in the removal of the retaining pin 140 described above. The pull handle 260 is positioned adjacent to the bottom surface of the device, and includes one or more members which extend to one side of the device creating a mechanical advantage for the removal of the retaining pin 140. In the embodiment shown in FIG. 10B, the pull handle 260 includes a member 262 that extends and shields the button head 360 of the push button subassembly 300. In doing so, the pull handle 260 prevents the application of a force to the push button 360 until the pull handle is removed. This prevents accidental activation of the device via the push button prior to proper placement.

In the embodiment described above, the pull handle 260 includes a member which prevents the application of a force to the push button. In other versions of this embodiment, the pull handle can include a member which extends between the push button and the device housing to prevent movement of the push button when a force is applied to the push button.

Still other pull handle/push button interlocks can be provided between the pull handle 260 and the needle cap 240 and the retaining pin 140, ensuring proper operation and preventing accidental activation. For example, in FIG. 10B, the pull handle 260 also includes members 264 that extend from the pull handle surface into openings in the push button slide 320 and prevents the application of a force to the push button 360 from moving the slide until the pull handle has been removed, activating the device.

In yet another version of the embodiment described above, the push button and button slide itself can serve to release the retaining pin. In this version, as the push button is activated, the retaining pin is skewed from a substantially perpendicular position relative to the Belleville spring. As the retaining pin is skewed further and further, the retaining pin is eventually released from the Belleville spring. Removal of the pull handle 260 can also include a tactile and audible indicator providing user feedback.

When the retaining pin 140 is pulled free of the Belleville spring 130, the fingers of the spring drop, and in doing so, exert a force on the film lid 170 of the reservoir subassembly 100. The edge of the spring 130 is trapped between the reservoir and the upper housing, and can be configured to preferably create a pressure within the reservoir of from about 1 to 50 psi, and more preferably from about 2 to about 25 psi, and most preferably from about 15 to about 20 psi for intradermal delivery of the reservoir contents. For subcutaneous injection or infusion, a range of about 2 to 5 psi may be sufficient.

Figure 14:
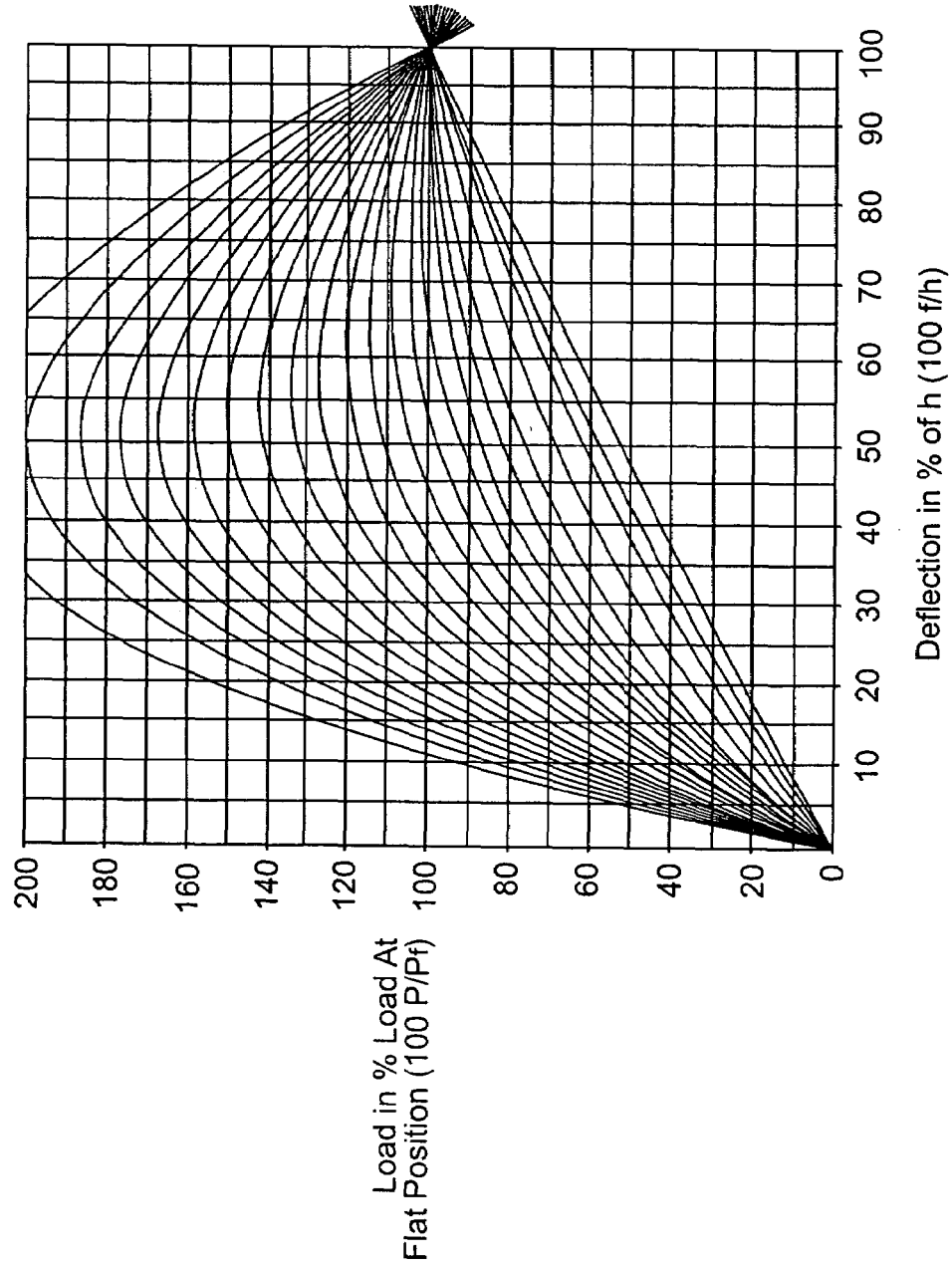
FIG. 14 is a plot illustrating an example of Belleville spring calculation data in accordance with an embodiment of the present invention.

The Belleville spring can be sized between about 1.15 to 1.50 inches in diameter, preferably 1.26 inches, to allow for a full 600 µl delivery. As shown in FIG. 14, a commonly found Belleville spring calculation graph as known to those skilled in the art can be used to calculate an optimum spring geometry. As shown in FIG. 14, multiple plots show load deflection characteristics for Belleville washers of different height-to-thickness ratios. As known to those skilled in the art, a Belleville washer, or Belleville spring, exhibits a load characteristic, shown as a percentage of flat position load deflection, as the spring travels from a flat or flexed state to a relaxed state. As shown in FIG. 14, the selection of a spring having a specific height to thickness ratio can be used to create a desired load deflection profile.

Housing Subassembly

Returning to FIG. 10B, a bottom, or lower housing 210 is provided that can mate with the upper housing 110 and the reservoir subassembly 100 described above. The lower housing 210 can be used to trap and contain all remaining components, and can provide snap features to receive and attach components and housing members. The lower housing 210 can also include one or more guiding features for securing, releasing, and directing the button slide 320 and patient needle manifold 220 as described in greater detail below. A break line between units, such as between the upper and lower housing units, can be positioned toward vertical center of the device, which creates a more stable assembly since the push button subassembly described below can be top down loaded into a substantial housing instead of onto a plate. The upper and lower housings 110 and 210 respectively, can then be snap fit or bonded ultrasonically to one another.

The upper and lower housings 110 and 210 respectively further allow the use of independent subassembly components, where each component can be self contained and stable. For example, the assembled and separate reservoir, specifically the reservoir base surface 120, fill plug 150, septum 160 and reservoir film 170 of the reservoir subassembly 100, contains no unnecessary parts and as a result brings a low particle load into filling operations. In addition, all stored energy components can be contained separate from the reservoir so they cannot be inadvertently deployed during filling Microneedles Returning to FIGS. 10B and 10C, the disclosed device also contains at least one patient needle 222, or microneedle, but may contain several, such as the three microneedles shown in the push button subassembly 300 of FIG. 10C. Each microneedle 222 is preferably at least 31 gauge or smaller, such as 34 gauge, and is anchored within a patient needle manifold 220 which can be placed in fluid communication with the reservoir. Each microneedle is secured to prevent disassembly from the manifold 220 at any force less than 1 pound. The microneedles 222, when more than one is included in the device, may also be of differing lengths, or gauges, or a combination of both differing lengths and gauges, and can contain one or more ports along a body length, preferably located near the tip of the needle or near the tip bevel if the needle has one.

In the embodiment described above, the use of multiple 34 gauge needles to deliver the reservoir contents is practical as the infusion occurs over a longer period than typically associated with an immediate syringe injection requiring a much larger cannula, or needle. In the disclosed embodiments, any microneedle can be used which targets either the intradermal or subcutaneous space; however, the embodiment shown in FIG. 10C includes microneedles of between 1 and 4 mm in exposed length (i.e., 2 mm), and the arrangement of these patient needles can be in a linear or nonlinear array, and can include any number of needles as required by the specific application.

Push Button Subassembly

Figure 10C:
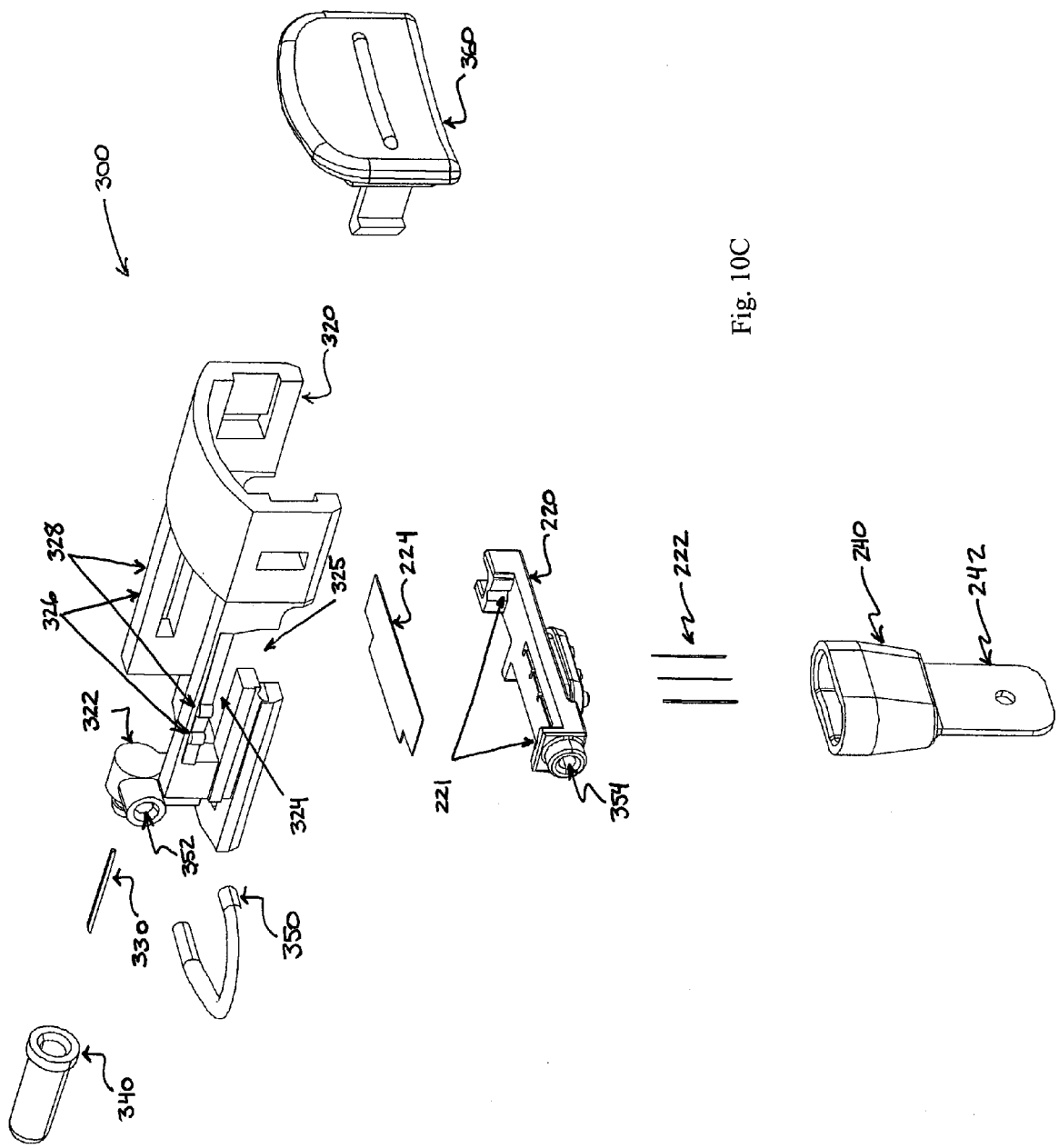
FIG. 10C is an exploded view of a push button subassembly of the first embodiment shown in FIG. 1.

In FIG. 10C, a push button subassembly 300 is shown and integrates a septum needle 330, septum needle manifold 322, and push button slide 320 into one piece; however, fabrication of the push button subassembly 300 can be simplified somewhat by providing a snap-on push button face plate 360 to allow for two or more simpler molded button parts. The push button slide 320 also provides a mechanism to secure the patient needle manifold in a retracted position, and release the manifold when the device is properly activated.

As shown in FIG. 10C, tubing 350 which is used to establish a fluid path as described in greater detail below exits the septum needle manifold 322 on the same side as a tubing entry to the patient needle manifold 220 allowing easier assembly and creating a flexible fluid path between the septum needle manifold and the patient needle manifold. The patient needle manifold 220 containing the patient needles 222 is assembled into tracks 324 provided by the button slide 320 and creates a stable securing and release mechanism, as described in greater detail below.

As shown in FIG. 10C, a pair of detents 326 and 328 can be provided along the tracks 324 to hold the button slide 320 in place at various stages or positions. For example the button subassembly 300 of FIG. 10C provides multiple positions to allow for reservoir loading, patient needle and septum needle manifold assembly, housing welding and user activation. Specifically, at least three positions are provided.

A first position, or assembly position, is provided for reservoir loading and house welding. As the patient needle manifold 220 is held stationary relative to the slidable movement of the button slide 320, the first position is provided wherein the grooves 221 of the patient needle manifold engage the first set of detents 326 of the button slide 320. In this position, loading can occur without interference between the septum boot 340 and the septum 160.

A second position, or ship position, is provided for shipment and establishes the septum needle boot 340 and septum 160 seal. As the patient needle manifold 220 remains stationary relative to the slidable movement of the button slide 320, the second position is provided as the button slide is slidably engaged and the grooves 221 of the patient needle manifold disengage from the first set of detents 326, remaining positioned within the tracks 324, and then engage the second set of detents 328 of the button slide 320. In this position, the septum needle boot 340 engages a recess opening 342 provided by the septum elastomeric plug 160 prior to being pierced by the septum needle 330. This engagement between septum needle boot and the recess opening creates a sterile environment through which the septum needle travels when piercing both the septum needle boot and septum. Therefore at no time is the septum needle 330 exposed to a non-sterile environment, and this effectively eliminates the effects of minor far field welding.

A third position is provided as an activated, or in-use position. As the patient needle manifold 220 remains stationary relative to the slidable movement of the button slide 320, the third position is provided as the button slide is slidably engaged and the grooves 221 of the patient needle manifold disengage from the second set of detents 326, remaining positioned within the tracks 324 until aligned with the track opening 325, then falling free of the button slide 320. In this third position, the septum 160 is penetrated, and the manifold and safety mechanism, both described in greater detail below, are released and forced downward towards the user's skin surface, driven by the spring 310. In the embodiment shown, the force required to penetrate the septum 160, compress the septum needle boot 340 and release the patient needle manifold 220, in moving to this third position is typically between 2 and 4 pounds.

The patient needle and septum needle manifold assemblies 220 and 322 respectively, enable access and discharge of fluid contained within the reservoir and delivery of the fluid to the patient needles 222. Each manifold housing therefore contains a number of fluid flow paths for routing reservoir contents received from the septum needle 330, or other associated protuberance, and any associated tubing 350, and delivering the contents to the patient needles 222 and into the skin of the user. The patient needle manifold 220 in which the patient needles 222 are anchored is in fluid communication with the septum needle manifold 322, in which the septum needle 330 is anchored, by way of a flexible tubing 350.

The patient needle manifold 220 is held in a pre-release, or "up" state, under load, provided by one or more springs 310, by the push button subassembly 300 and lower housing 210. In the first version of securing the patient needle manifold 220 in an up state described above, the patient needle manifold 220 slidably engages a set of tracks 324 disposed on the button slide 320. As the patient needle manifold 220 remains stationary within a chute 212 provided by the lower housing 210, the button slide 320 slidably travels until a track opening 325 aligns with the patient needle manifold 220, releasing the patient needle manifold 220 from the tracks 324 within the chute.

In a second version of securing the patient needle manifold 220 in an up state, one or more protruding blocks (not shown) extend from the button slide 320 and hold the needle manifold 220 in an up state, under load, provided by one or more springs 310. During activation, the button slide 320 is slidably displaced, moving the blocks free of the patient needle manifold 220 which is released and travels toward the skin surface of the user, guided along a travel path by features in the lower housing 210 and the button slide 320. As the blocks move free of the patient needle manifold 220, the manifold drops and the needles 222 seat in the user's skin. Additional details of supporting blocks are further discussed in U.S. patent application Ser. No. 60/420,233, referenced above, the entire content of which is incorporated herein by reference.

In each version described above, one or more drive springs 310 exert a force on the top of the patient needle manifold 220 to drive the manifold when activated, or released from the up state, allowing for patient needle 222 seating when the manifold is released, and creating a fluid path between the septum needle, septum needle manifold, flexible tubing, patient needle manifold and the array of patient needles. The drive springs 310 serve to "plant" the needles into the skin via the spring-loaded patient needle manifold 220 which can travel at a speed ranging between 15 and 26 miles per hour (between 6 and 12 meters per second)

The slidable motion of the button slide 320 also pushes the septum needle 330 through the septum needle boot 340 and the septum 160, creating a flow path between the reservoir and the septum needle. A septum needle containing manifold 322 can be attached or constructed as a component of the button slide 320, and moves with the button slide during activation steps until the septum needle 330 penetrates the septum boot 340, and subsequently the septum 160. Depending upon the sequence desired, prior to, concurrent with, or slightly after the septum needle 330 penetrates the septum 160, the patient needle manifold 220 is released and bottoms out against the skin surface, seating the patient needles 222 and thereby initiating flow of energized fluid from the reservoir, through the septum needle and septum needle manifold, through the flexible tubing attached to the septum needle manifold, and to the patient needles of the patient needle manifold.

One or more septum needles 330 can be provided, separate from the patient microneedles 222, allowing greater flow within the complete fluid path between reservoir and patient needles. In the embodiment described above, the complete fluid path includes in part, two or more needles, specifically, at least one septum needle 330, and at least one patient microneedle 222. This allows the device to incorporate needles of different constructions depending upon the fluid path characteristics desired. For example, the patient microneedles 222 can include one or more 34 gauge needles, where the septum needle 330 can include one or more equal or larger needles as required. Additionally, the separation of the patient and septum needles allows further freedom of movement of the patient needles during operation of the device.

A flexible tube 350 can be used to connect the septum needle 330 and/or septum needle manifold 322 to the patient needle manifold 220. The flexible nature of the tube coupling allows the patient needle manifold 220 to move with greater independence from the remaining components of the device, allowing more effective needle seating. Once properly seated, the patient needle manifold 220 completes the fluid path between the flexible tubing 350 and the array of patient microneedles 222, and the user's skin. As noted above, the patient needle manifold 220 is guided into position by features in the lower housing 210, and the drive springs 310 described above exert a force on top of the patient needle manifold 220 allowing for needle seating when the manifold is released. A variety of drive spring options exist, including the use of as few as one or as many as four coil springs, or one or more leaf springs.

Figure 15A:
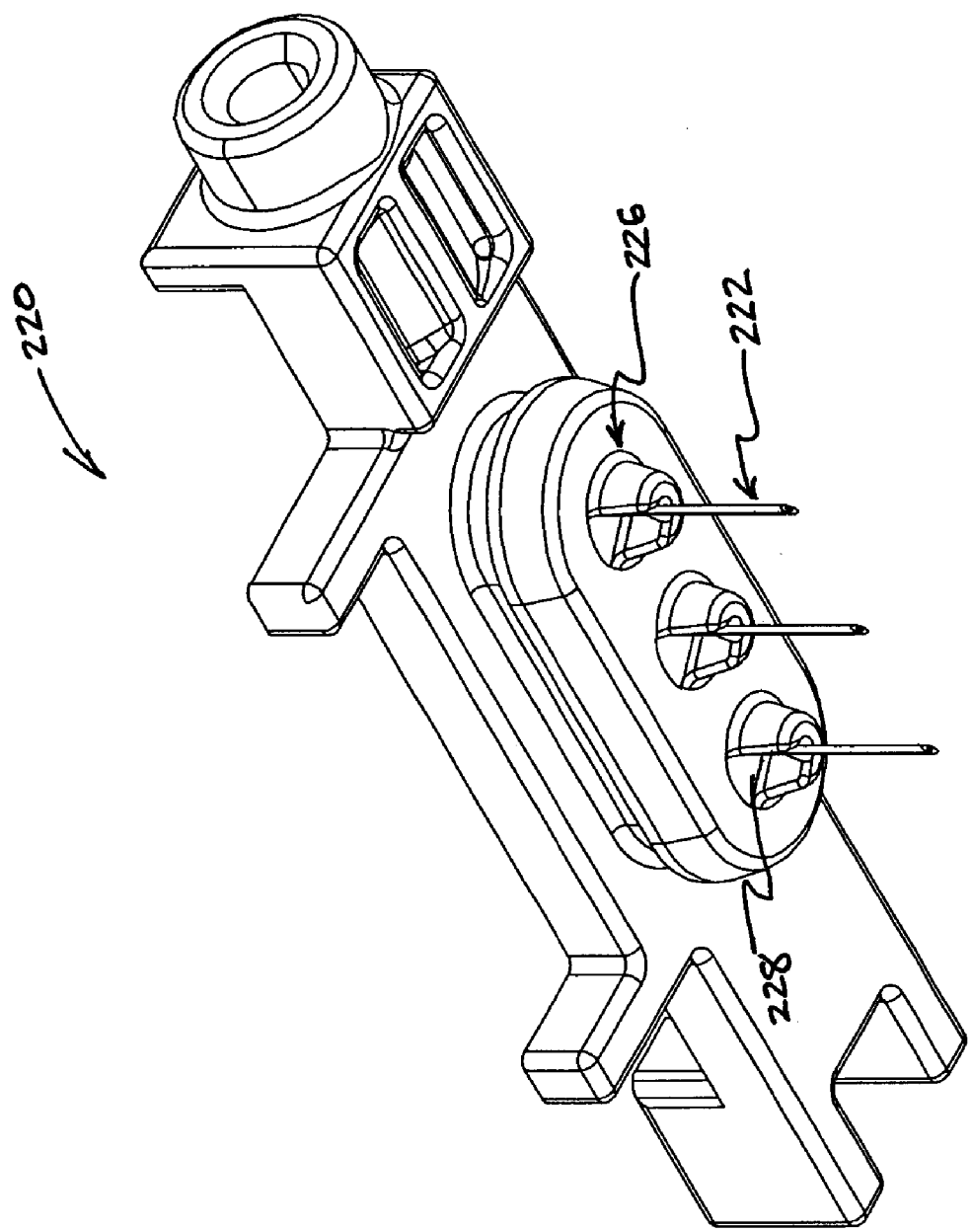
FIG. 15A is a perspective view of a preferred embodiment of the patient needle manifold patient contact surface configuration for the patient needle manifold.
Figure 15B:
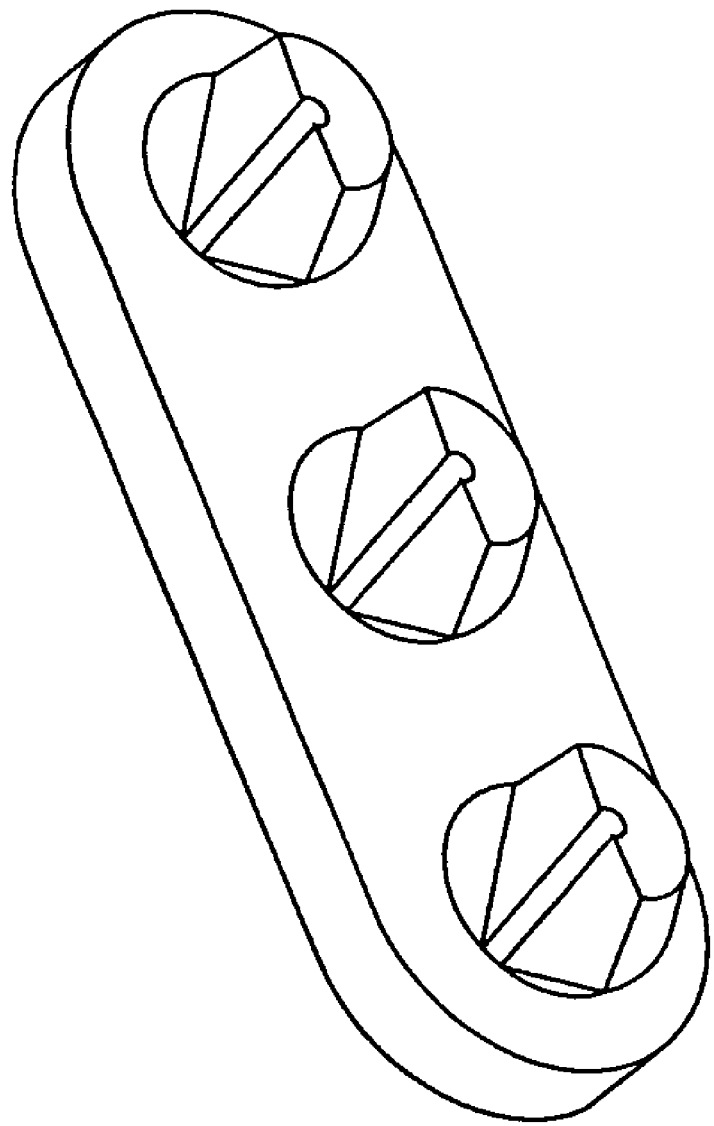
FIG. 15B is a perspective view of another patient contact surface configuration for the patient needle manifold of FIG. 15A.

A detailed embodiment of the patient needle manifold 220 is shown in FIGS. 15A and 15B. FIG. 15A is a perspective view of a preferred embodiment of the patient needle manifold patient contact surface configuration for the patient needle manifold 220, and FIG. 15B is a perspective view of second patient contact surface configuration. Additional details of manifolds are disclosed in a commonly-assigned U.S. patent application of Alex Lastovich et al., Ser. No. 10/357,502, filed on Feb. 4, 2003 and entitled "Device And Method For Delivering Or Withdrawing A Substance Through The Skin", the entire content of which is incorporated herein by reference and in U.S. patent application Ser. No. 60/447,359, Ser. No. 60/450,680, and Ser. No. 60/450,681, referenced above, the entire contents of each being incorporated herein by reference.

In the patient needle manifold embodiment shown in FIGS. 10C and 15, at least one fluid communication path, or feed channel, is provided to each patient needle 222. The manifold may simply have a single path to one or more patient needles, or may provide multiple fluid paths or channels routing contents to each needle separately. These paths or channels may further comprise a tortuous path for the contents to travel, thereby affecting fluid pressures and rates of delivery, and acting as a flow restrictor. The channels or paths within the patient needle manifold 220 can range in width, depth and configuration depending upon application, where channel widths are typically between about 0.015 and 0.04 inch, preferably 0.02 inch, and are constructed to minimize dead space within the manifold. As further shown in FIG. 1C, the patient needle manifold 220 can also include a film lid 224, comprised of materials outlined in Table 1, to seal the manifold and exposed manifold channels. As with the fluid path analysis above and outlined in Table 1, the film lid 224 material is also chosen to be fully compatible with the contents of the device, and provide minimal extractables resulting in fewer particulates. In yet other embodiments of the patient needle manifold, the manifold can be non-film sealed, such as where the manifold includes enclosed channels within the manifold body.

The skin contact surface of the patient needle manifold 220 shown in FIG. 15A shows a skin contact surface having a plurality of exposed needles, with each needle extending from a needle cone 226. Each needle cone 226 can include, or be placed adjacent to one or more glue wells 228 provided to allow attachment between the patient needle 222 and the patient needle manifold 220. As illustrated in FIG. 15A, each patient needle cone 226 is preferably not uniform about the entire cone circumference and can include a removed portion of the needle cone of variable size and depth. Such a segment or cut-out section of the patient needle cone 226 can be removed to create a glue well 228, or provide laser weld access, to secure each needle within the needle cone at the required height with minimal intrusion into the flow paths of the manifold.

A second version of the skin contact surface of the patient needle manifold 220 is shown in FIG. 15B (contact surface shown only). The needle cones of FIG. 15B include a removed cone section both above and below the patient contact surface, positioned as described for the version in FIG. 15A. However, in the version shown in FIG. 15B, a tapered recess is also provided extending below the removed portion of the patient needle cone, adjacent to the needle opening. Therefore, as shown in FIG. 15A, the removed portion can be merely a removed segment of the cone circumference above the patient contact surface, or as shown in FIG. 15B, a larger segment of the cone circumference can be removed, which is then further extended into the manifold surface to provide a more extensive glue well.

The removed portion and adjacent recess described above can be used to aid in front gluing the patient needles 222 within the patient needle manifold 220 during manufacture, and can facilitate other types of fixing such as laser welding. Such a front glue method allows a reduction in height of the chamber within the manifold in which the blunt end of the needle 222 is positioned, and further prevents glue from depositing in and around the fluid path within the manifold. The undesired introduction of glue into these fluid paths can create problems in glue/drug interactions, as well as creating unknown or variable dead volumes within the patient needle manifold 220 itself. The use of front gluing further provides a greater degree of repeatability, allowing accurate calculations of any minor glue-caused dead volumes that do occur. However, such glue positioning upon the patient contact surfaces shown in FIGS. 15A and 15B should preferably be carefully monitored to prevent glue domes about the needle bases, which can reduce exposed needle length.

Figure 16A:
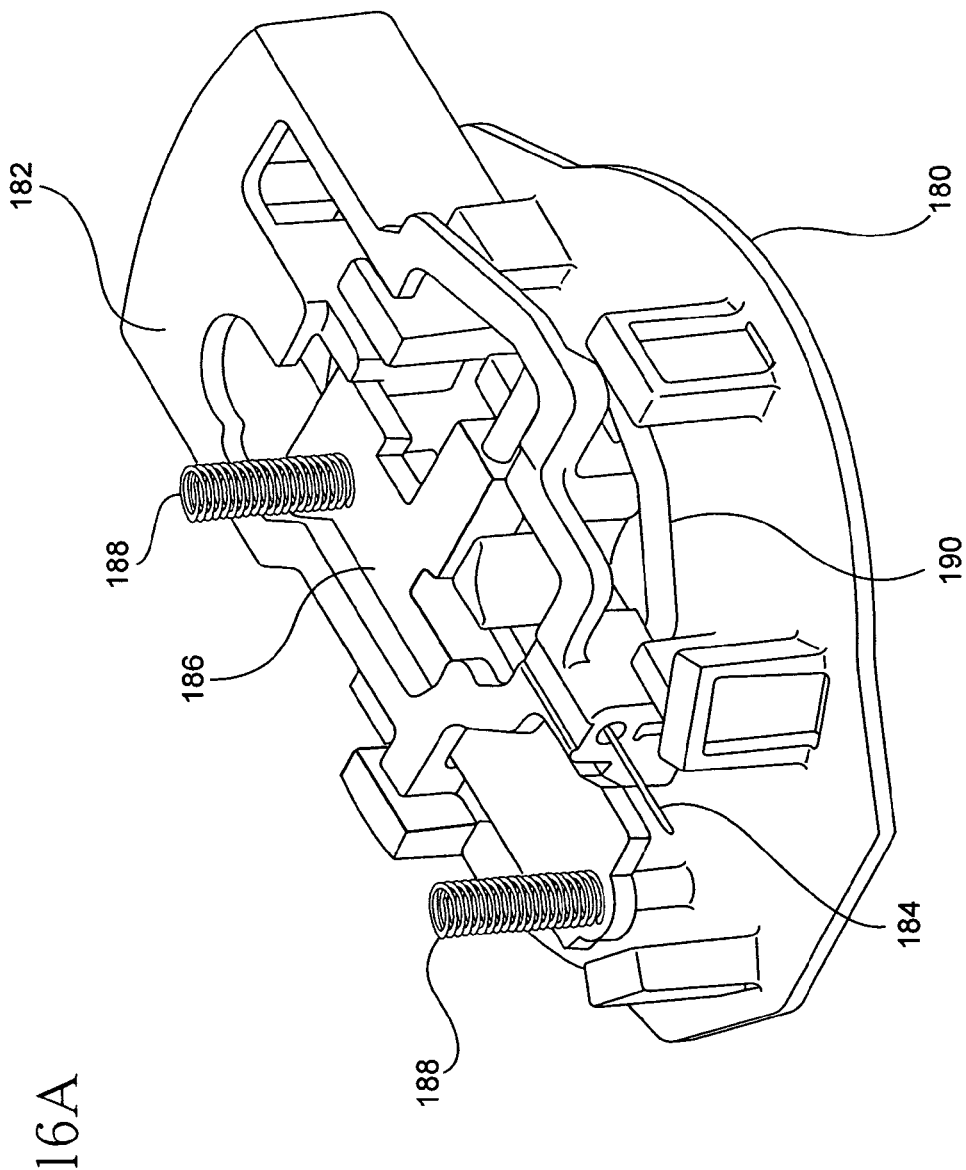
FIG. 16A is a top perspective view of another embodiment of the subassemblies of FIGS. 10A through 10C partially assembled.
Figure 16B:
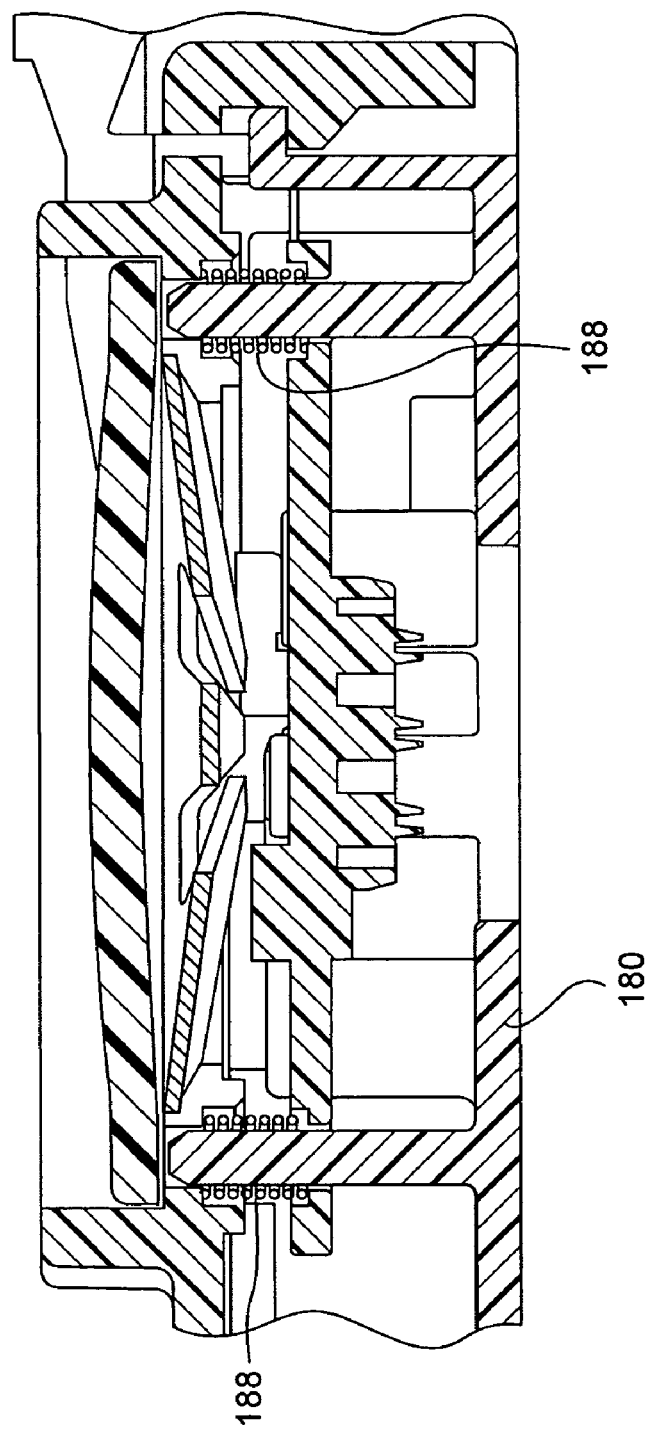
FIG. 16B is a cross-sectional view of the subassemblies shown in FIG. 16A prior to energizing and activation.
Figure 16C:
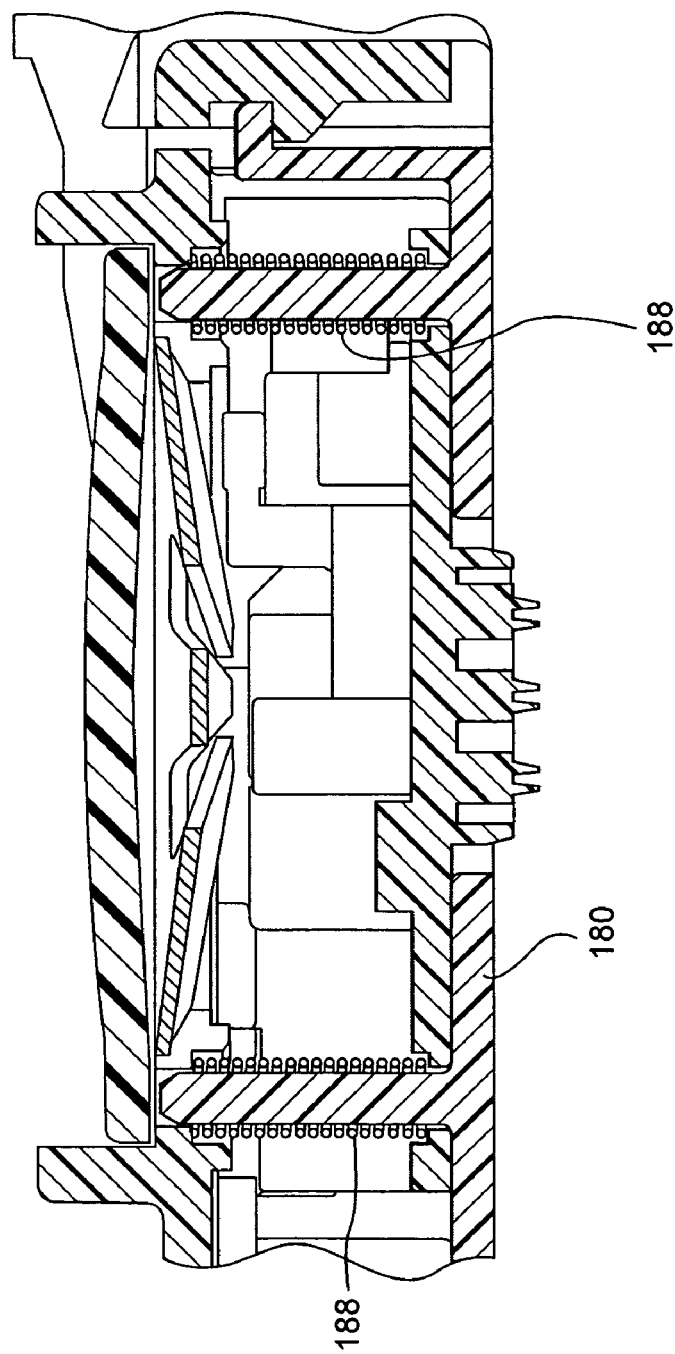
FIG. 16C is a cross-sectional view of the subassemblies shown in FIG. 16A after energizing and activation.

The subassembly embodiments presented above are not restrictive, and can be reconfigured as required in a given application. For example, another embodiment of the subassemblies described above are shown in FIGS. 16A through 16B. FIG. 16A is a top perspective view of another embodiment of the subassemblies of FIGS. 10A through 10C partially assembled, and FIGS. 16B and 16C are cross-sectionals view of the subassemblies shown in FIG. 16A prior to, and after energizing and activation, respectively. As shown in FIG. 16A, the lower housing 180 can be configured to slidably receive a one piece push button slide 182 having a septum needle 184 similar to the button slide assembly 320 described above. A wider patient needle manifold 186 having at least one patient needle (not shown) can also be included, extending parallel to the button slide travel and including a first and second drive spring 188. In the subassembly embodiment shown in FIG. 16A, the septum needle 184 and patient needle manifold remain in fluid communication via a flexible tubing 190 substantially as described above, allowing the patient needle manifold to travel free of restrictions once released, as shown in FIG. 16C.

The engagement of the button slide assembly 320 within the lower housing 180 in the embodiment shown in FIGS. 16A through 16C further provides an overall lower device profile, in addition to improving handling and manufacturing requirements. The flexible tubing 190 is more readily conformed in this embodiment, and allows a more simplified push button slide.

Operation

The device described above is suitable for use in administering various substances, including medications and pharmaceutical agents, to a patient, and particularly to a human patient. As used herein, a pharmaceutical agent includes a substance having biological activity that can be delivered through the body membranes and surfaces, and particularly the skin. Examples, listed in greater detail below, include antibiotics, antiviral agents, analgesics, anesthetics, anorexics, antiarthritics, antidepressants, antihistamines, anti-inflammatory agents, antineoplastic agents, vaccines, including DNA vaccines, and the like. Other substances that can be delivered intradermally or subcutaneously to a patient include human growth hormone, insulin, proteins, peptides and fragments thereof. The proteins and peptides can be naturally occurring, synthesized or recombinantly produced. Additionally, the device can be used in cell therapy, as during intradermal infusion of dendritic cells.

Still other substances which can be delivered in accordance with the present invention are drugs, vaccines and the like used in the prevention, diagnosis, alleviation, treatment, or cure of disease, with the drugs including Alpha-1 antitrypsin, Anti-Angiogenesis agents, Antisense, butorphanol, Calcitonin and analogs, Ceredase, COX-II inhibitors, dermatological agents, dihydroergotamine, Dopamine agonists and antagonists, Enkephalins and other opioid peptides, Epidermal growth factors, Erythropoietin and analogs, Follicle stimulating hormone, G-CSF, Glucagon, GM-CSF, granisetron, Growth hormone and analogs (including growth hormone releasing hormone), Growth hormone antagonists, Hirudin and Hirudin analogs such as hirulog, IgE suppressors, Insulin, insulinotropin and analogs, Insulin-like growth factors, Interferons, Interleukins, Leutenizing hormone, Leutenizing hormone releasing hormone and analogs, Low molecular weight heparin, M-CSF, metoclopramide, Midazolam, Monoclonal antibodies, Narcotic analgesics, nicotine, Non-steroid anti-inflammatory agents, Oligosaccharides, ondansetron, Parathyroid hormone and analogs, Parathyroid hormone antagonists, Prostaglandin antagonists, Prostaglandins, Recombinant soluble receptors, scopolamine, Serotonin agonists and antagonists, Sildenafil, Terbutaline, Thrombolytics, Tissue plasminogen activators, TNF—, and TNF—antagonist, the vaccines, with or without carriers/adjuvants, including prophylactics and therapeutic antigens (including but not limited to subunit protein, peptide and polysaccharide, polysaccharide conjugates, toxoids, genetic based vaccines, live attenuated, reassortant, inactivated, whole cells, viral and bacterial vectors) in connection with, addiction, arthritis, cholera, cocaine addiction, diphtheria, tetanus, HIB, Lyme disease, meningococcus, measles, mumps, rubella, varicella, yellow fever, Respiratory syncytial virus, tick borne japanese encephalitis, pneumococcus, streptococcus, typhoid, influenza, hepatitis, including hepatitis A, B, C and E, otitis media, rabies, polio, HIV, parainfluenza, rotavirus, Epstein Barr Virus, CMV, chlamydia, non-typeable haemophilus, moraxella catarrhalis, human papilloma virus, tuberculosis including BCG, gonorrhoea, asthma, atherosclerosis malaria, E-coli, Alzheimers, H. Pylori, salmonella, diabetes, cancer, herpes simplex, human papilloma and the like other substances including all of the major therapeutics such as agents for the common cold, Anti-addiction, anti-allergy, anti-emetics, anti-obesity, antiosteoporeteic, anti-infectives, analgesics, anesthetics, anorexics, antiarthritics, antiasthmatic agents, anticonvulsants, anti-depressants, antidiabetic agents, antihistamines, anti-inflammatory agents, antimigraine preparations, antimotion sickness preparations, antinauseants, antineoplastics, antiparkinsonism drugs, antipruritics, antipsychotics, antipyretics, anticholinergics, benzodiazepine antagonists, vasodilators, including general, coronary, peripheral and cerebral, bone stimulating agents, central nervous system stimulants, hormones, hypnotics, immunosuppressives, muscle relaxants, parasympatholytics, parasympathomimetrics, prostaglandins, proteins, peptides, polypeptides and other macromolecules, psychostimulants, sedatives, sexual hypofunction and tranquilizers and major diagnostics such as tuberculin and other hypersensitivity agents as described in U.S. Pat. No. 6,569,143, entitled "Method Of Intradermally Injecting Substances", the entire content of which is incorporated herein by reference.

Vaccine formulations which can be delivered in accordance with the present invention can be selected from the group consisting of an antigen or antigenic composition capable of eliciting an immune response against a human pathogen, which antigen or antigenic composition is derived from HIV-1, (such as tat, nef, gp120 or gp160), human herpes viruses (HSV), such as gD or derivatives thereof or Immediate Early protein such as ICP27 from HSVI or HSV2, cytomegalovirus (CMV (esp Human) (such as gB or derivatives thereof), Rotavirus (including live-attenuated viruses), Epstein Barr virus (such as gp350 or derivatives thereof), Varicella Zoster Virus (VZV, such as gp1, II and IE63) or from a hepatitis virus such as hepatitis B virus (for example Hepatitis B Surface antigen or a derivative thereof), hepatitis A virus (HAV), hepatitis C virus and hepatitis E virus, or from other viral pathogens, such as paramyxoviruses: Respiratory Syncytial virus (RSV, such as F and G proteins or derivatives thereof), parainfluenza virus, measles virus, mumps virus, human papilloma viruses (HPV for example HPV6, 11, 16, 18), flaviviruses (e.g. Yellow Fever Virus, Dengue Virus, Tick-borne encephalitis virus, Japanese Encephalitis Virus) or Influenza virus (whole live or inactivated virus, split influenza virus, grown in eggs or MDCK cells, or whole flu virosomes or purified or recombinant proteins thereof, such as HA, NP, NA, or M proteins, or combinations thereof), or derived from bacterial pathogens such as *Neisseria* spp, including *N. gonorrhea* and *N. meningitidis* (for example capsular polysaccharides and conjugates thereof, transferrin-binding proteins, lactoferrin binding proteins, PilC, adhesins); *S. pyogenes* (for example M proteins or fragments thereof, C5A protease, lipoteichoic acids), *S. agalactiae, S. mutans H. ducreyi; Moraxella* spp, including *M catarrhalis*, also known as *Branhamella catarrhalis* (for example high and low molecular weight adhesins and invasins); *Bordetella* spp, including *B. pertussis* (for example pertactin, pertussis toxin or derivatives thereof, filamenteous hemagglutinin, adenylate cyclase, fimbriae), *B. parapertussis* and *B. bronchiseptica; Mycobacterium* spp., including *M. tuberculosis* (for example ESAT6, Antigen 85A, -B or-C), *M. bovis, M. leprae, M. avium, M. paratuberculosis M. smegmatis; Legionella* spp, including *L. pneumophila; Escherichia* spp, including enterotoxic *E. coli* (for example colonization factors, heat-labile toxin or derivatives thereof, heat-stable toxin or derivatives thereof), enterohemorragic *E. coli*, enteropathogenic *E. coli* (for example shiga toxin-like toxin or derivatives thereof); *Vibrio* spp, including *V. cholera* (for example cholera toxin or derivatives thereof); *Shigella* spp, including *S. sonnei, S. dysenteriae, S. flexnerii; Yersinia* spp, including *Y. enterocolitica* (for example a Yop protein), *Y. pestis, Y. pseudotuberculosis; Campylobacter* spp, including *C. jejuni* (for example toxins, adhesins and invasins) and *C. coli; Salmonella* spp, including *S. typhi, S. paratyphi, S. choleraesuis, S. enteritidis; Listeria* spp., including *L. monocytogenes; Helicobacter* spp, including *H. pylori* (for example urease, catalase, vacuolating toxin); *Pseudomonas* spp, including *P. aeruginosa; Staphylococcus* spp., including *S. aureus, S. Epidermidis; Enterococcus* spp., including *E. faecalis, E. faecium; Clostridium* spp., including *C. tetani* (for example tetanus toxin and derivative thereof), *C. botulinum* (for example Botulinum toxin and derivative thereof), *C. difficile* (for example clostridium toxins A or B and derivatives thereof) *Bacillus* spp., including *B. anthracis* (for example botulinum toxin and derivatives thereof); *Corynebacterium* spp., including *C. diphtheriae* (for example diphtheria toxin and derivatives thereof); *Borrelia* spp., including *B. Burgdorferi* (for example OspA, OspC, DbpA, DbpB), *B. garinii* (for example OspA, OspC, DbpA, DbpB), *B. afzelii* (for example OspA, OspC, DbpA, DbpB), *B. andersonii* (for example OspA, OspC, DbpA, DbpB), *B. Hermsii; Ehrlichia* spp., including *E. equi* and the agent of the Human Granulocytic Ehrlichiosis; *Rickettsia* spp, including *R. rickettsii; Chlamydia* spp., including *C. Trachomatis* (for example MOMP, heparin-binding proteins), *C. pneumoniae* (for example MOMP, heparin-binding proteins), *C. psittaci; Leptospira* spp., including *L. interrogans; Treponema* spp., including *T. pallidum* (for example the rare outer membrane proteins), *T. denticola, T. hyodysenteriae*; or derived from parasites such as *Plasmodium* spp., including *P. Falciparum; Toxoplasma* spp., including *T. gondii* (for example SAG2, SAG3, Tg34); *Entamoeba* spp., including *E. histolytica; Babesia* spp., including *B. microti; Trypanosoma* spp., including *T. cruzi; Giardia* spp., including *G. lamblia; Leshmania* spp., including *L. major; Pneumocystis* spp., including *P. Carinii; Trichomonas* spp., including *T. vaginalis; Schisostoma* spp., including *S. mansoni*, or derived from yeast such as *Candida* spp., including *C. albicans; Cryptococcus* spp., including *C. neoformans*, as described in PCT Patent Publication No. WO 02/083214, entitled "Vaccine Delivery System", the entire content of which is incorporated herein by reference.

These also include other preferred specific antigens for *M. tuberculosis*, for example Tb Ra12, Th H9, Tb Ra35, Tb38-1, Erd 14, DPV, MTI, MSL, mTTC2 and hTCC1. Proteins for *M. tuberculosis* also include fusion proteins and variants thereof where at least two, preferably three polypeptides of *M. tuberculosis* are fused into a larger protein. Preferred fusions include Ral2-TbH9-Ra35, Erd14-DPV-MTI, DPV-MTI-MSL, Erd14-DPV-MTI-MSL-mTCC2, Erd14-DPV-MTI-MSL, DPV-MTI-MSL-mTCC2, TbH9-DPV-MTI. Most preferred antigens for Chlamydia include for example the High Molecular Weight Protein (HWMP), ORF3, and putative membrane proteins (Pmps). Preferred bacterial vaccines comprise antigens derived from *Streptococcus* spp, including *S. pneumoniae* (for example capsular polysaccharides and conjugates thereof, PsaA, PspA, streptolysin, choline-binding proteins) and the protein antigen Pneumolysin (Biochem Biophys Acta, 1989,67,1007; Rubins et al., Microbial Pathogenesis, 25,337-342), and mutant detoxified derivatives thereof. Other preferred bacterial vaccines comprise antigens derived from *Haemophilus* spp., including *H. influenzae* type B ("Hib", for example PRP and conjugates thereof), non typeable *H. influenzae*, for example OMP26, high molecular weight adhesins, P5, P6, protein D and lipoprotein D, and fimbrin and fimbrin derived peptides or multiple copy variants or fusion proteins thereof. Derivatives of Hepatitis B Surface antigen are well known in the art and include, inter alia, PreS1, PreS2 S antigens. In one preferred aspect the vaccine formulation of the invention comprises the HIV-1 antigen, gp120, especially when expressed in CHO cells. In a further embodiment, the vaccine formulation of the invention comprises gD2t as hereinabove defined.

In addition to the delivery of substances listed above, the device and method can also be used for withdrawing a substance from a patient, or monitoring a level of a substance in the patient. Examples of substances that can be monitored or withdrawn include blood, intersitial fluid or plasma. The withdrawn substances may then be analyzed for analytes, glucose, drugs and the like.

Figure 11A:
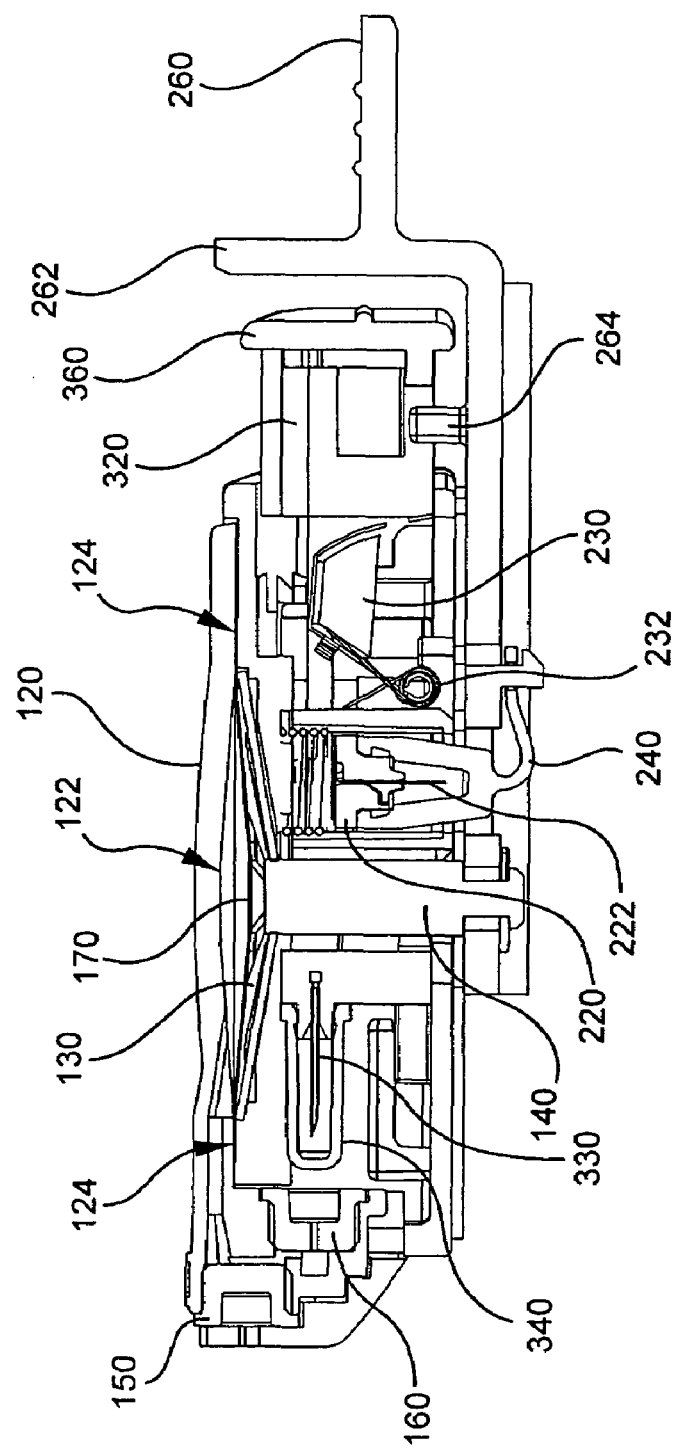
FIG. 11A is a cross-sectional view (6-6 in FIG. 1) of the first embodiment shown in FIG. 1 prior to energizing and activation.
Figure 11B:
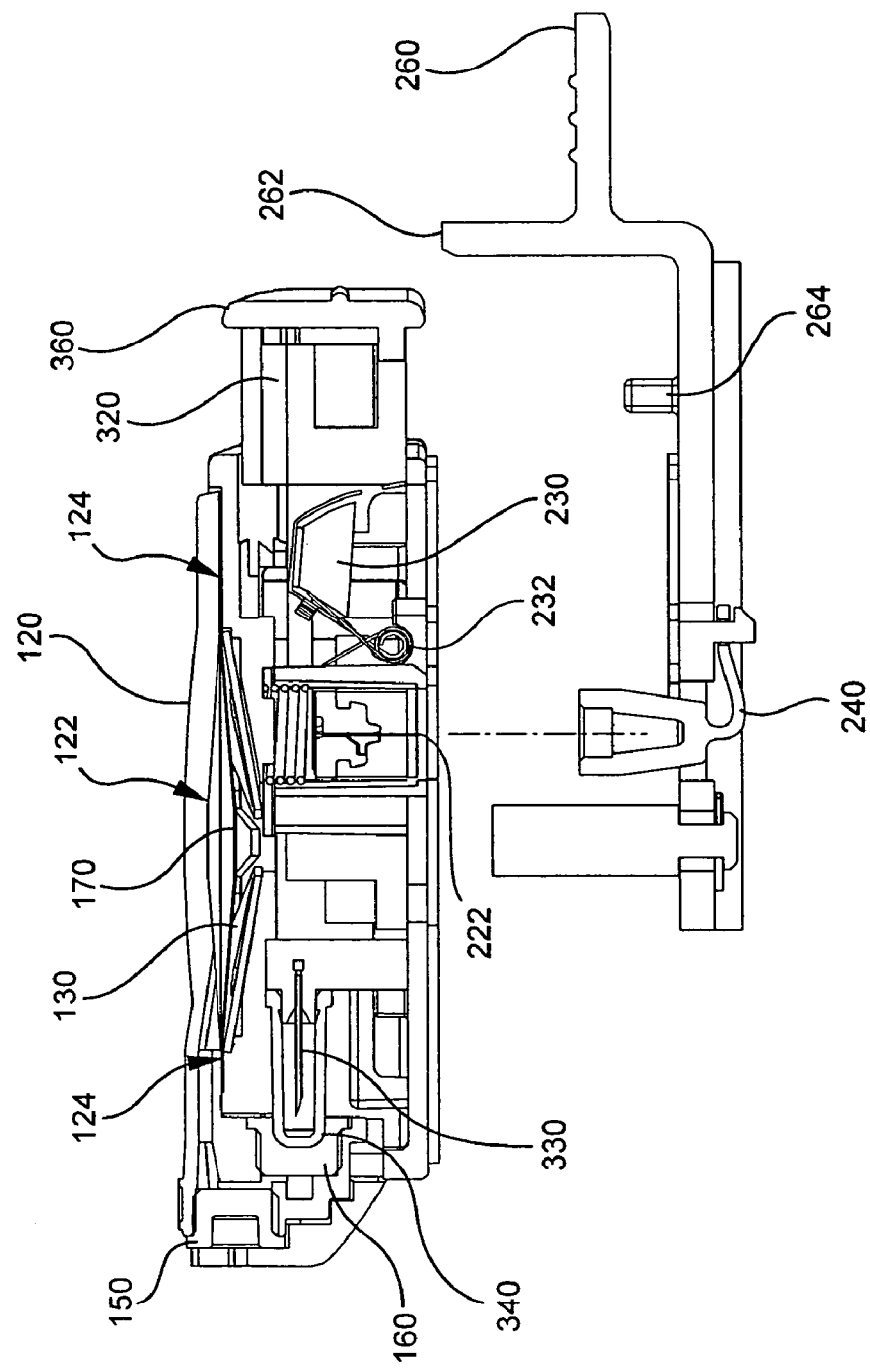
FIG. 11B is a cross-sectional view (6-6 in FIG. 1) of the first embodiment shown in FIG. 1 after energizing and prior to activation.
Figure 11C:
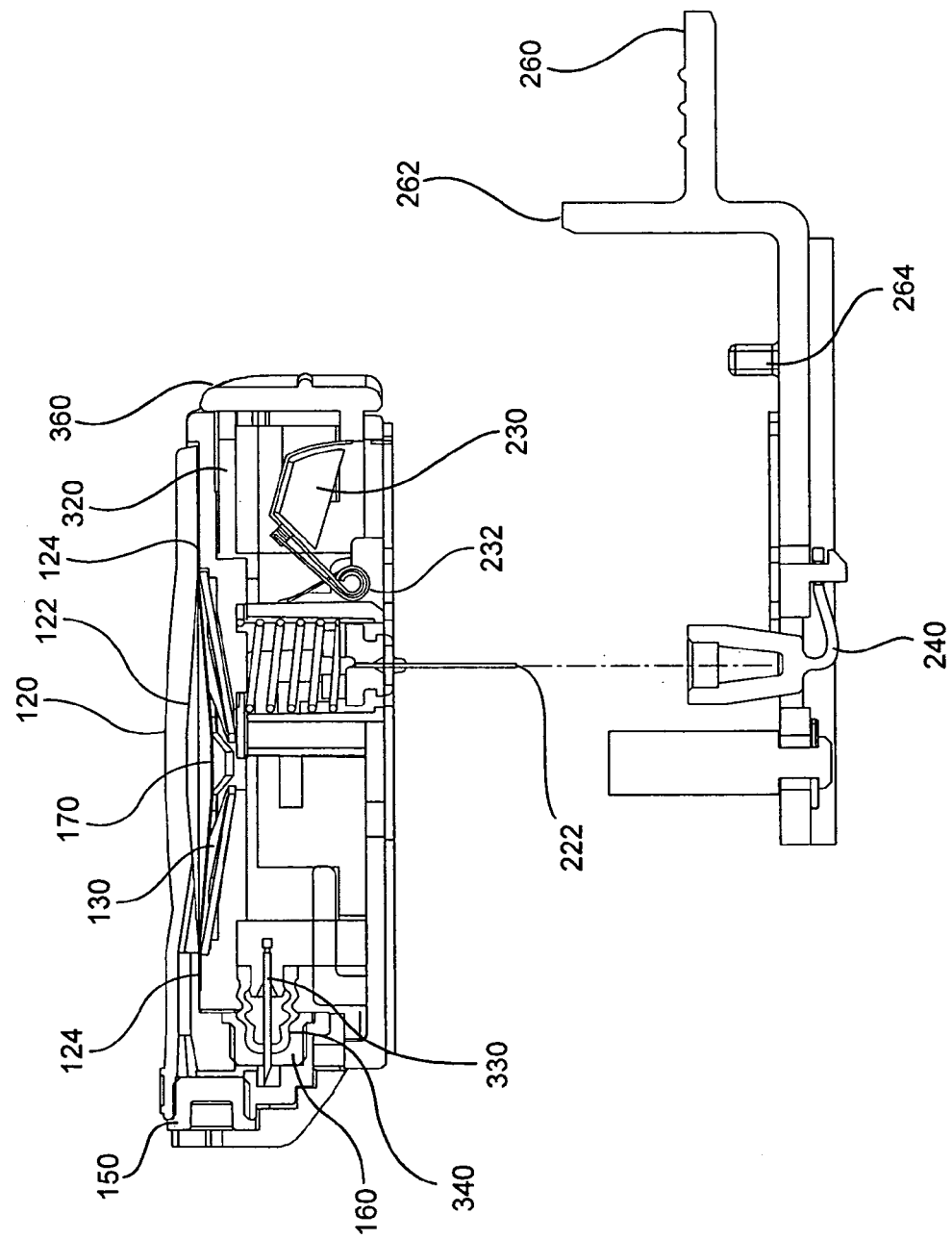
FIG. 11C is a cross-sectional view (6-6 in FIG. 1) of the first embodiment shown in FIG. 1 after activation.

The embodiment of the present invention described above is a push-button design wherein the device is first energized, then positioned and affixed to a skin surface, and activated by gently pressing a slide button as shown in FIGS. 11A through 11C. FIG. 11A is a cross-sectional view (6-6 in FIG. 1) of the first embodiment shown in FIG. 1 prior to energizing and activation. FIG. 1B is a cross-sectional view of the first embodiment shown after energizing and prior to activation, and FIG. 11C is a cross-sectional view of the first embodiment after activation.

Specifically, as shown in FIGS. 11A and 11B, the user first removes the device of FIG. 11A from a sterile packaging and energizes the system prior to adhering the device to the skin by removing the pull handle 260 from the bottom surface of the device as shown in FIG. 11B, in a motion similar to opening a soda can or peeling open an orange. The pull handle 260 is positioned and extends to one side of the device thereby creating a mechanical advantage for the removal of the pull handle and attached retaining pin 140, which can be removed with no more than a reasonable amount of force that can be exerted by a wide range of users (i.e. typically less than 3 pounds).

As shown in FIG. 11B, the removal of the pull handle 260 removes the retaining pin 140, and can also simultaneously remove an adhesive cover (not shown) and/or a needle cap 240, as described in greater detail below. In yet another version of this embodiment, the pull handle 260 can be incorporated with the product packaging, such that when the package is opened and the device is removed, the retaining pin 140, adhesive cover and/or the needle cap 240 is also removed.

Upon removal of the device from the package and prior to use, the features described above allows the user to then inspect both the device and the contents therein, including inspection for missing or damaged components, expiration dates(s), hazy or color-shifted drugs, and so forth. After use, the user can once again inspect the device to ensure the entire dose was delivered. In this regard, the device can include an administered dose indicator for example, a readable gauge area that is at least 20% of the surface area of the device housing and accurate to within +/−10% of the labeled dose.

Once the retaining pin 140 has been pulled a sufficient distance from the device to disengage from the spring, the fingers of the Belleville spring 130 are released and are free to drop against the reservoir film 170 within the device. The activation button 360 and button slide 320 of the button subassembly 300 can be either interlocked with, and/or shielded by the pull handle 260, such that the activation button 360 cannot be pushed until the pull handle 260 has been removed, thus preventing inadvertent activation or incorrect order of operation by the user. Once removal of the pull handle 260, retaining pin 140, adhesive cover and needle cap 240 is accomplished as shown in FIG. 11B, the device is energized and ready for positioning and activation. This energizing step releases the Belleville spring 130 allowing it to press against the flexible film 170 of the reservoir subassembly 100, pressurizing the reservoir and the substance communication path up to the septum 160, and prepares the device for activation.

The next step is the positioning and application of the device to the user's skin surface. Like a patch, the user firmly presses the device onto the skin and the lower housing 210 includes a bottom surface that allows for the adhesive layer 250 to secure the device to the skin of the user. This bottom surface of the lower housing 210 can be flat, contoured, or shaped in any suitable fashion, and includes an adhesive layer 250 thereon, which would most likely be covered prior to shipping. Prior to use, the user peels back the adhesive covering, such as a film covering the adhesive, thereby exposing the adhesive for placement against the skin. The adhesive should preferably adhere to the bottom surface of the device with a peel force of not less than 2 pounds, and include a covering that should preferably release from the adhesive with a peel force of less than ½ pound. Once removed, the user is then able to place the device against the skin and press to ensure proper adhesion (i.e. application of a vertical load of 3 pounds). In versions of the embodiment in which a removable needle cover 240 is provided, the needle cover should preferably remove from the device with a force not to exceed 2 pounds.

Once properly positioned, the device is activated by sliding the button 360 and attached button slide 320 of the push button subassembly 300 towards the center of the device as shown in FIG. 11C. With no more than a reasonable amount of force applied by the user (i.e. between 2 and 4 pounds), the activation button can be depressed completely to allow activation. The button and button slide extends within the device and includes at least one slot which, in a non-release position, holds the patient needle manifold 220 up against the compressive force of one or more driving springs 310.

As the button is pushed by the user, the first event to occur is the button pushing the septum needle 330 through the septum needle boot 340, and then through the septum 160, creating a flow path between the reservoir and the patient needles. As noted above, the "shipping" position has already brought the septum boot and septum into contact. Further motion of the button then releases the patient needle manifold 220 as described above, allowing the patient needles 222 to seat into the skin of the patient driven by the force of one or more driving springs 310. At this point, the button 360 and button slide 320 locks into place giving a positive audible and tactile feedback to the user indicating that infusion has begun.

The button subassembly 300 sequence of operation described above can be varied in other embodiments of the same or similar device. In one such embodiment for example, as the button is pushed by the user, the first event to occur is the patient needle manifold 220 releasing and allowing the patient needles 222 to seat into the skin of the patient driven by the force of the driving springs 310. Further motion of the button then pushes the septum needle 330 through the septum needle boot 340 and septum 160 to create a fluid path. Either method can be implemented, but failure modes of each can be different. For example, in an operation sequence in which flow is initiated before the patient needle manifold is released, if the patient needles fail to seat properly a wet injection will typically occur.

The flexible tubing 350 in each embodiment connects the septum needle 330 or septum needle manifold 322 now in fluid communication with the reservoir, to the patient needle manifold 220 now in fluid communication with the user, and is sufficiently flexible to allow the patient needle manifold to move independently of any other device component. In addition, as with the tortuous path established by the patient needle manifold channels described above, the tubing 350 can also serve as a flow restriction where required.

Once activated, the user typically leaves the device in position, or "wears" the device, for some period of time, such as ten minutes to seventy-two hours for complete delivery of the device contents, and then removes and discards the device with no damage to the underlying tissue. However, upon intentional or accidental removal, one or more safety features can deploy as described in greater detail below to shield the exposed needles resulting from activation. The safety features however can be configured to not deploy if the button and button slide has not been pushed and the patient needles extended.

Safety Features

To prevent inadvertent or accidental needle sticks, intentional re-use of the device, and to shield exposed needles, a locking needle safety mechanism can be provided and activated automatically immediately upon removal of the device from the skin surface.

Figure 17A:
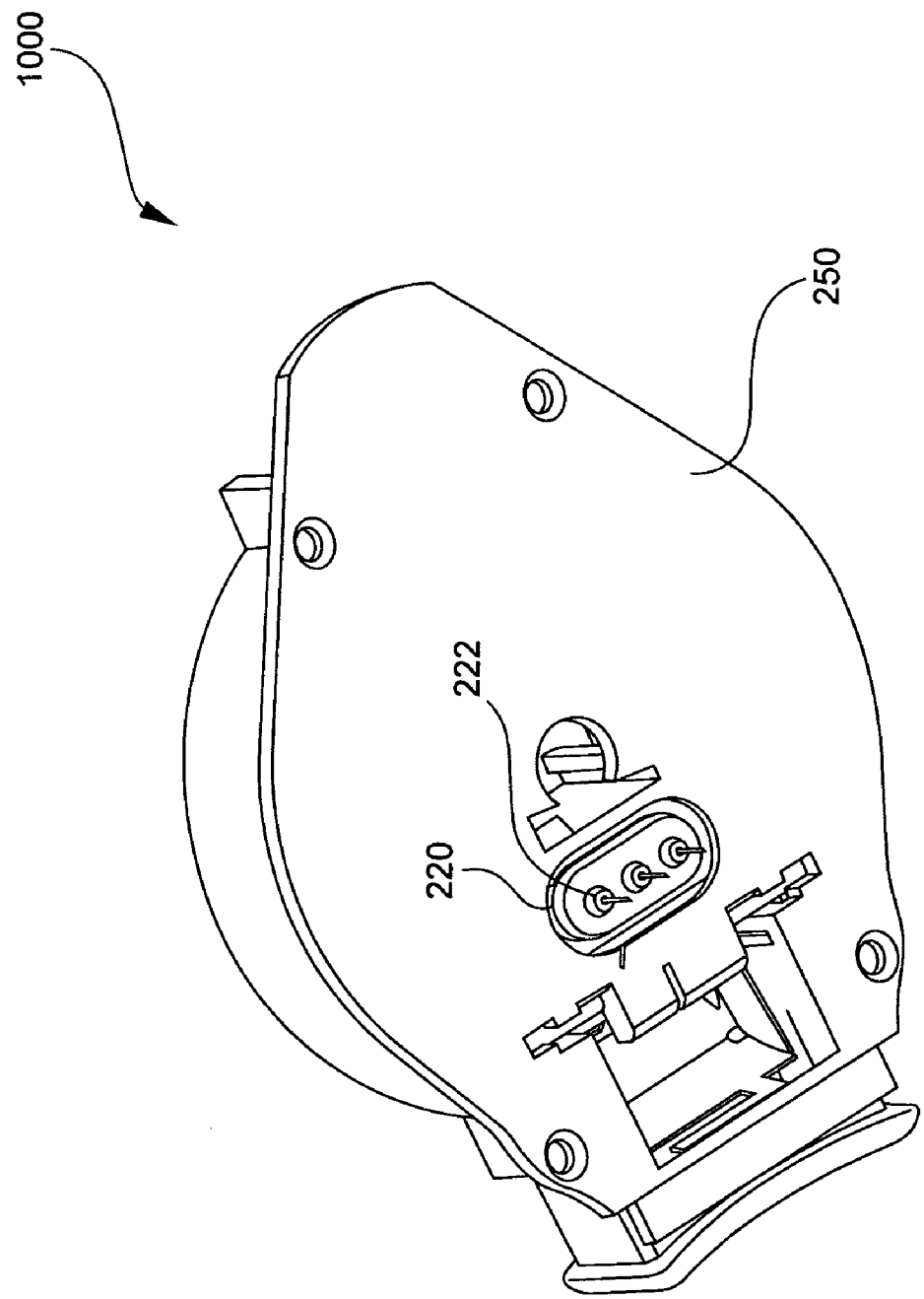
FIG. 17A is a perspective view of a rotating safety shield feature of an embodiment of the present invention prior to energizing and activation.
Figure 17B:
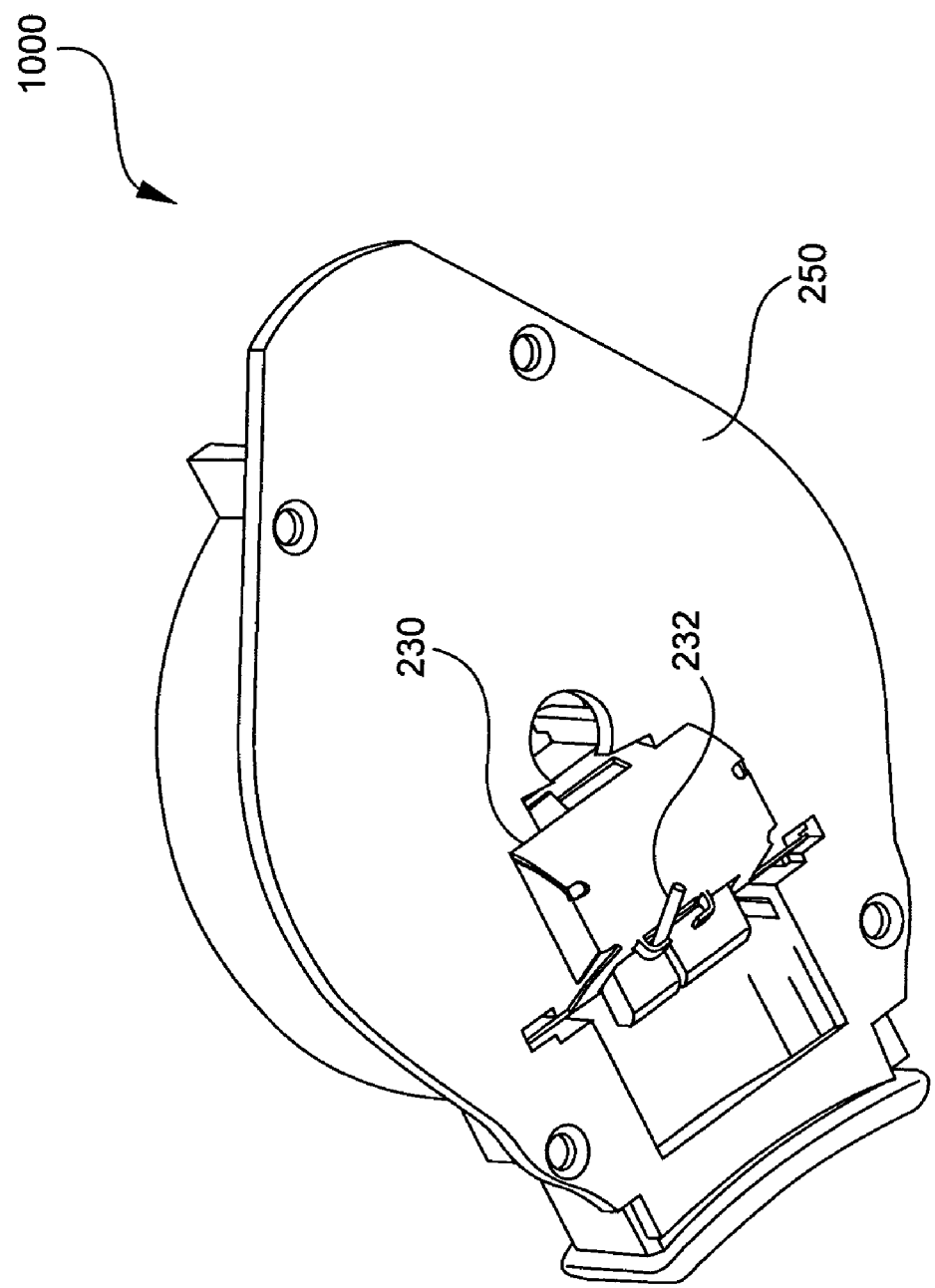
FIG. 17B is a perspective view of a rotating safety shield feature of an embodiment of the present invention after energizing, activation and removal from the user's skin surface.

In one version of a safety feature embodiment, a passive rotating patient needle cover as shown in FIGS. 17A and 17B is provided. FIG. 17A is a perspective view of a safety shield feature of an embodiment of the present invention before energizing and activation, and FIG. 17B is a perspective view of the safety shield feature after energizing and activation.

The rotating shield 230 can be powered by a preloaded torsion spring 232, shown in FIG. 10B, and remains loaded in an "up" rotated position until the button of the push button subassembly is pressed. The shield 230 is then free to rotate, but is prevented from rotating to a full deployment position by the presence of the user's skin against the adhesive covered surface of the device. When the device is no longer against the user's skin, such as when the device is removed or falls free, the shield 230 is no longer obstructed by the skin surface and rotates about 180 degrees, and is thereafter locked into place, fully covering the patient needles 222 and preventing needle stick injuries.

Figure 18A:
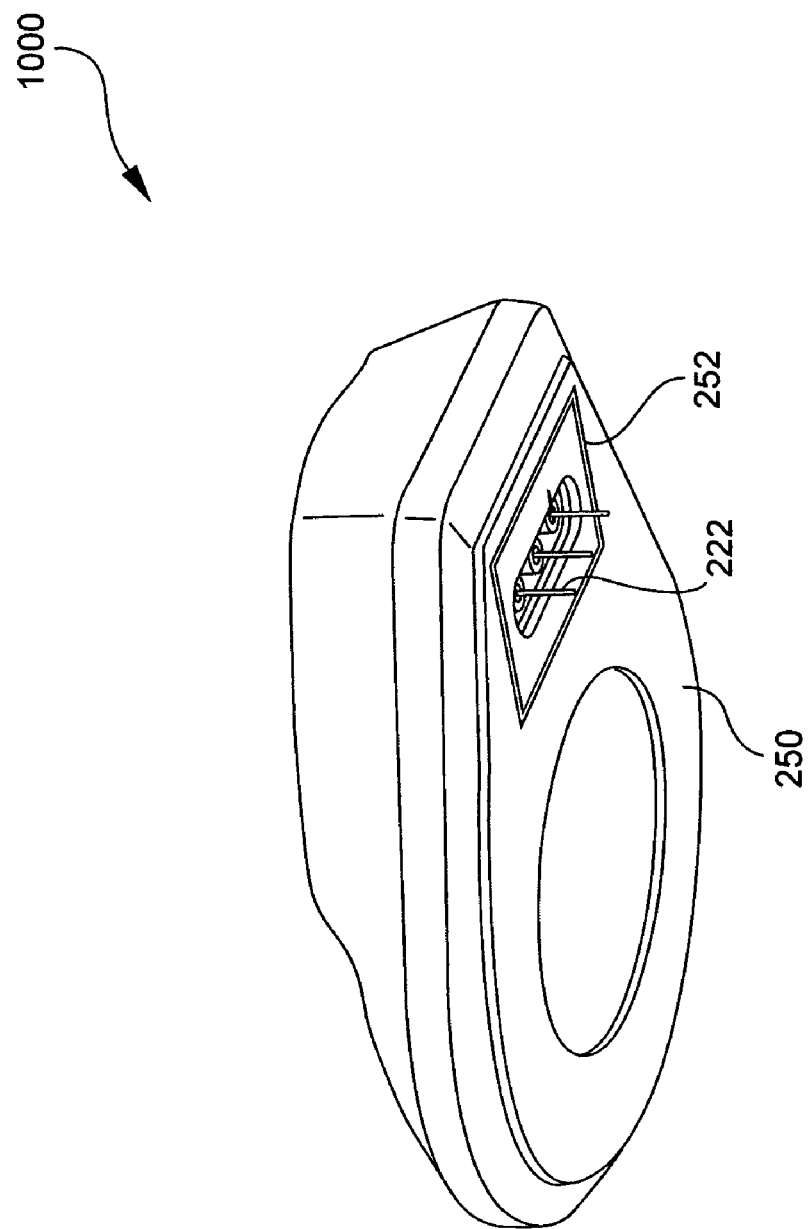
FIG. 18A is a perspective view of an extending safety shield feature of an embodiment of the present invention prior to energizing and activation.
Figure 18B:
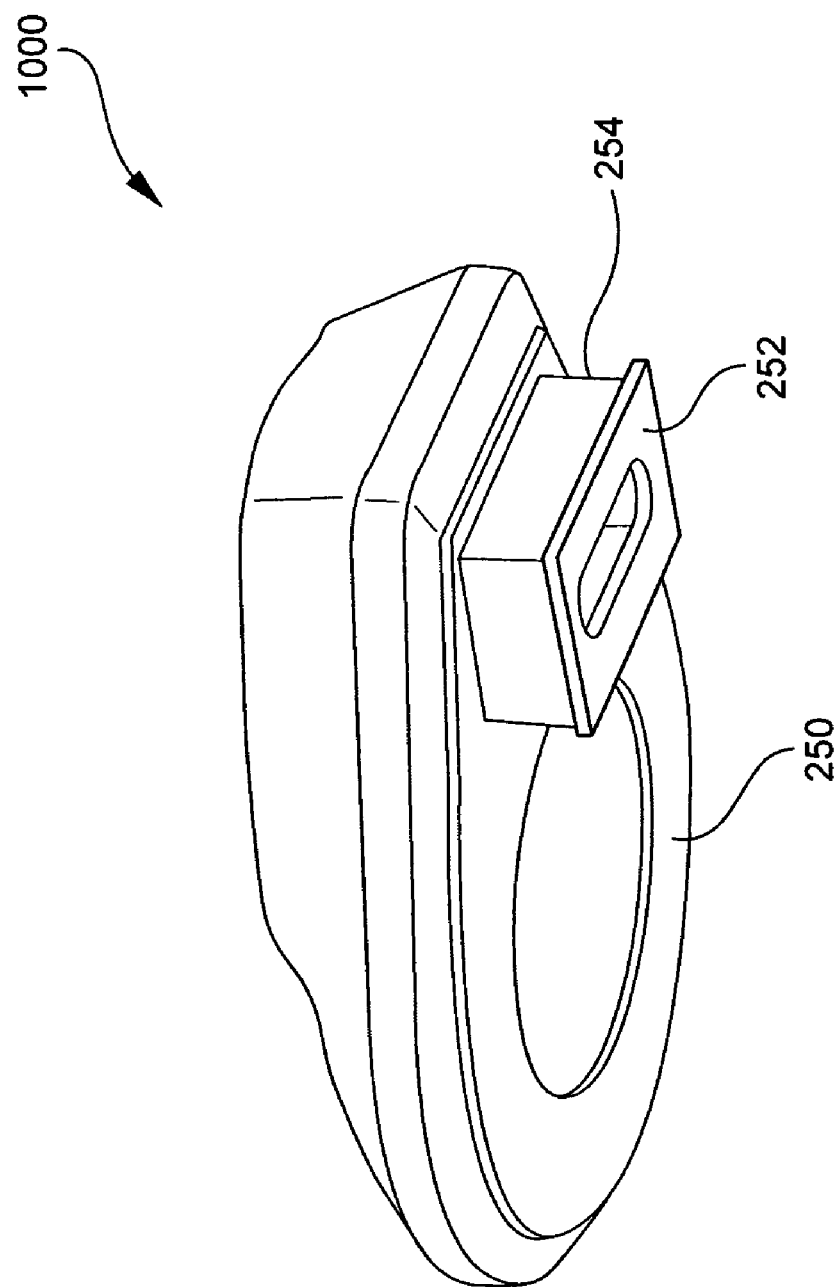
FIG. 18B is a perspective view of an extending safety shield feature of an embodiment of the present invention after energizing, activation and removal from the user's skin surface.

In another version of a safety feature embodiment, a safety housing is provided as shown in FIGS. 18A and 18B which provides in part, a flat surface portion 252 that is in contact with the patient's skin. FIG. 18A is a perspective view of a safety shield feature of an embodiment of the present invention before energizing and activation, and FIG. 18B is a perspective view of the safety shield feature after energizing and activation.

The surface 252 also includes an adhesive disposed thereon such that when the device is removed by the patient from the skin, the adhesive will act to deploy (i.e., retract or extract), the safety housing 254 from the interior of the device, thereby shielding the patient needles 222 which otherwise would be exposed upon removal from the patient. The extended safety housing 254 is then locked into place as shown in FIG. 18B and prevents accidental injury or exposure to the patient needles.

Still other versions of a safety feature embodiment include a flexible patient needle cap 240 which serves to protect the patient needles and provide a sterile barrier. The needle cap can serve to protect the patient needles during device manufacture, protect the user prior to use, and provide a sterility barrier at any point prior to removal. The needle cap 240 can be attached via a press fit with the patient needle manifold 220, and further provides a flexible member 242 which can be used to secure the cap to the pull handle 260. As described above, the removal of the retaining pin 140 can also serve to remove the needle cap 240, and the cap and/or pull handle can further provide an interlock with the button of the push button subassembly.

Yet another active safety device feature can be provided separately, or in combination with the features described above, which allows the user to position or activate the shield when required. For example, the safety feature may include on or more lever or rotating mechanisms as described above, which may be manually toggled, or flipped, between an exposed and a shielded position, allowing the user to actively shield the patent needles after use and prevent accidental injury or exposure to the needles.

In each safety device version described above, the force to deploy the safety mechanisms described is less than the peel force to remove the device from the skin surface, and typically require an applied force to defeat the locking mechanism of more than 3 pounds. For example, the safety mechanisms should each provide needle tip protection from an applied finger tip load of 2 pounds. Additional details of an extending shield and use are further discussed in U.S. patent application Ser. No. 60/397,038, and Ser. No. 60/407,284, referenced above, the entire contents of each being incorporated herein by reference. Additional details of a rotating shield and use are further discussed in U.S. patent application Ser. No. 60/447,359, Ser. No. 60/450,680, and Ser. No. 60/450,681, referenced above, the entire contents of each being incorporated herein by reference.

In addition to the performance advantages described above, another advantage of the embodiment of FIG. 1 described above is the ability to make two or more distinct, self-contained subassemblies that allow for assembly flexibility. Each subassembly is self contained and stable, and provides the ability to separate the reservoir assembly from remaining components, allowing separate filling and inspection of the reservoir, while preventing the unnecessary handling of the remaining components. Additionally, should any of the additional components be discarded, the costly reservoir contents can be excluded. Also, the reservoir contains no unnecessary parts and as a result, brings a low particle load into filling operations. Also, all stored energy components are in the body subassembly so they cannot be inadvertently deployed during filling of the reservoir. Specifically, no springs are included in the reservoir which prevents the chance of unwanted spring release during filling. As noted, minimal extraneous components in the reservoir reduce particle load, and only contains necessary components, such as the reservoir, lid, septum and stopper. No dangling parts are present, and remaining parts for remaining subassemblies typically require only drop-in assembly steps.

A further advantage of the embodiment of FIG. 1 described above includes the location of patient needles near the center of the device footprint. Such placement reduces the effects of needle displacement due to device movement, such as "rocking". The patient needle manifold is constructed having a low mass, due in part to providing a separate manifold for the septum, thus providing a higher patient needle manifold velocity during activation. The patient needle manifold is provided with independent direct drive of patient needles, as the drive springs are located directly over the patient manifold, and serve to drive the patient needle manifold exclusively. The septum penetration force and boot collapse force have no influence on patient needle manifold movement. Additionally, there is room to include larger needle spacing and a lower activation force is sufficient, however, inadvertent activation due to such lower forces is prevented by numerous activation lockouts.

Sufficient room is also provided for a traditional urethane septum needle boot, as well as sufficient room allowing the use of flexible tubing, or any number of flow restrictors, such as capillary tubes, for flow restriction. This can be provided while still maintaining a smaller device footprint. Additionally, the reservoir can be located on top of the device, which can allow full and unobscured view of the drug reservoir through a transparent component, allowing view of the reservoir contents to the user or manufacturer.

Second Embodiment

Figure 19A:
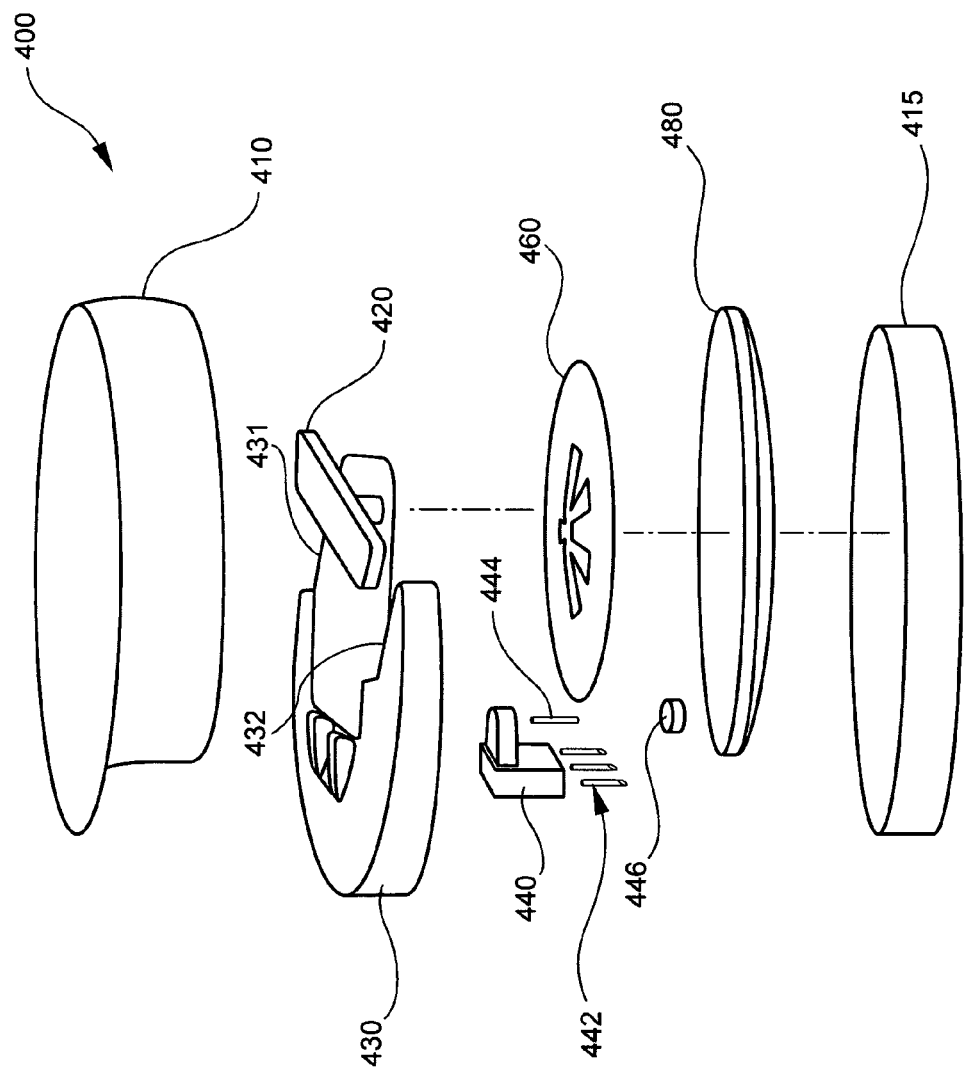
FIG. 19A is an exploded perspective view of a second embodiment of a patch-like injector or infuser system using a side push button.
Figure 19B:
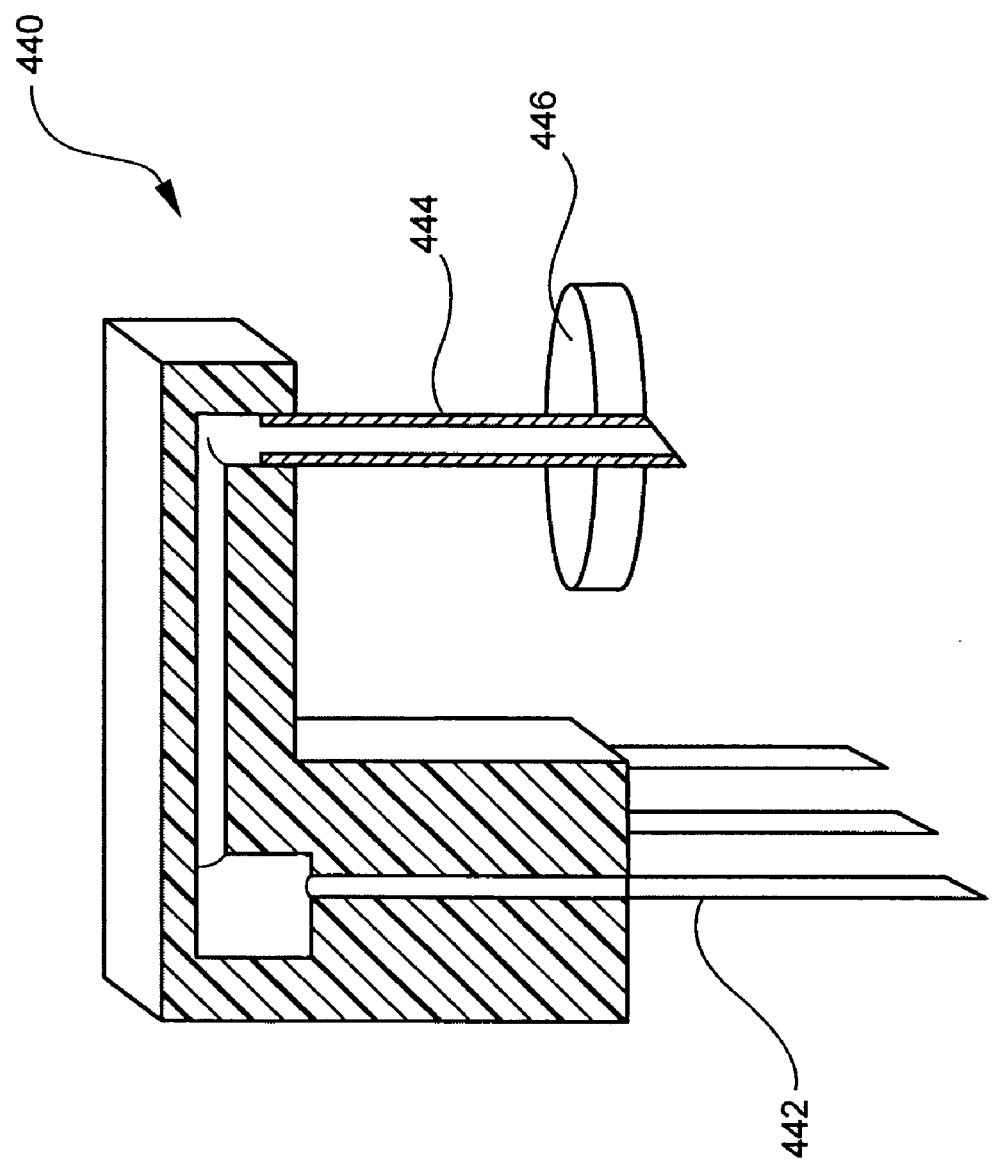
FIG. 19B is a cross-sectional view of the patient needle/septum needle manifold system of the second embodiment shown in FIG. 19A.

A second embodiment of the device, shown in FIGS. 19A and 19B, is a push-button design 400 wherein the activation and energizing of the device is accomplished in a single multi-function/step process. FIG. 19A is an exploded perspective view of a second embodiment of a patch-like injector or infuser system using a side push button, FIG. 19B is a cross-sectional view of the patient needle/septum needle manifold system of the second embodiment, FIG. 19C is a cross-sectional view of the second embodiment shown in FIG. 19A prior to energizing and activation, and FIG. 19D is a cross-sectional view of the second embodiment shown in FIG. 19A after energizing and activation.

The device of FIGS. 19A through 19D includes a top housing 410 and rigid bottom 415, a spring lock pin 420, a push button 430, a manifold 440, a Belleville spring 460, and a reservoir lid 480. The manifold 440 further includes one or more patient needles 442 and at least one septum needle 444 to pierce a septum 486.

Figure 19C:
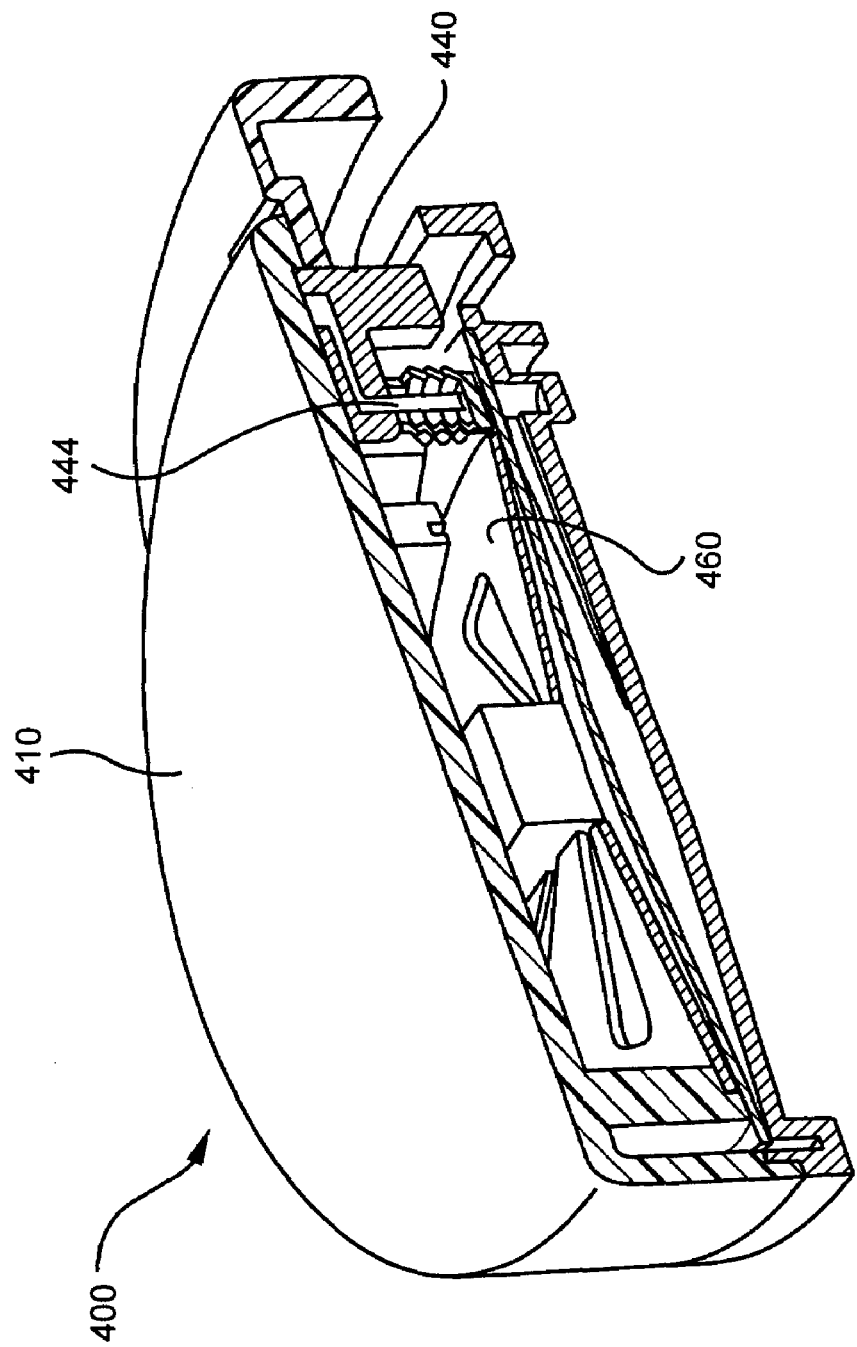
FIG. 19C is a cross-sectional view of the second embodiment shown in FIG. 19A prior to energizing and activation.
Figure 19D:
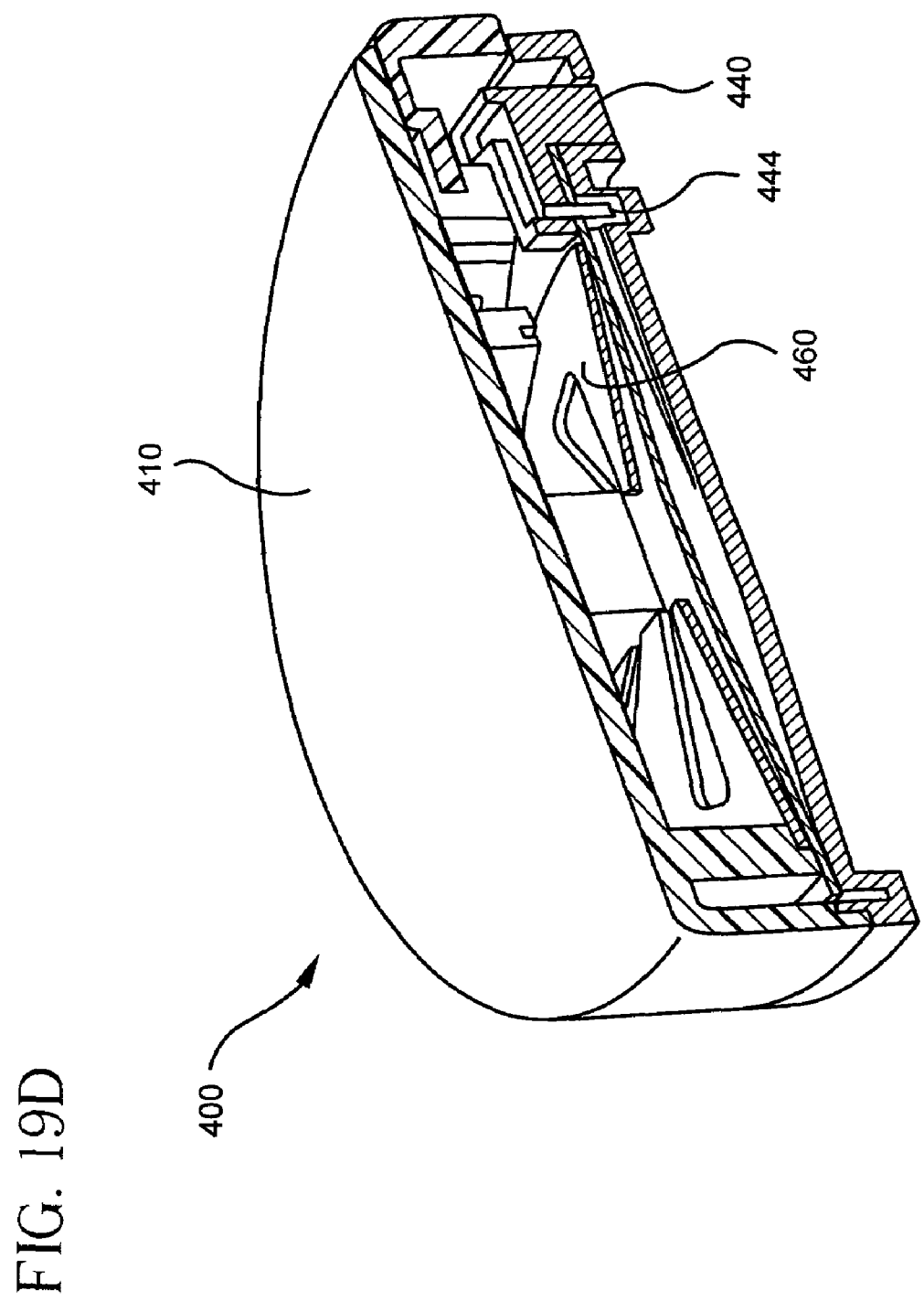
FIG. 19D is a cross-sectional view of the second embodiment shown in FIG. 19A after energizing and activation.

The device of FIGS. 19A and 19C is activated and energized by pressing the slide button 430 such that cams 431 and 432 on an inner portion of the button lift the spring lock pin 420 and release the spring 460 thereby pressurizing the reservoir system. As the button 430 continues along its travel as shown in FIG. 19D, the button engages a number of cam mechanisms which lower the needle assembly and manifold 440, having both the patient needles 442 and the septum needle 444 (positioned in the same direction), as shown in FIG. 19B, toward the skin of the patient.

Specifically, in addition to energizing the reservoir of the device by releasing the constant force spring 460, the camming surfaces on the interior of the button 430 engage a mating surface on the needle manifold assembly 440 thereby driving the manifold assembly toward an opening in the underside of the device. Continued travel of the button forces the protruding needles 442 of the needle manifold 440 into the skin of the user and causes the fluid access spike, or septum needle 444, into the interior of the reservoir thereby initiating flow of the fluid from the reservoir to the skin of the user once the needles are positioned. As the needles 442 and 444 both face the skin surface, the skin contact and bladder piercing function of each is guaranteed. As will be recognized by one skilled in the art, the cam surfaces on the button assembly can be configured to alter the speed, or rearrange the sequence of events just described. Additional details of a push-button design wherein the activation and energizing of the device is accomplished in a single multi-function/step process are further discussed in U.S. patent application Ser. No. 60/397,038, referenced above, the entire content of which is incorporated herein by reference.

Third Embodiment

Figure 20A:
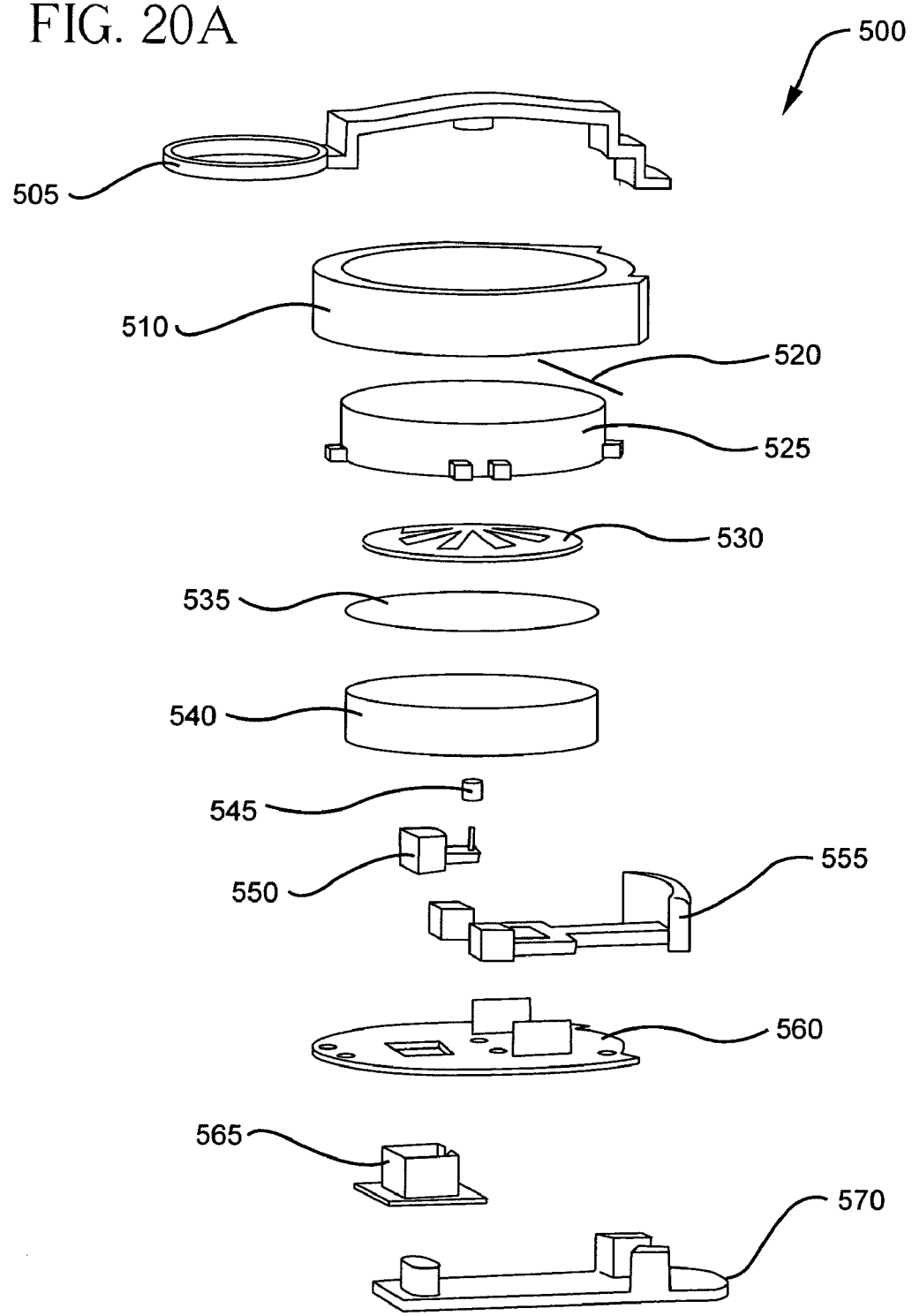
FIG. 20A is an exploded perspective view of a third embodiment of a patch-like injector or infuser system using a side push button.
Figure 20B:
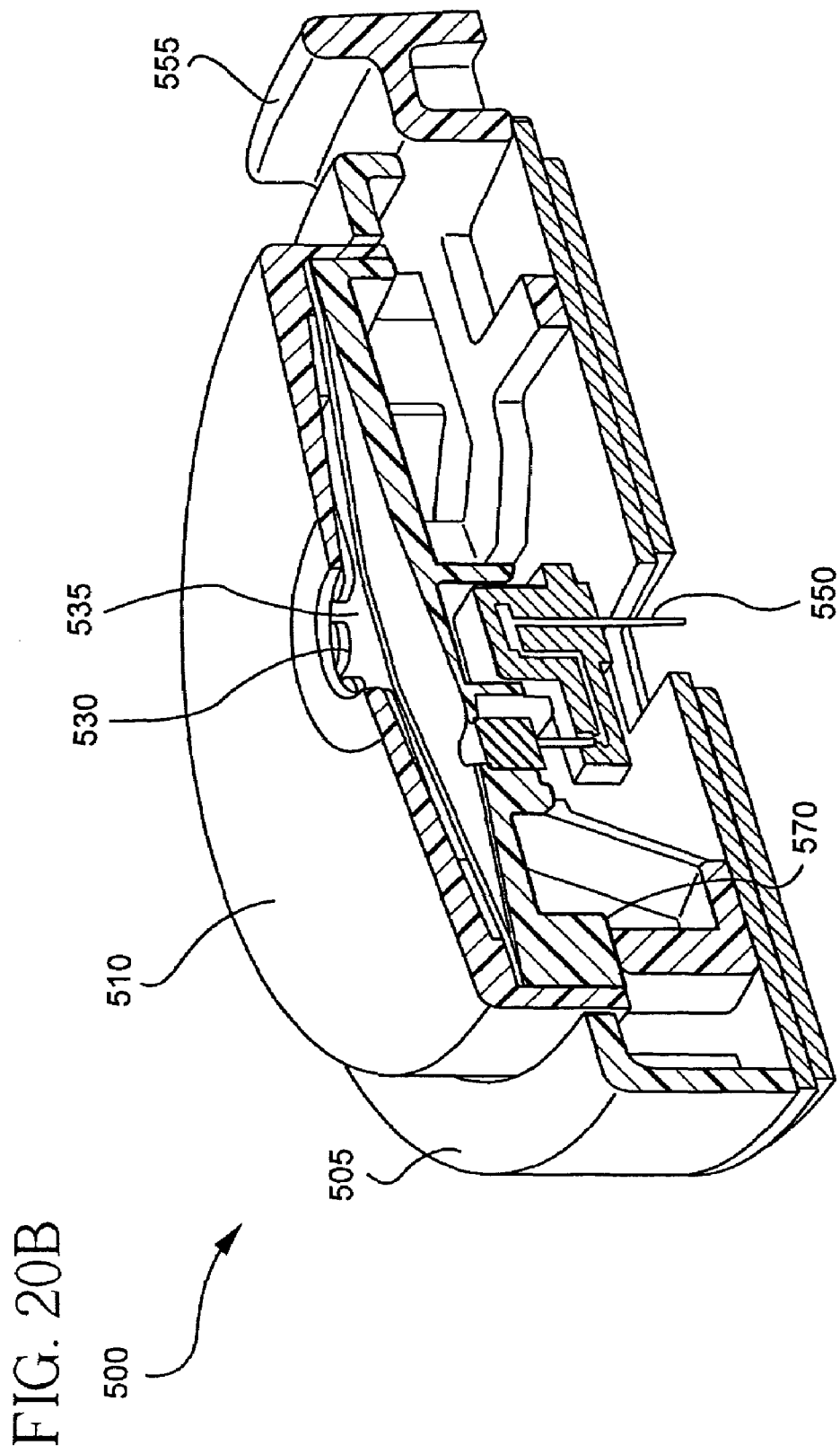
FIG. 20B is a cross-sectional view of the third embodiment shown in FIG. 20A prior to energizing and activation.
Figure 20C:
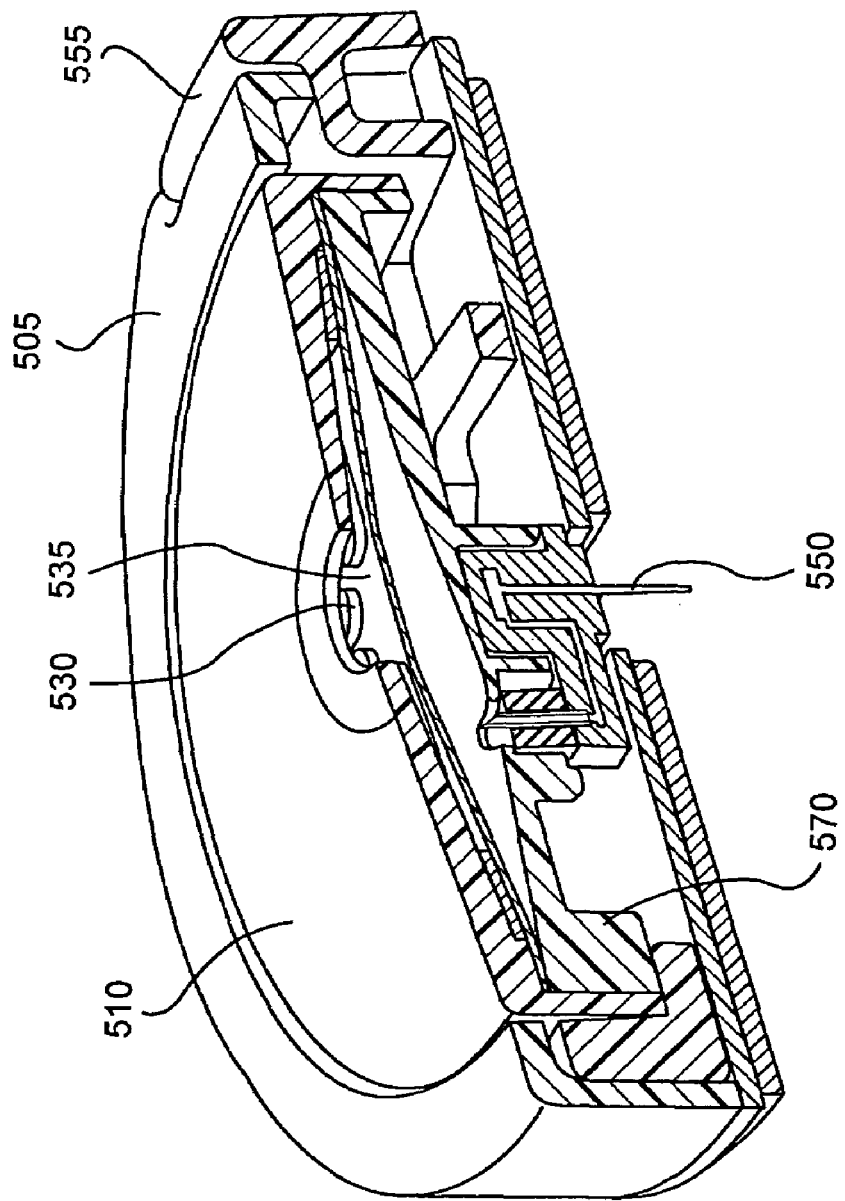
FIG. 20C is a cross-sectional view of the third embodiment shown, in FIG. 20A after energizing and activation.

A third embodiment of the device, shown in FIGS. 20A through 20C, is a push-button design 500 wherein the bladder itself moves towards the patient's skin and contacts a manifold having both the patient needles and the septum needle (positioned in opposite directions), and forces the patient needles into the patient's skin, and the septum needle into the septum. FIG. 20A is an exploded perspective view of a third embodiment of a patch-like injector or infuser system using a side push button, FIG. 20B is a cross-sectional view of the third embodiment shown prior to energizing and activation and FIG. 20C is a cross-sectional view of the third embodiment shown after energizing and activation.

The device of FIGS. 20A through 20C includes a pull pin handle 505, a top housing 510, a leaf spring 520, a reservoir top 525, a Belleville spring 530, a reservoir lid 535, a reservoir bottom 540, a septum 545, a manifold system 550, a push button 555, a bottom housing 560, a safety clip 565 and a needle clip 570. In a manner similar to the first embodiment described above, the user energizes the device of the third embodiment shown in FIG. 20B by removing the pull pin handle 505 from the device. Once this is done, the device is energized as the Belleville spring 530 is now free to press downward on the reservoir, pressurizing the fluid within the reservoir system, and forcing the reservoir downward for engagement as shown in FIG. 20C and described in greater detail below.

In the third embodiment shown in FIG. 14, the device is activated by sliding the button 555 toward the center of the device until the button is no longer holding the reservoir bottom 540 in place against the top housing 510 and against the force of the leaf spring 520. Since a portion of the reservoir system, the reservoir top 525 is preferably rigid and spring loaded, and the reservoir lid 535 is sealingly connected to the reservoir bottom 540, the reservoir system now moves downward toward the patient's skin as a single unit. A septum 545 may also be located on the reservoir bottom 540. A needle containing manifold 550 is attached to the rigid bladder assembly, and it too moves towards the patient's skin until the patient needles penetrate the skin. At this time, the needle manifold bottoms out on the bottom housing 560 of the device. The reservoir assembly continues downward slightly and causes the fluid access spike, or septum needle, to penetrate the septum 545, thereby initiating flow of fluid from the reservoir and through the patient needle or needles.

One unique characteristic of the third embodiment is that the septum needle accesses the reservoir from below as the reservoir moves downwards. This allows the device to collapse in height, and allows the device to have a lower profile once activated. In addition, since the septum needle penetration is in the opposite direction of the patient needle penetration, it does not require additional height within the device allowing the septum needle to be maintained in a sterile condition without the necessity for additional interior space or overall device height. Additional details of a push-button design wherein the bladder itself moves towards the patient's skin and contacts a manifold having both the patient needles and the septum needle are further discussed in U.S. patent application Ser. No. 60/397,038, referenced above, the entire content of which is incorporated herein by reference.

Fourth Embodiment

Figure 21A:
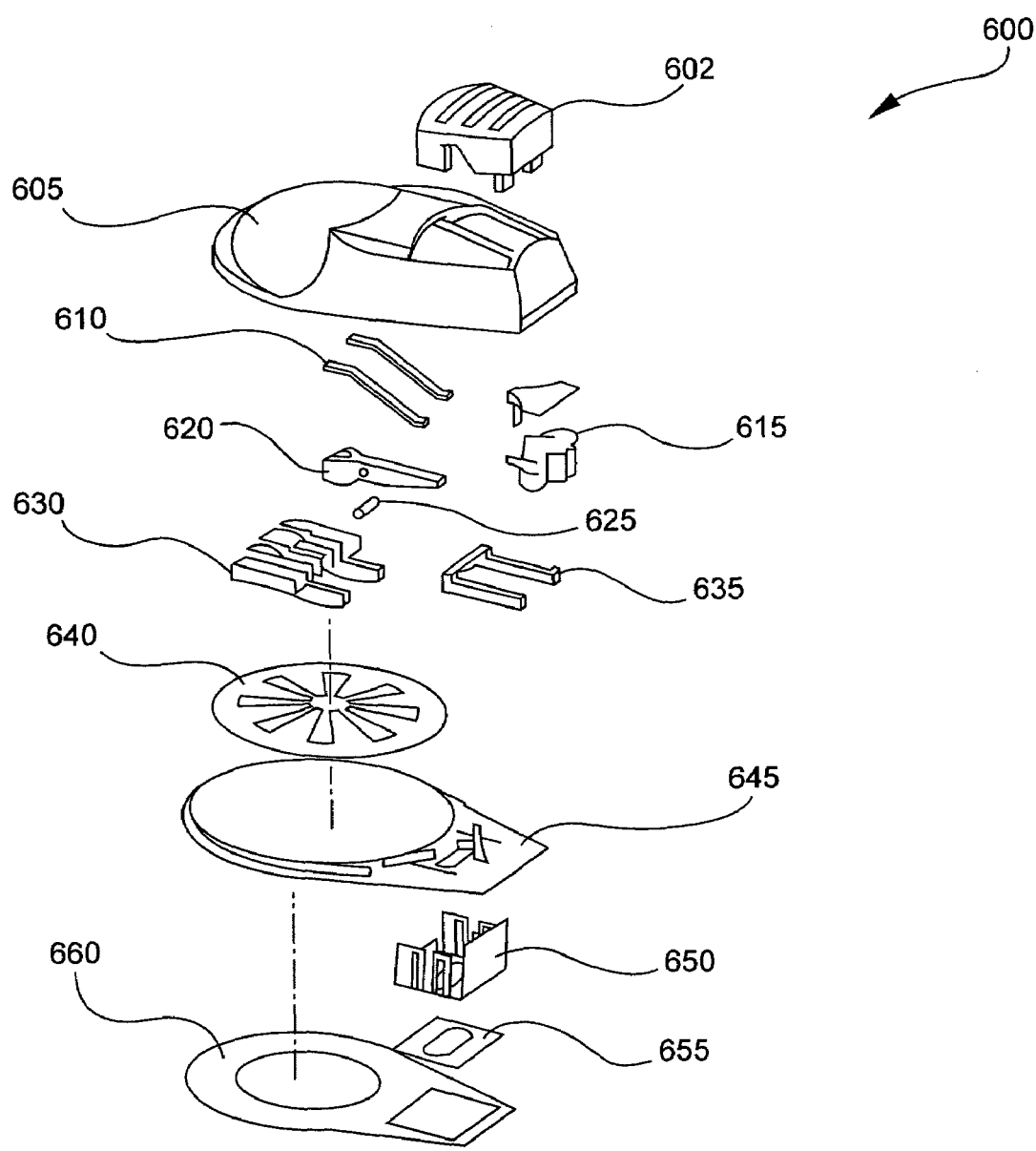
FIG. 21A is an exploded perspective view of a fourth embodiment of a patch-like injector or infuser system using a top push button.
Figure 21B:
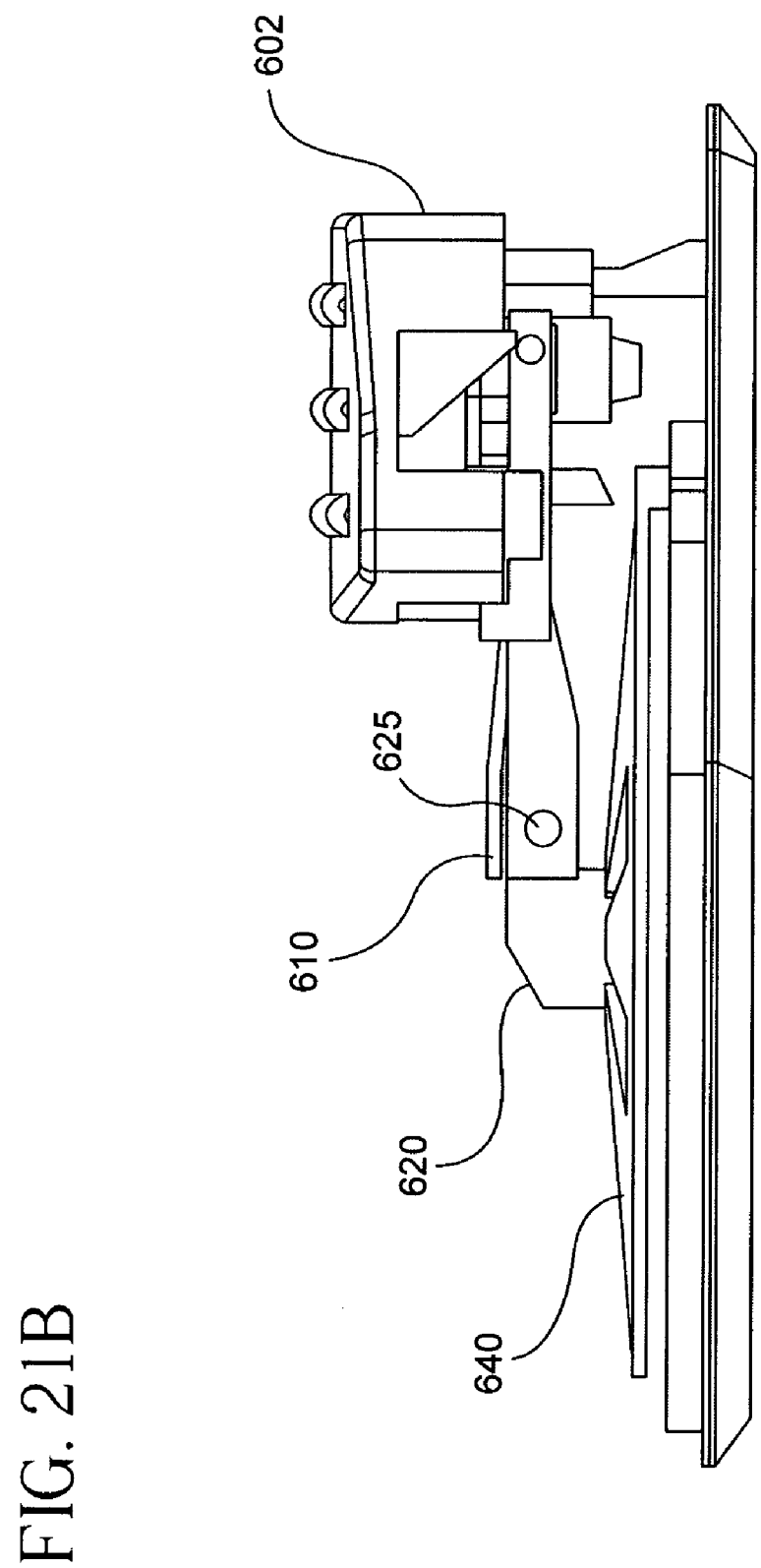
FIG. 21B is a partial cross-sectional view of the fourth embodiment shown in FIG. 21A prior to energizing and activation.
Figure 21C:
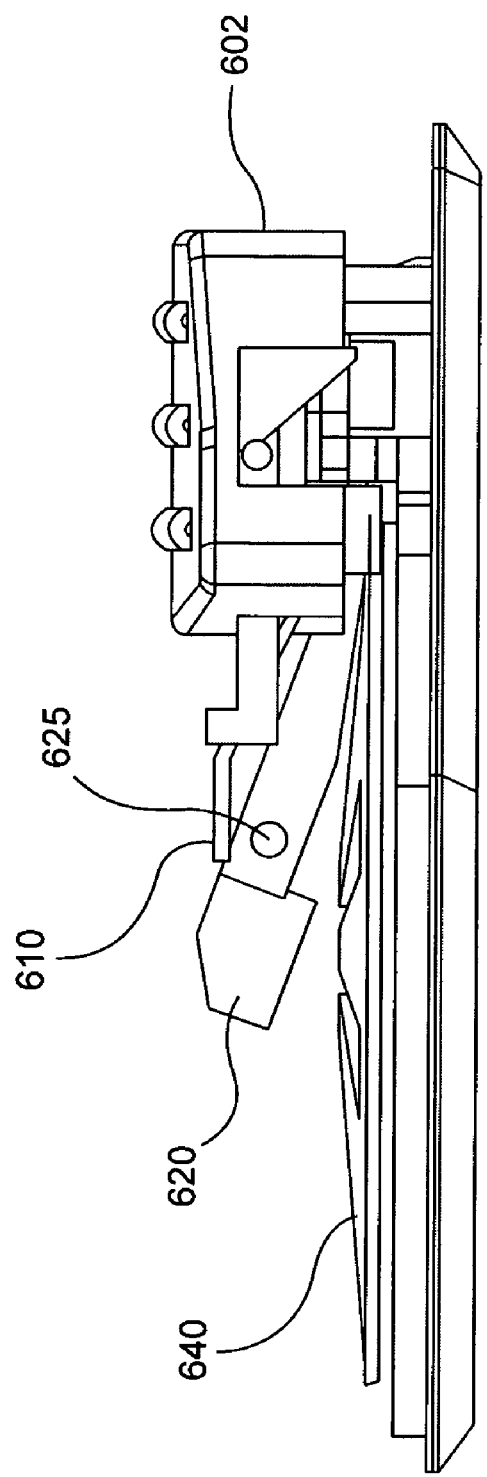
FIG. 21C is partial cross-sectional view of the fourth embodiment shown in FIG. 21A after energizing and activation.

A fourth embodiment of the device, shown in FIGS. 21A through 21C, is a push-button design wherein the push-button is located on the top, outer surface of the device, and the user energizes and activates the fluid flow by depressing the button to its lower-most position. FIG. 21A is an exploded perspective view of a fourth embodiment of a patch-like injector or infuser system using a top push button, FIG. 21B is a partial cross-sectional view of the fourth embodiment shown in FIG. 21A prior to energizing and activation, and FIG. 21C is partial cross-sectional view of the fourth embodiment shown in FIG. 21A after energizing and activation.

The device of FIG. 21A includes a top push button 602, an upper housing 605, leaf springs 610, a manifold assembly 615, pull pin 620, release guide 630, retainer 635, Belleville spring 640 and reservoir 645. As with the earlier embodiments described above, the adhesive 655 and 660 on the bottom surface of the device is exposed and the user presses the device against the skin in the desired area of the body to securely attach it. Once the device is in place and attached the user depresses the button 602 located on the top in this embodiment. The depression of the button 602 forces the manifold assembly 615 located directly beneath the button downward, and the manifold assembly contains an angled surface that mates with a protrusion on the release guide 630. As the manifold assembly 615 travels downward, the release guide 630 moves along the leaf springs 610 in the grooves or guides of the retainer 635 toward the pull pin 620 and its attachment to the constant force spring 640. The pull pin 620 is configured and shaped to fit within the retainer 635 and to be retained therein, preferably by a retaining pin 625. This configuration allows the pull pin 620 to rotate freely about the retaining pin 625. The release guide 630 meanwhile is forced along the guides within the retainer 635. The underside of the release guide 630 has a chamfered surface that slides along a mating chamfered surface on the pull pin 620, depressing the leaf springs 610 and one end of the pull pin and causing the pull pin to rotate about the retaining pin 625 and lift the other end of the pull pin where it is attached to the constant force spring 640. This rotation and lifting overcomes the retaining force of the pull pin and causes it to release the constant force spring and thereby energize the reservoir 645.

Occurring simultaneously with the downward travel of the push button, the manifold assembly 615 which contains a septum piercing needle or spike and the skin penetrating needle or needles is also pressed downward until the needles are fully embedded at the desired depth in the skin. The septum piercing spike then accesses the fluid within the reservoir, before or after the reservoir is energized depending upon the configuration, permitting the fluid within the reservoir to flow. As with the embodiments described above, each configuration can be altered to affect the timing and sequence of the events described above. Additional details of a push-button design wherein the push-button is located on the top, outer surface of the device, and the user energizes and activates the fluid flow by depressing the button to its lower-most position are further discussed in U.S. patent application Ser. No. 60/407,284, referenced above, the entire content of which is incorporated herein by reference.

Test Results

Figure 22:
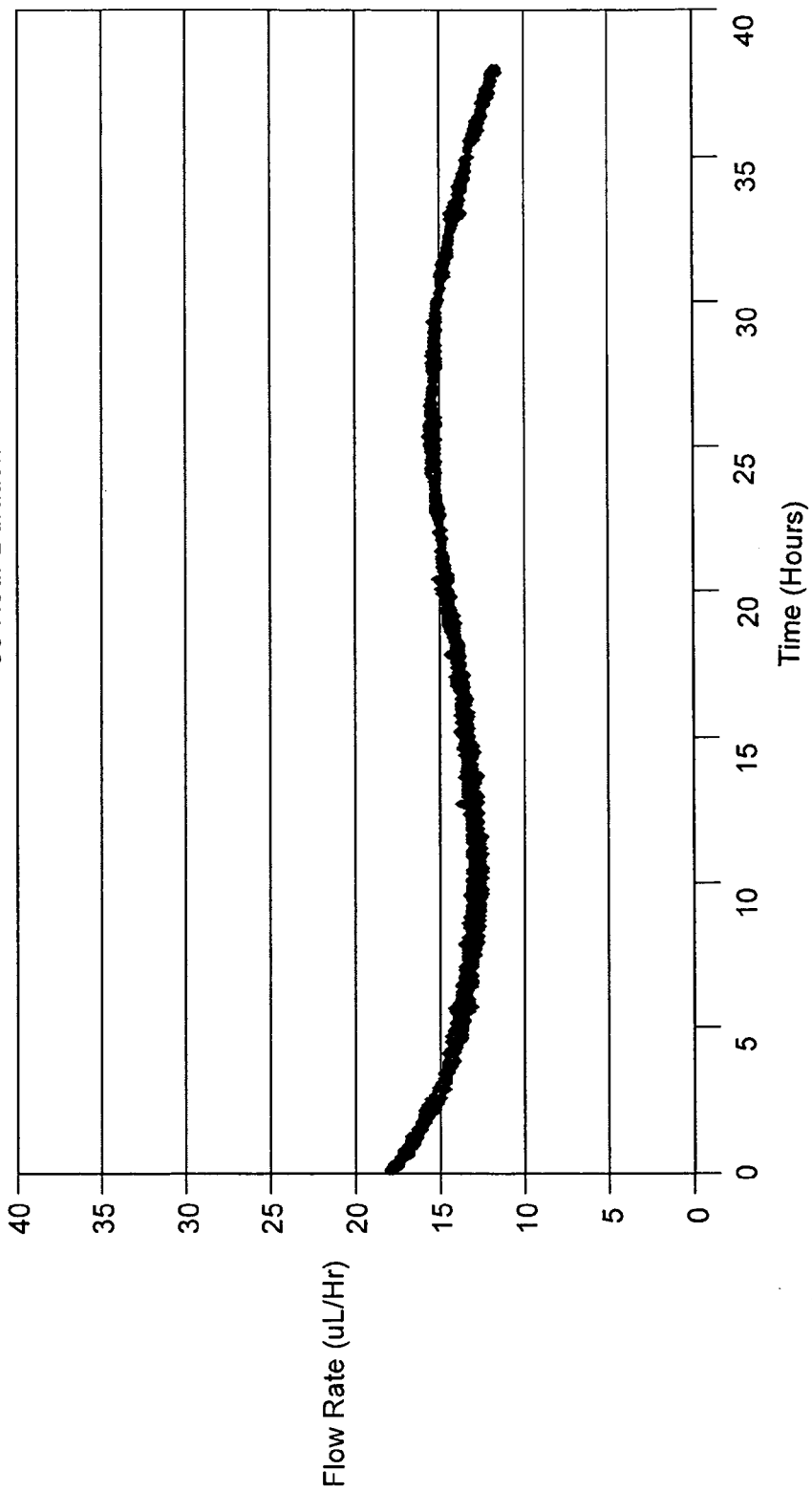
FIG. 22 is an example of in vitro infusion data showing a flow rate over a period of 38 hours.

Various results and comparisons between embodiments of the preferred device and other techniques and devices are shown in FIGS. 22 through 26. The graph of FIG. 22 shows the flow rate uniformity over an extended delivery time in vitro to establish the measured flow rate that is subsequently used in a diabetic swine trial. This is further illustrated in FIG. 26, which shows pressure versus volume delivered data in accordance with an embodiment of the present invention. The use of the Belleville spring to apply pressure to the flexible reservoir results in a near constant delivery rate over an infusion period of 25 hours using the embodiment of FIG. 1 described above.

Figure 24:
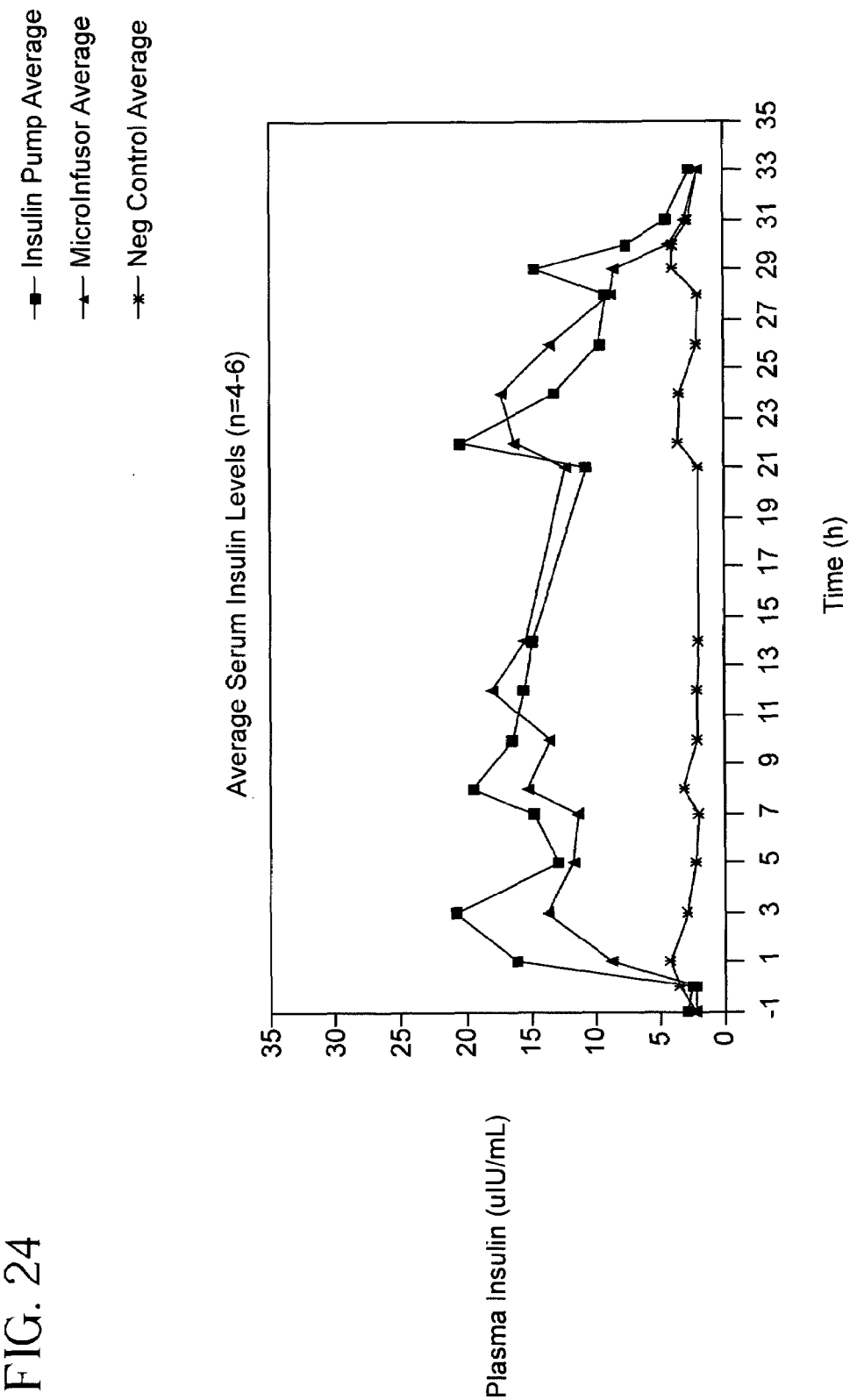
FIG. 24 is a plot illustrating an example of blood insulin level data.

The graph of FIG. 24 shows the average blood insulin levels (pharmacokinetic response) measured in several animals over the insulin delivery period. This is initially very low, due to the diabetic state of the animal, and then increases to much higher levels during infusion. At the end of the infusion, the insulin levels return to the low baseline levels. Minor peaks occur in the average baseline insulin levels of negative control animals receiving no insulin. These peaks reflect a minimal endogenous insulin secretion by the animals in response to feeding times at −1, 7, 14, 21, and 28 h. The infusion data illustrated in FIG. 22 further shows that results in accordance with an embodiment of the present invention described above are substantially as desirable as results obtained using a standard insulin pump. Further details of pharmacokinetic profiles are discussed in a U.S. Patent Application Publication No. 2002/0095134, entitled "Method For Altering Drug Pharmacokinetics Based On Medical Delivery Platform", filed Jun. 29, 2001, the entire content of which is incorporated herein by reference.

Figure 23:
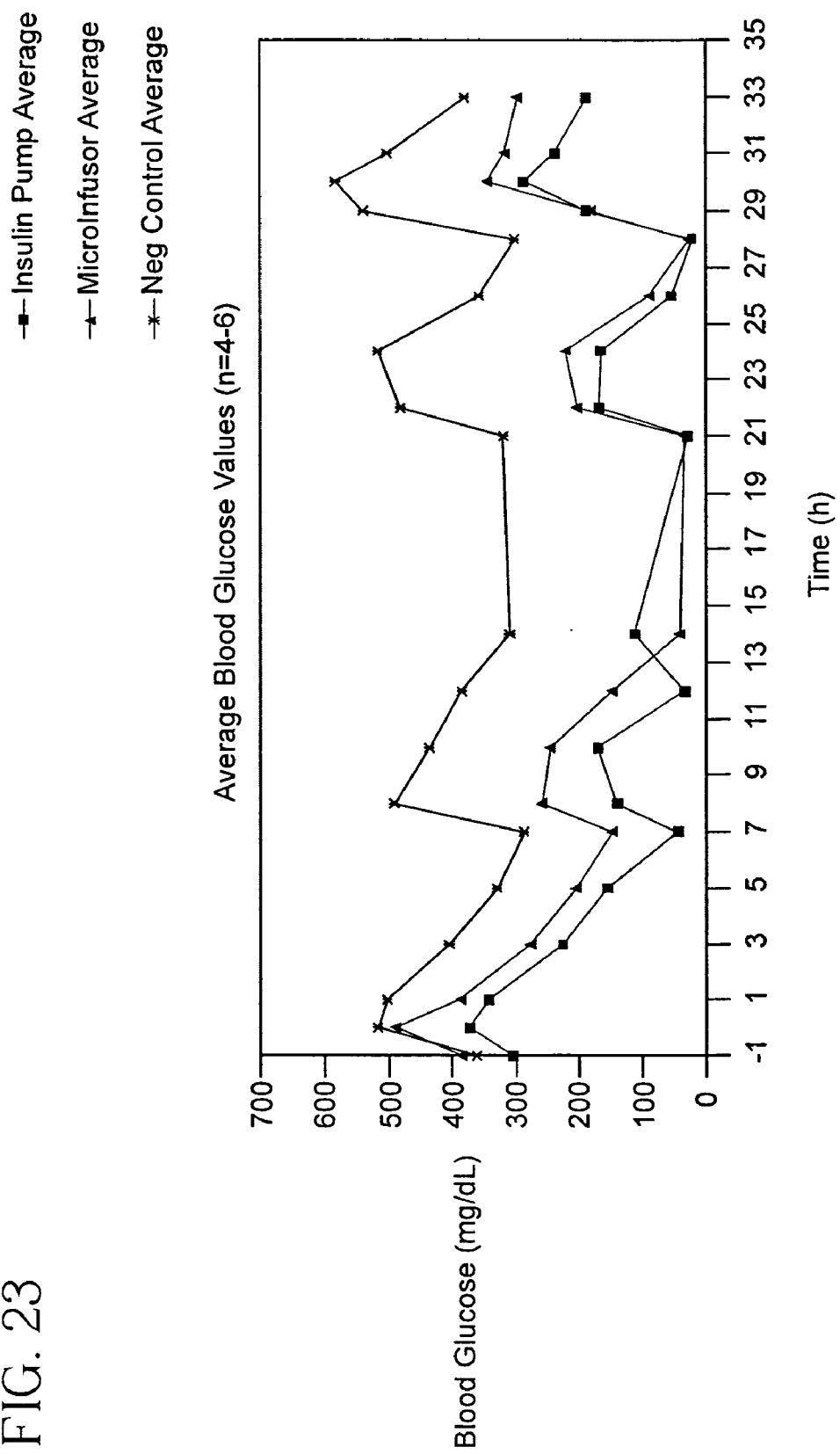
FIG. 23 is a plot illustrating an example of blood glucose level data.

The graph of FIG. 23 shows the average blood glucose level measured in several animals over the insulin delivery period (pharmacodynamic response) in accordance with an embodiment of the present invention. The blood glucose level is influenced by feeding and any additional glucose given to the animal to prevent hypoglycemic injury. As a result, there are periodic spikes in glucose level, corresponding to feeding times at hours−1, 7, 14, 21, and 28. The blood glucose values of both infusor and insulin pump treated animals fall drastically within the first 5 hours of insulin delivery. Blood glucose levels remain substantially below the response of negative control diabetic animals receiving no insulin for the remainder of the experimental period. The blood glucose effects obtained with the infusor, as illustrated in FIG. 23, are substantially equivalent to the results obtained using a standard insulin pump. Note that in both FIGS. 22 and 23, the performance of the pump and the microinfusor are quite similar, resulting in very similar physiological responses.

Figure 25:
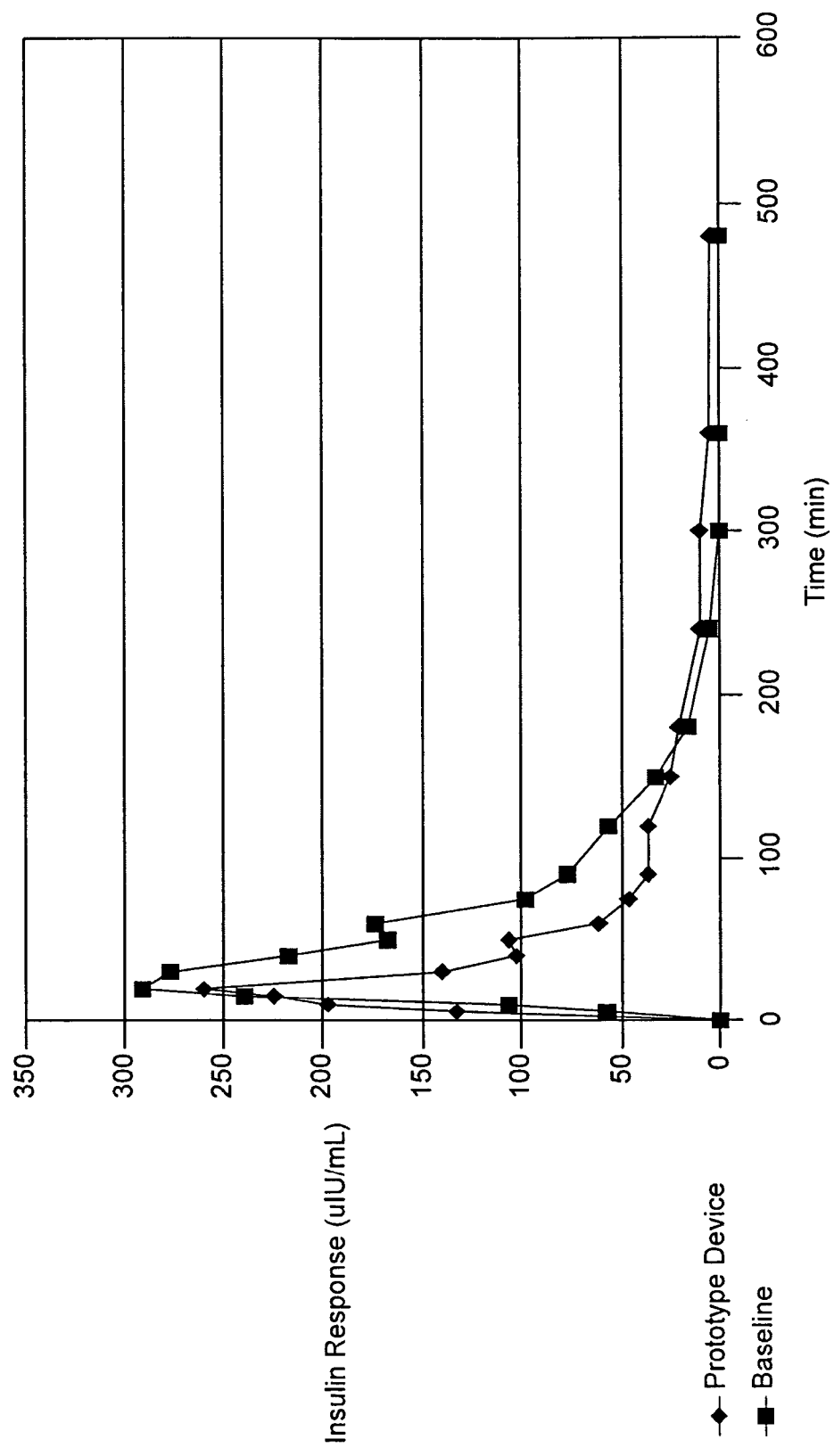
FIG. 25 is a plot illustrating an example of insulin response data.
Figure 26:
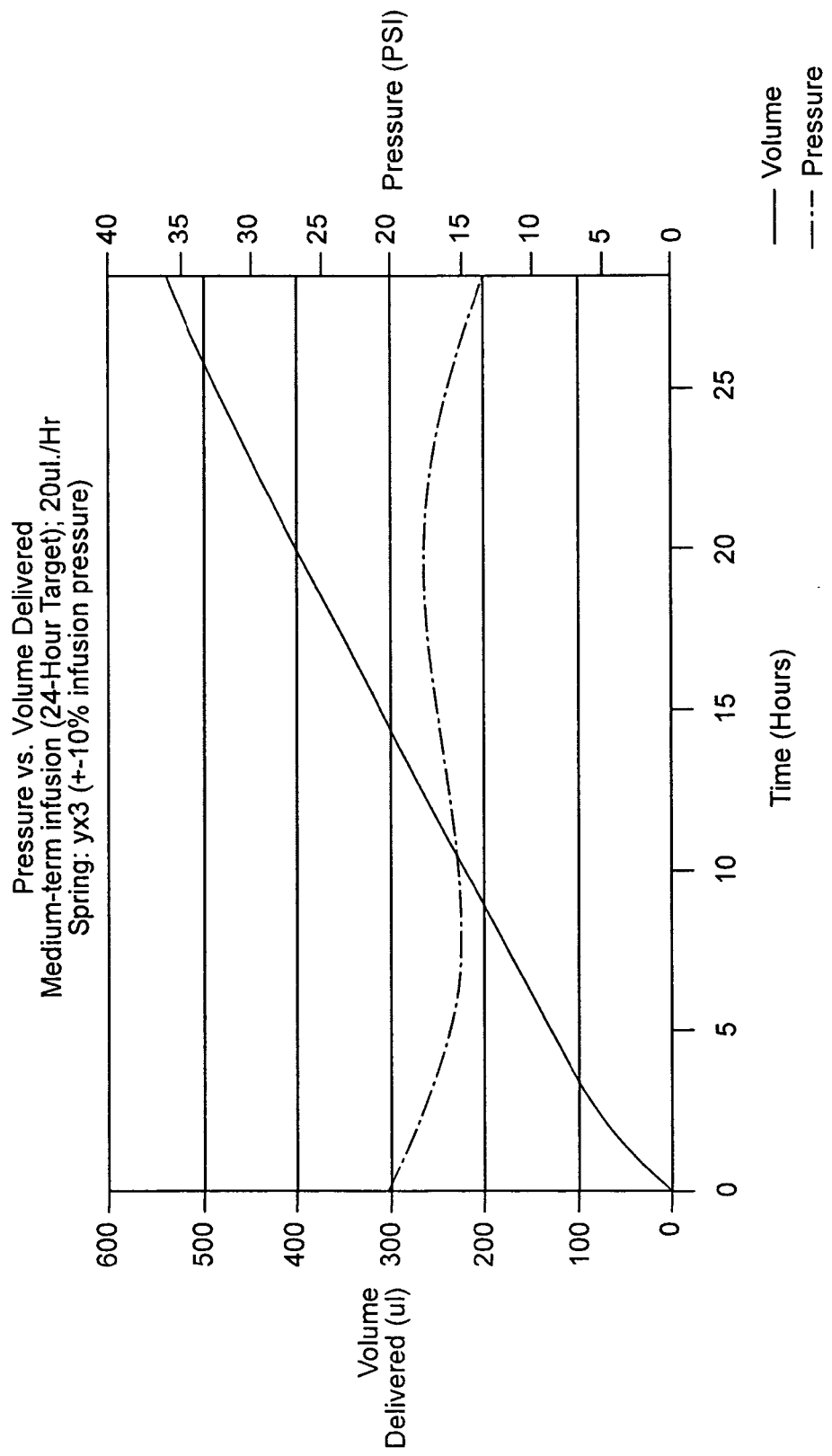
FIG. 26 is a plot illustrating an example of pressure versus volume-delivered data.

The graph of FIG. 25 shows the blood insulin levels (pharmacokinetic response) measured in an animal receiving insulin from an infusor designed to deliver a larger dose of insulin as a "metered bolus" over a few minutes time period. In the embodiment of FIG. 1, the infuser performs substantially as well as results obtained from a subcutaneous injection using a standard syringe.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A patch-like infusion device, comprising:
   a fluid reservoir having at least one flexible wall;
   at least one patient needle in selective fluid communication with said reservoir;
   a Belleville spring having a central aperture for applying pressure to said flexible wall to cause fluid to flow from said reservoir to said patient needle; and
   a pin engageable with said central aperture and disengageable therefrom for causing said Belleville spring to begin applying said pressure when said infusion device is placed into operation wherein disengagement of said pin from said central aperture occurs automatically when the user performs another operation on said infusion device wherein said operation comprises removing a pull handle operatively coupled to said pin.

2. A patch-like infusion device as claimed in claim 1, wherein disengagement of said pin from said aperture provides at least one of an audible indication and a tactile indication to a user of said infusion device.

3. A patch-like infusion device as claimed in claim 1, wherein said operation comprises operating a pushbutton operatively coupled to said pin.

4. A patch-like infusion device as claimed in claim 3, wherein said operation comprises removing a pushbutton guard or interlock.

5. A patch-like infusion device as claimed in claim 1, wherein said operation comprises operating a pull handle operatively coupled to said pin.

6. A patch-like infusion device as claimed in claim 3, wherein said operation of said pushbutton begins selective fluid communication of said at least one patient needle with said reservoir.

7. A patch-like infusion device as claimed in claim 6, wherein said selective fluid communication of said at least one patient needle with said reservoir is by piercing a septum engaged to said reservoir which selectively seals said reservoir.

* * * * *